United States Patent
Hughes

(10) Patent No.: US 10,246,421 B2
(45) Date of Patent: Apr. 2, 2019

(54) INDAZOLYL- AND INDOLYL-BENZAMIDE DERIVATIVES

(71) Applicant: ESANEX, INC., Indianapolis, IN (US)

(72) Inventor: Philip F. Hughes, Chapel Hill, NC (US)

(73) Assignee: Esanex, Inc., Indianapolis, IN (US)

( * ) Notice: Subject to any disclaimer, the term of this patent is extended or adjusted under 35 U.S.C. 154(b) by 0 days.

(21) Appl. No.: 14/851,542

(22) Filed: Sep. 11, 2015

(65) Prior Publication Data

US 2016/0075662 A1  Mar. 17, 2016

Related U.S. Application Data

(60) Provisional application No. 62/049,152, filed on Sep. 11, 2014.

(51) Int. Cl.
| | |
|---|---|
| C07D 231/54 | (2006.01) |
| C07D 409/12 | (2006.01) |
| C07D 405/12 | (2006.01) |
| C07D 401/12 | (2006.01) |
| C07D 403/12 | (2006.01) |
| A61K 31/416 | (2006.01) |
| A61P 35/00 | (2006.01) |
| A61P 29/00 | (2006.01) |

(52) U.S. Cl.
CPC ......... *C07D 231/54* (2013.01); *C07D 401/12* (2013.01); *C07D 403/12* (2013.01); *C07D 405/12* (2013.01); *C07D 409/12* (2013.01)

(58) Field of Classification Search
CPC combination set(s) only.
See application file for complete search history.

(56) References Cited

U.S. PATENT DOCUMENTS

| | | | |
|---|---|---|---|
| 5,104,442 A | 4/1992 | Schutze et al. | |
| 6,395,766 B1 | 5/2002 | Broughton et al. | |
| 7,358,370 B2* | 4/2008 | Huang ................ | C07D 209/08 548/360.1 |
| 9,656,956 B2* | 5/2017 | Huang ................ | C07D 209/08 |
| 2013/0190509 A1 | 7/2013 | Wang et al. | |
| 2015/0329493 A1 | 11/2015 | Hall | |

FOREIGN PATENT DOCUMENTS

| | | |
|---|---|---|
| CN | 1896060 A | 1/2007 |
| CN | 101273991 A | 10/2008 |
| CN | 103784437 A | 5/2014 |
| WO | 2006/133634 A1 | 12/2006 |
| WO | 2007/101156 A1 | 9/2007 |
| WO | WO-2007107539 A1 * | 9/2007 ........... C07D 231/56 |
| WO | 2008/110566 A1 | 9/2008 |
| WO | WO 2008130879 A2 * | 10/2008 ........... C07D 231/56 |
| WO | 2009/114470 A2 | 9/2009 |
| WO | 2012/123823 A1 | 9/2012 |

OTHER PUBLICATIONS

U.S. Appl. No. 14/952,421, filed Nov. 2015, Esanex et al.*
Liu et al. Xenobiotica, 2014, 44, 455-464.*
Chemical Abstract Service STN Registry No. 1551874-51-1 [entered STN: Feb. 21, 2014].*
PubChem Database [online] CID 2213682 [Deposit date: Jul. 12, 2007] (Year: 2007).*
The International Search Report (ISR) with Written Opinion for PCT/US2015/049696 dated Nov. 3, 2015, pp. 1-11.
Database CA {Online} Chemical Abstracts Services (Nov. 5, 2013), Liu, Wei et al., "Metabolite elucidation of the Hsp90 Inhibitor SNX-2112 using ultraperformance liquid chromatography/ quadrupole time-of-flight mass spectrometry (UPLC-QTOF/MS)", XP002746813, Database accession No. 2014:560823 compound: RN—1621991-44-3.
Database CA {Online} Chemical Abstracts Services (Feb. 26, 2015), Blaquiere, Nicole et al., "Alkynyl alcohols as NIK Inhibitors and their preparation", XP002746812, retrieved from STN Database accession No. 2015:335897 compounds with rn Nos. rn 1658467-32-3 and rn 1658467-33-4.

* cited by examiner

*Primary Examiner* — Amanda L Aguirre
(74) *Attorney, Agent, or Firm* — McDonnell Boehnen Hulbert & Berghoff LLP

(57) ABSTRACT

The invention relates to indazolylbenzamide, indolylbenzamide, benzo[d]imidazolyl-benzamide, and benzo[d]triazolylbenzamide derivatives of formula

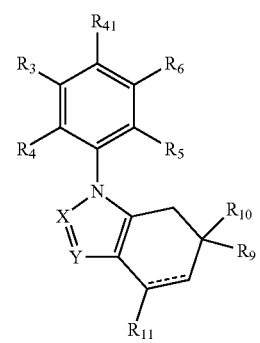

useful in the treatment and/or prevention of diseases and/or conditions related to cell proliferation, such as cancer, infection, inflammation and inflammation-associated disorders, and conditions associated with angiogenesis.

21 Claims, No Drawings

INDAZOLYL- AND INDOLYL-BENZAMIDE DERIVATIVES

CROSS-REFERENCE TO RELATED APPLICATIONS

This application claims priority to U.S. Provisional Application No. 62/049,152, filed Sep. 11, 2014, the disclosure of which is hereby incorporated by reference in its entirety.

BACKGROUND OF THE INVENTION

Field of the Invention

The invention relates to indazolylbenzamide, indolylbenzamide, benzo[d]imidazolylbenzamide, and benzo[d]triazolylbenzamide derivatives and more specifically to such compounds that are useful in the treatment and/or prevention of diseases and/or conditions related to cell proliferation, such as cancer, inflammation and inflammation-associated disorders, and conditions associated with angiogenesis. Compounds of the invention are also useful in the treatment and/or prevention of infectious diseases.

Description of Related Art

Cancer is characterized by abnormal cellular proliferation. Cancer cells exhibit a number of properties that make them dangerous to the host, typically including an ability to invade other tissues and to induce capillary ingrowth, which assures that the proliferating cancer cells have an adequate supply of blood. A hallmark of cancerous cells is their abnormal response to control mechanisms that regulate cell division in normal cells and continue to divide until they ultimately kill the host.

Angiogenesis is a highly regulated process under normal conditions, however many diseases are driven by persistent unregulated angiogenesis. Unregulated angiogenesis may either cause a particular disease directly or exacerbate an existing pathological condition. For example, ocular neovascularization has not only been implicated as the most common cause of blindness, but also is believed the dominant cause of many eye diseases. Further, in certain existing conditions, for example arthritis, newly formed capillary blood vessels invade the joints and destroy cartilage, or in the case of diabetes, new capillaries formed in the retina invade the vitreous, bleed, and cause blindness. Growth and metastasis of solid tumors are also dependent on angiogenesis (Folkman, J., Cancer Research, 46, 467-473 (1986), Folkman, J., Journal of the National Cancer Institute, 82, 4-6 (1989). It has been shown, for example, that tumors which enlarge to greater than 2 mm must obtain their own blood supply and do so by inducing the growth of new capillary blood vessels. Once these new blood vessels become embedded in the tumor, they provide a means for tumor cells to enter the circulation and metastasize to distant sites such as liver, lung or bone (Weidner, N., et al., The New England Journal of Medicine, 324(1), 1-8 (1991). Under conditions of unregulated angiogenesis, therapeutic methods designed to control, repress, and/or inhibit angiogenesis could lead to the abrogation or mitigation of these conditions and diseases.

Inflammation is related to a variety of disorders such as pain, headaches, fever, arthritis, asthma, bronchitis, menstrual cramps, tendonitis, bursitis, psoriasis, eczema, burns, dermatitis, inflammatory bowel syndrome, Crohn's disease, gastritis, irritable bowel syndrome, ulcerative colitis, vascular diseases, Hodgkin's disease, sclerodoma, rheumatic fever, type I diabetes, myasthenia gravis, sarcoidosis, nephrotic syndrome, Behcet's syndrome, polymyositis, hypersensitivity, conjunctivitis, gingivitis, post-injury swelling, myocardial ischemia, and the like.

Heat-shock protein 90 (HSP-90) is a cellular chaperone protein required for the activation of several eukaryotic protein kinases, including the cyclin-dependent kinase CDK4. Geldanamycin, an inhibitor of the protein-refolding activity of HSP-90, has been shown to have antiproliferative and antitumor activities.

HSP-90 is a molecular chaperone that guides the normal folding, intracellular disposition and proteolytic turnover of many key regulators of cell growth and survival. Its function is subverted during oncogenesis to make malignant transformation possible and to facilitate rapid somatic evolution, and to allow mutant proteins to retain or even gain function. Inhibition of HSP-90 will slow those processes thus has potential therapeutic use (Whitesell L, Lindquist, S L, Nature Rev. Cancer, 2005, 10, 761-72).

Ansamycin antibiotics, e.g., herbimycin A (HA), geldanamycin (GM), and 17-allylaminogeldanamycin (17-AAG) are thought to exert their anticancerous effects by tight binding of the N-terminus pocket of HSP-90, thereby destabilizing substrates that normally interact with HSP-90 (Stebbins, C. et al. Cell 1997, 89, 239-250). This pocket is highly conserved and has weak homology to the ATP-binding site of DNA gyrase (Stebbins, C. et al., supra; Grenert, J. P. et al. J. Biol. Chem. 1997, 272, 23843-50).

In vitro and in vivo studies have demonstrated that occupancy of this N-terminal pocket by ansamycins and other HSP-90 inhibitors alters HSP-90 function and inhibits protein folding. At high concentrations, ansamycins and other HSP-90 inhibitors have been shown to prevent binding of protein substrates to HSP-90 (Scheibel, T. H. et al. Proc. Natl. Acad. Sci. USA 1999, 96, 1297-302; Schulte, T. W. et al. J. Biol. Chem. 1995, 270, 24585-8; Whitesell, L., et al. Proc. Natl. Acad. Sci. USA 1994, 91, 8324-8328). Ansamycins have also been demonstrated to inhibit the ATP-dependent release of chaperone-associated protein substrates (Schneider, C. L. et al. Proc. Natl. Acad. Sci., USA 1996, 93, 14536-41; Sepp-Lorenzino et al. J. Biol Chem. 1995, 270, 16580-16587). In either event, the substrates are degraded by a ubiquitin-dependent process in the proteasome (Schneider, C. L., et al.; Sepp-Lorenzino, L., et al. J. Biol. Chem. 1995, 270, 16580-16587; Whitesell, L. et al. Proc. Natl. Acad. Sci. USA 1994, 91, 8324-8328). HSP-90 substrate destabilization occurs in tumor and non-transformed cells alike and has been shown to be especially effective on a subset of signaling regulators, e.g., Raf (Schulte, T. W. et al., Biochem. Biophys. Res. Commun. 1997, 239, 655-9; Schulte, T. W., et al., J. Biol. Chem. 1995, 270, 24585-8), nuclear steroid receptors (Segnitz, B.; U. Gehring J. Biol. Chem. 1997, 272, 18694-18701; Smith, D. F. et al. Mol. Cell Biol. 1995, 15, 6804-12), v-Src (Whitesell, L., et al. Proc. Natl. Acad. Sci. USA 1994, 91, 8324-8328) and certain transmembrane tyrosine kinases (Sepp-Lorenzino, L. et al. J. Biol. Chem. 1995, 270, 16580-16587) such as EGF receptor (EGFR) and HER2/Neu (Hartmann, F., et al. Int. J. Cancer 1997, 70, 221-9; Miller, P. et al. Cancer Res. 1994, 54, 2724-2730; Mimnaugh, E. G., et al. J. Biol. Chem. 1996, 271, 22796-801; Schnur, R. et al. J. Med. Chem. 1995, 38, 3806-3812), CDK4, and mutant p53. Erlichman et al. Proc. AACR 2001, 42, abstract 4474. The ansamycin-induced loss of these proteins leads to the selective disruption of certain regulatory pathways and results in growth arrest at specific phases of the cell cycle (Muise-Heimericks, R. C. et al. J. Biol. Chem. 1998, 273, 29864-72), and apoptosis, and/or differentiation of cells so treated (Vasilevskaya, A. et al. Cancer Res., 1999, 59, 3935-40). Inhibitors of HSP-90 thus hold great promise for the treatment and/or prevention of many types of cancers and proliferative disorders, and also hold promise as traditional antibiotics.

Inhibition of HSP-90 is also known to result in up regulation of the expression of the chaperone HSP70. HSP70 up regulation is considered to be of therapeutic benefit for treatment of a wide range of neurodegenerative diseases including, but not limited to: Alzheimer's disease; Parkinson's disease; Dementia with Lewy bodies; Amyotrophic Lateral Sclerosis (ALS); Polyglutamine disease; Huntington's disease; Spinal and bulbar muscular atrophy (SBMA); and Spinocerebellar ataxias (SCA1-3,7) (Muchowski, P. J., Wacker J. L., *Nat. Rev. Neurosci.* 2005, 6, 11-22; Shen H. Y., et al. *J. Biol. Chem.* 2005, 280, 39962-9).

Inhibition of HSP-90 also has antifungal activity, both as stand-alone therapy and in combination with standard antifungal therapies such as the azole class of drugs (Cowen, L. E., Lindquist, S, *Science* 2005, 309, 2185-9).

Inhibition of HSP-90 also produces antimalarial activity. In addition, HSP-90 is nearly universally required for viral protein homeostasis. Hsp90 inhibitors have been demonstrated to possess antiviral activity in tissue culture against picornaviruses (poliovirus, coxsackievirus, rhinovirus), influenza virus, paramyxoviruses (HPIV2, HPIV3, SV5, SV41), hepatitis C (HCV), hepatitis B (HBV), ebola (EBOV), vesicular stomatitis virus, La crosse virus, severe acquired respiratory syndrome (SARS), Feline herpesvirus (FHV), Human Immunodeficiency Virus Type 1 (HIV), vaccinia virus, and herpes viruses (HSV1/2, HCMV, VZV). (Geller, R, et al. *Biochim. Biophys. Acta* 2012, 1823, 698-706; Smith, D R et al. *Antiviral Res.* 2010, 87(2), 187-194).

SUMMARY OF THE INVENTION

There is a continuing need in the art for new methods of treating cancer, infections, inflammation and inflammation-associated disorders, and conditions or diseases related to uncontrolled angiogenesis. Thus, in a broad aspect, the invention encompasses the compounds of formula I shown below, pharmaceutical compositions containing those compounds. The compounds and compositions of the disclosure significantly inhibit HSP90 and cell-proliferation, and are useful in methods employing such compounds or compositions in the treatment of diseases and/or conditions related to cell proliferation, such as cancer, inflammation, arthritis, angiogenesis, or the like In embodiment 1, the invention provides compounds of formula I,

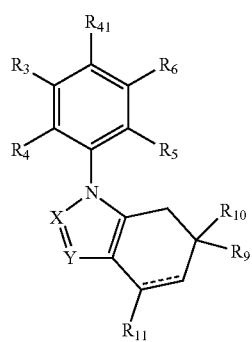

I or pharmaceutically acceptable salts thereof, wherein bond "≡" is a single or a double bond;

$R_3$ is hydrogen, halogen, cyano, —C(O)OH, —C(O)—O ($C_1$-$C_6$ alkyl), —N($R_N$)$_2$, $C_1$-$C_6$ alkyl, $C_1$-$C_6$ alkoxy, $C_1$-$C_6$ haloalkyl, $C_3$-$C_7$ cycloalkyl, aryl, or heteroaryl, wherein;
  each alkyl, cycloalkyl, aryl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo ($C_1$-$C_6$)alkyl, halo($C_1$-$C_6$)alkoxy, or carboxamide; and
  each $R_N$ is independently hydrogen or —$C_1$-$C_6$ alkyl-;
$R_4$ and $R_5$ are independently hydrogen or halogen;
$R_6$ is halogen, or a $C_1$-$C_{15}$ alkyl group where up to six of the carbon atoms in said alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein
  $R_{22}$ is heteroaryl, aryl, saturated or unsaturated $C_3$-$C_{10}$ cycloalkyl, or saturated or unsaturated $C_2$-$C_{10}$ heterocycloalkyl, wherein each aryl, heteroaryl, saturated or unsaturated cycloalkyl, or saturated or unsaturated heterocycloalkyl, independently, is optionally substituted with at least one group, which independently is hydroxy, halo, amino, cyano, carboxy, carboxamido, nitro, oxo,
    —S—($C_1$-$C_6$)alkyl, —$SO_2$—($C_1$-$C_6$)alkyl, —$SO_2$-aryl, —SO—($C_1$-$C_6$)alkyl, —SO-aryl,
    —$SO_2NH_2$, —$SO_2NH$—($C_1$-$C_6$)alkyl, —$SO_2NH$-aryl, ($C_1$-$C_6$)alkoxy, or mono- or di-($C_1$-$C_{10}$)alkylamino;
    and wherein each is optionally fused to a $C_6$-$C_{10}$ aryl group, $C_5$-$C_8$ saturated cyclic group, or a $C_5$-$C_{10}$ heterocycloalkyl group;
  and wherein $R_6$ group is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$, wherein
    Z is $OR_{31}$ or —N($R_{30}$)$_2$, wherein
      each $R_{30}$ is independently hydrogen or $C_1$-$C_6$ alkyl, or N($R_{30}$)$_2$ represents pyrrolidinyl, piperidinyl, piperazinyl, azepanyl, 1,3- or 1,4-diazepanyl, or morpholinyl, each of which is optionally substituted with hydroxy, amino, aminoalkyl, $C_1$-$C_6$ alkyl, mono- or di($C_1$-$C_6$) alkylamino, $C_1$-$C_6$ alkoxy, or halogen;
      $R_{31}$ is hydrogen, $C_1$-$C_{10}$ alkyl, $C_2$-$C_{10}$ alkenyl, $C_2$-$C_{10}$ alkynyl, aryl, heteroaryl, or $C_1$-$C_6$ acyl;
      $R_{23}$ is heteroaryl, aryl, saturated or unsaturated $C_5$-$C_{10}$ cycloalkyl, or saturated or unsaturated $C_5$-$C_{10}$ heterocycloalkyl, and each is optionally substituted at least one group which is independently hydroxy, oxo, halo, amino, cyano, nitro, —SH, —S—($C_1$-$C_6$)alkyl, —$SO_2$—($C_1$-$C_6$)alkyl, —$SO_2$-aryl, —SO—($C_1$-$C_6$)alkyl, —SO-aryl, —$SO_2NH_2$, —$SO_2NH$—($C_1$-$C_6$)alkyl, —$SO_2NH$-aryl, $C_1$-$C_6$ alkoxy, or mono- or di-($C_1$-$C_{10}$)alkylamino;
$R_9$ and $R_{10}$ are independently hydrogen or $C_1$-$C_8$ alkyl; or $R_9$ and $R_{10}$ taken together with the carbon atom to which they are attached form $C_3$-$C_8$ cycloalkyl;
$R_{11}$ is hydrogen, hydroxy, $C_1$-$C_{10}$ alkyl, $C_2$-$C_{10}$ alkenyl, $C_2$-$C_{10}$ alkynyl, $C_1$-$C_{10}$ haloalkyl, $C_1$-$C_{10}$ alkoxy, monoor di-($C_1$-$C_{10}$)alkylamino, $C_1$-$C_{10}$ alkoxy($C_1$-$C_{10}$)alkyl, hydroxy($C_1$-$C_{10}$) alkoxy, or amino($C_1$-$C_{10}$) alkoxy;

$R_{41}$ is cyano or a group of the formula

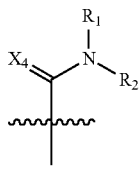

wherein $R_1$ and $R_2$ are independently H, hydroxy, $C_1$-$C_6$ alkyl, $C_2$-$C_6$ alkenyl, $C_2$-$C_6$ alkynyl, heteroaryl, aryl, $C_3$-$C_8$ cycloalkyl, heterocycloalkyl, wherein each alkyl, cycloalkyl, heterocycloalkyl, aryl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, nitro, halo($C_1$-$C_6$)alkyl, halo($C_1$-$C_6$) alkoxy, or carboxamide;

$X_4$ is oxygen or sulfur;

X is N or $CR_C$; and

Y is N or $CR_C$;

each $R_C$ is independently is hydrogen, halogen, cyano, nitro, —C(O)$R_{C1}$, $C_1$-$C_{10}$ alkyl, $C_2$-$C_{10}$ alkenyl, $C_2$-$C_{10}$ alkynyl, $C_1$-$C_{10}$ haloalkyl, $C_3$-$C_7$ cycloalkyl, $C_3$-$C_7$ cycloalkyl($C_1$-$C_{10}$)alkyl, heterocycloalkyl, aryl, or heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, cyano, nitro, halo($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, halo($C_1$-$C_6$)alkyl, or carboxamide;

$R_{C1}$ is —$C_1$-$C_6$ alkyl, —$OR_{C2}$, or —$N(R_{CN})_2$, wherein $R_{C2}$ is —H, $C_1$-$C_{10}$ alkyl, $C_1$-$C_{10}$ haloalkyl, $C_3$-$C_7$ cycloalkyl, heterocycloalkyl, aryl, or heteroaryl;

each $R_{CN}$ is independently —H, $C_1$-$C_{10}$ alkyl, $C_1$-$C_{10}$ haloalkyl, $C_3$-$C_7$ cycloalkyl, heterocycloalkyl, $C_1$-$C_6$ acyl, aryl, or heteroaryl, wherein each alkyl, cycloalkyl, heterocycloalkyl, aryl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, nitro, halo($C_1$-$C_6$)alkyl, halo($C_1$-$C_6$)alkoxy, or carboxamide.

The invention also includes intermediates that are useful in making the compounds of the invention.

The invention also provides pharmaceutical compositions comprising a compound or pharmaceutically acceptable salt of Formula I and at least one pharmaceutically acceptable carrier, solvent, adjuvant or diluent.

The invention further provides methods of treating disease such as cancer, inflammation, arthritis, angiogenesis, and infection in a patient in need of such treatment, comprising administering to the patient a compound or pharmaceutically acceptable salt of Formula I, or a pharmaceutical composition comprising a compound or salt of Formula I.

The invention also provides the use of a compound or salt according to Formula I for the manufacture of a medicament for use in treating cancer, inflammation, arthritis, angiogenesis, or infection.

The invention also provides methods of preparing the compounds of the invention and the intermediates used in those methods.

The invention also provides methods of treating a disease or condition related to cell proliferation comprising administering a therapeutically effective amount of a compound or salt of Formula I to a patient in need of such treatment.

The invention also provides methods of treating a disease or condition related to cell proliferation comprising administering a therapeutically effective amount of a compound or salt of Formula I to a patient in need of such treatment, where the disease of condition is cancer, inflammation, infection, or arthritis.

The invention further provides methods of treating a subject suffering from a disease or disorder of proteins that are either client proteins for HSP-90 or indirectly affect its client proteins, comprising administering to a subject in need of such treatment a therapeutically effective amount of a compound or salt of Formula I.

The invention further provides a compound or pharmaceutical composition thereof in a kit with instructions for using he compound or composition.

The invention further provides compounds that may be administered alone or in combination with other drugs or therapies known to be effective to treat the disease to enhance overall effectiveness of therapy.

DETAILED DESCRIPTION OF THE INVENTION

Before the disclosed methods and compositions are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

In view of the present disclosure, the compositions described herein can be configured by the person of ordinary skill in the art to meet the desired need. In general, the disclosed compositions provide improvements in. For example, in certain aspects, the compositions and methods of the disclosure exhibit potent anti-cancer activity.

Particular compounds of Embodiment 1 include those of Embodiment 2, i.e., compounds where $R_{41}$ is —C(O) $NR_1R_2$.

In embodiment 3, the disclosure provides compounds of Embodiment 1 or 2 wherein $R_6$ is —$Z_1R_{Z1}$, and wherein $Z_1$ is —O—, —NH—, —S(O)$_p$—, or —S(O)$_2$NH—, wherein p is 0, 1 or 2; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, and wherein $R_{Z1}$ is optionally substituted at any available position independently with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

In a particular aspect of Embodiment 3, Embodiment 4, $Z_1$ is —O— or —NH—. In another particular aspect of Embodiment 3, Embodiment 5, $Z_1$ is —NH—.

Particular embodiments based on any of Embodiments 1-5 include those of Embodiment 6, i.e., compounds having the formula I-1

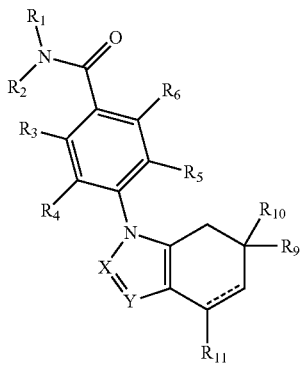

I-1 wherein $R_6$ is —N$R_7R_8$, wherein $R_7$ is ($C_1$-$C_{14}$)alkyl, ($C_2$-$C_{14}$)alkenyl, ($C_2$-$C_{14}$)alkynyl, aryl, aryl($C_1$-$C_8$)alkyl, ($C_3$-$C_8$)cycloalkenyl, ($C_3$-$C_8$)cycloalkenyl($C_1$-$C_8$)alkyl, ($C_3$-$C_8$)cycloalkyl, ($C_3$-$C_8$)cycloalkyl($C_1$-$C_8$)alkyl, heteroaryl, heteroaryl($C_1$-$C_8$)alkyl, heteroaryl($C_1$-$C_8$)alkylthio($C_1$-$C_8$)alkyl, heteroarylthio($C_1$-$C_8$)alkyl, heterocyclyl, heterocycle($C_1$-$C_8$)alkyl, or hydroxy($C_1$-$C_8$)alkyl, wherein each is optionally substituted with 1, 2, 3, 4, or 5 groups which are independently ($C_2$-$C_8$)alkenyl, ($C_1$-$C_8$)alkoxy, ($C_1$-$C_8$)alkoxy($C_1$-$C_8$)alkyl, ($C_1$-$C_8$)alkoxycarbonyl, ($C_1$-$C_8$)alkyl, ($C_1$-$C_8$)alkylcarbonyl, ($C_1$-$C_8$)alkylcarbonyloxy, ($C_1$-$C_8$)alkylsulfinyl, ($C_1$-$C_8$)alkylsulfonyl, ($C_1$-$C_8$)alkylthio, ($C_2$-$C_8$)alkynyl, carboxy, carboxy($C_1$-$C_8$)alkyl, cyano, cyano($C_1$-$C_8$)alkyl, ($C_3$-$C_8$)cycloalkyl, ($C_3$-$C_8$)cycloalkyl($C_1$-$C_8$)alkyl, formyl, halo($C_1$-$C_8$)alkoxy, halo($C_1$-$C_8$)alkyl, halogen, hydroxy, hydroxy($C_1$-$C_8$)alkoxy, hydroxy($C_1$-$C_8$)alkoxy($C_1$-$C_8$)alkoxy, hydroxy($C_1$-$C_8$)alkyl, mercapto, nitro, —N$R_{12}R_{13}$, (N$R_{12}R_{13}$)($C_1$-$C_8$)alkyl, (N$R_{12}R_{13}$)carbonyl, oxo, HOC$H_2$CH(N$H_2$)C(O)O—, N$H_2$(C$H_2$)$_m$C(O)O—, C$H_3$NH(C$H_2$)$_m$C(O)O—, (C$H_3$)$_2$N(C$H_2$)$_m$C(O)O—, N$H_2$(C$H_2$)$_t$C(O)NH(C$H_2$)$_m$C(O)O—, $R_{13}$CH(N$H_2$)C(O)O—, N$H_2$(C$H_2$)$_m$C($R_{13}$)$_2$(C$H_2$)$_m$C(O)O—, N$H_2$C$H_2$C$H_2$C(O)O—, $R_{12}$ON=CH(C$H_2$)$_n$O—, HONHC(O)(C$H_2$)$_n$O—, —OP(O)(O$R_P$)$_2$, —OS(O)$_2$O$R_S$, or $R_{20}$;

where each m is independently 1, 2, 3, or 4;
where each n is 1, 2, 3, 4, 5, or 6;
where t is 1, 2, 3, or 4;
where $R_{12}$ and $R_{13}$ are independently —H, ($C_2$-$C_8$)alkenyl, ($C_1$-$C_8$)alkyl, ($C_1$-$C_8$)alkylcarbonyl, ($C_2$-$C_8$)alkynyl, aryl, aryl($C_1$-$C_8$)alkyl, ($C_3$-$C_8$)cycloalkyl, ($C_3$-$C_8$)cycloalkyl($C_1$-$C_8$)alkyl, formyl, heteroaryl, heteroaryl($C_1$-$C_8$)alkyl, heterocyclyl, or heterocycle($C_1$-$C_8$)alkyl; or two $R_{12}$ groups together with the carbon to which they are attached form a ($C_3$-$C_8$)cycloalkyl group;
where each $R_P$ and $R_S$ are independently hydrogen, ($C_1$-$C_6$)alkyl, ($C_1$-$C_6$)haloalkyl, or aryl, wherein the alkyl or aryl is optionally substituted with one or more groups independently selected from ($C_1$-$C_6$) alkyl, ($C_1$-$C_6$)alkoxy, halogen, hydroxy, amino, mono- or di-($C_1$-$C_6$)alkylamino, nitro, halo($C_1$-$C_6$) alkyl, carboxy, or carboxamide;

where $R_{20}$ is:

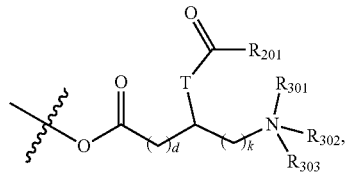

wherein d and k are integers independently selected from 1 and 2;

$R_{201}$ is ($C_1$-$C_6$)alkyl where the alkyl is optionally substituted with ($C_3$-$C_7$)cycloalkyl, ($C_2$-$C_6$) alkenyl, ($C_2$-$C_6$)alkynyl, hydroxy, halogen, nitro, or cyano; and T is O or N$R_{202}$ where $R_{202}$ is hydrogen or ($C_1$-$C_6$) alkyl; and $R_{301}$ and $R_{302}$ are independently hydrogen or ($C_1$-$C_6$)alkyl, and $R_{303}$ is absent, hydrogen, or ($C_1$-$C_6$)alkyl; and $R_8$ is hydrogen or ($C_1$-$C_8$)alkyl.

Embodiment 7 encompasses compounds of any of Embodiments 2-6 wherein $R_1$ and $R_2$ are independently hydrogen or methyl. Yet another embodiment of the invention, i.e., Embodiment 8, encompasses compounds of any of Embodiments 2-6 wherein $R_1$ and $R_2$ are independently hydrogen.

Particular compounds of Embodiment 1 include those of Embodiment 9, i.e., compounds where $R_{41}$ is cyano.

In embodiment 10, the disclosure provides compounds of Embodiment 9 wherein $R_6$ is —$Z_1R_{Z1}$, $Z_1$ is —O—, —NH—, —S(O)$_p$—, or —S(O)$_2$NH—, wherein p is 0, 1 or 2; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, SO$_2$, or SO, with the proviso that two O atoms, two S atoms, or an O and S atom are not immediately adjacent each other, and wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —SO$_2$—($C_1$-$C_6$)alkyl, —SO$_2$NH$_2$, —SO$_2$NH—($C_1$-$C_6$)alkyl, —SO$_2$NH-aryl, —SO$_2$-aryl, —SO—($C_1$-$C_6$)alkyl, —SO$_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

In a particular aspect of Embodiment 10, Embodiment 11, $Z_1$ is —O— or —NH—. In another particular aspect of Embodiment 10, Embodiment 12, $Z_1$ is —NH—.

Particular embodiments based on any of Embodiments 9-12 include those of Embodiment 13, having the formula I-1

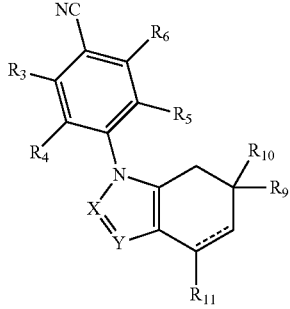

I-2 wherein
R$_6$ is —NR$_7$R$_8$, wherein
R$_7$ is (C$_1$-C$_{14}$)alkyl, (C$_2$-C$_{14}$)alkenyl, (C$_2$-C$_{14}$)alkynyl, aryl, aryl(C$_1$-C$_8$)alkyl, (C$_3$-C$_8$)cycloalkenyl, (C$_3$-C$_8$)cycloalkenyl(C$_1$-C$_8$)alkyl, (C$_3$-C$_8$)cycloalkyl, (C$_3$-C$_8$)cycloalkyl(C$_1$-C$_8$)alkyl, heteroaryl, heteroaryl(C$_1$-C$_8$)alkyl, heteroaryl(C$_1$-C$_8$)alkylthio(C$_1$-C$_8$)alkyl, heteroarylthio(C$_1$-C$_8$)alkyl, heterocyclyl, heterocycle(C$_1$-C$_8$)alkyl, or hydroxy(C$_1$-C$_8$)alkyl,
wherein each is optionally substituted with 1, 2, 3, 4, or 5 groups which are (C$_2$-C$_8$)alkenyl, (C$_1$-C$_8$)alkoxy, (C$_1$-C$_8$)alkoxy(C$_1$-C$_8$)alkyl, (C$_1$-C$_8$)alkoxycarbonyl, (C$_1$-C$_8$)alkyl, (C$_1$-C$_8$)alkylcarbonyl, (C$_1$-C$_8$)alkylcarbonyloxy, (C$_1$-C$_8$)alkylsulfinyl, (C$_1$-C$_8$)alkylsulfonyl, (C$_1$-C$_8$)alkylthio, (C$_2$-C$_8$)alkynyl, carboxy, carboxy(C$_1$-C$_8$)alkyl, cyano, cyano(C$_1$-C$_8$)alkyl, (C$_3$-C$_8$)cycloalkyl, (C$_3$-C$_8$)cycloalkyl(C$_1$-C$_8$)alkyl, formyl, halo(C$_1$-C$_8$)alkoxy, halo(C$_1$-C$_8$)alkyl, halogen, hydroxy, hydroxy(C$_1$-C$_8$)alkoxy, hydroxy(C$_1$-C$_8$)alkoxy(C$_1$-C$_8$)alkoxy, hydroxy(C$_1$-C$_8$)alkyl, mercapto, nitro, —NR$_{12}$R$_{13}$, (NR$_{12}$R$_{13}$)(C$_1$-C$_8$)alkyl, (NR$_{12}$R$_{13}$)carbonyl, oxo, HOCH$_2$CH(NH$_2$)C(O)O—, NH$_2$(CH$_2$)$_m$C(O)O—, CH$_3$NH(CH$_2$)$_m$C(O)O—, (CH$_3$)$_2$N(CH$_2$)$_m$C(O)O—, NH$_2$(CH$_2$)$_t$C(O)NH(CH$_2$)$_m$C(O)O—, R$_{13}$CH(NH$_2$)C(O)O—, NH$_2$(CH$_2$)$_m$C(R$_{13}$)$_2$(CH$_2$)$_m$C(O)O—, NH$_2$CH$_2$CH$_2$C(O)O—, R$_{12}$ON═CH(CH$_2$)$_n$O—, HONHC(O)(CH$_2$)$_n$O—, —OP(O)(OR$_P$)$_2$, —OS(O)$_2$OR$_S$, or R$_{20}$;
where each m is independently 1, 2, 3, or 4;
where each n is 1, 2, 3, 4, 5, or 6;
where t is 1, 2, 3, or 4;
where R$_{12}$ and R$_{13}$ are independently —H, (C$_2$-C$_8$)alkenyl, (C$_1$-C$_8$)alkyl, (C$_1$-C$_8$)alkylcarbonyl, (C$_2$-C$_8$)alkynyl, aryl, aryl(C$_1$-C$_8$)alkyl, (C$_3$-C$_8$)cycloalkyl, (C$_3$-C$_8$)cycloalkyl(C$_1$-C$_8$)alkyl, formyl, heteroaryl, heteroaryl(C$_1$-C$_8$)alkyl, heterocyclyl, or heterocycle(C$_1$-C$_8$)alkyl; or two R$_{12}$ groups together with the carbon to which they are attached form a (C$_3$-C$_8$)cycloalkyl group;
where each R$_P$ and R$_S$ are independently hydrogen, (C$_1$-C$_6$)alkyl, (C$_1$-C$_6$)haloalkyl, or aryl, wherein the alkyl or aryl is optionally substituted with one or more groups independently selected from (C$_1$-C$_6$)alkyl, (C$_1$-C$_6$)alkoxy, halogen, hydroxy, amino, mono- or di-(C$_1$-C$_6$)alkylamino, nitro, halo(C$_1$-C$_6$)alkyl, carboxy, or carboxamide;

where R$_{20}$ is:

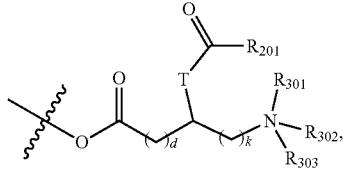

wherein
d and k are integers independently selected from 1 and 2;
R$_{201}$ is (C$_1$-C$_6$)alkyl where the alkyl is optionally substituted with (C$_3$-C$_7$)cycloalkyl, (C$_2$-C$_6$) alkenyl, (C$_2$-C$_6$)alkynyl, hydroxy, halogen, nitro, or cyano; and
T is O or NR$_{202}$ where R$_{202}$ is hydrogen or (C$_1$-C$_6$) alkyl; and
R$_{301}$ and R$_{302}$ are independently hydrogen or (C$_1$-C$_6$)alkyl, and
R$_{303}$ is absent, hydrogen, or (C$_1$-C$_6$)alkyl; and
R$_8$ is hydrogen or (C$_1$-C$_8$)alkyl.

Another embodiment of the invention, i.e., Embodiment 14, encompasses compounds of any of Embodiments 1-13 where Y is N.

In Embodiment 15 the invention encompasses compounds of any of Embodiments 1-13 where Y is CR$_C$. In Embodiment 16, the invention encompasses compounds of Embodiment 15 wherein R$_C$ is hydrogen, halogen, C$_1$-C$_{10}$ alkyl, C$_2$-C$_{10}$ alkenyl, C$_2$-C$_{10}$ alkynyl, C$_1$-C$_{10}$ haloalkyl, C$_3$-C$_7$ cycloalkyl, C$_3$-C$_7$ cycloalkyl(C$_1$-C$_{10}$)alkyl, heterocycloalkyl, aryl, or heteroaryl, each optionally substituted. In Embodiment 17, which is based on Embodiment 15, the compounds are where R$_C$ is hydrogen, C$_1$-C$_{10}$ alkyl, C$_2$-C$_{10}$ alkenyl, C$_2$-C$_{10}$ alkynyl, or C$_1$-C$_{10}$ haloalkyl. Embodiment 18 provides compounds within Embodiment 17 where R$_C$ is hydrogen. Embodiment 19 provides compounds within Embodiment 17 where R$_C$ is C$_1$-C$_{10}$ alkyl, C$_2$-C$_{10}$ alkenyl, C$_2$-C$_{10}$ alkynyl, or C$_1$-C$_{10}$ haloalkyl. Particularly in Embodiment 19, R$_C$ is C$_1$-C$_6$ alkyl, C$_2$-C$_6$ alkenyl, C$_2$-C$_6$ alkynyl, or C$_1$-C$_6$ haloalkyl. Particularly in Embodiment 19, R$_C$ is C$_1$-C$_6$ alkyl or C$_1$-C$_6$ haloalkyl. More particularly in Embodiment 19, R$_C$ is methyl, ethyl, propyl, trifluoromethyl, difluoromethyl, or fluoromethyl. More particularly in Embodiment 19, R$_C$ is methyl, trifluoromethyl, difluoromethyl, or fluoromethyl.

Other particular embodiments include those of Embodiment 20, i.e., compounds of Embodiment 15 wherein R$_C$ is C$_1$-C$_{10}$ alkyl. Particularly in Embodiment 20, R$_C$ is C$_1$-C$_6$ alkyl. More particularly in Embodiment 20, R$_C$ is C$_1$-C$_4$ alkyl. Embodiment 21 provides compounds of Embodiment 15, where R$_C$ is methyl, ethyl, or propyl.

Other particular embodiments include those of Embodiment 22, i.e., compounds of Embodiment 15 wherein R$_C$ is methyl.

Another embodiment of the invention, Embodiment 23, encompasses compounds of any of Embodiments 1-22 where X is CR$_C$, and R$_C$ is hydrogen, C$_1$-C$_{10}$ alkyl, C$_2$-C$_{10}$ alkenyl, C$_2$-C$_{10}$ alkynyl, or C$_1$-C$_{10}$ haloalkyl. Particularly in Embodiment 23, R$_C$ is hydrogen, C$_1$-C$_6$ alkyl, or C$_1$-C$_6$ haloalkyl. In Embodiment 24, i.e., compounds of Embodiment 23, R$_C$ is hydrogen or C$_1$-C$_{10}$ alkyl. Particularly, the compounds of Embodiment 24 are wherein R$_C$ is hydrogen or C$_1$-C$_6$ alkyl. Embodiment 25 provides compounds of Embodiment 23, where R$_C$ is hydrogen.

Particular embodiments include those of Embodiment 26, i.e., compounds of any of Embodiments 1-22 where X is N.

Another embodiment of the invention, Embodiment 27, encompasses compounds of any of Embodiments 1-13 and 23-25 wherein the compounds are of formula I-1A or I-2A:

Another embodiment of the invention, i.e., Embodiment 30, encompasses compounds of any of embodiments 1-13 and 15-25, wherein the compounds are of formula I-1B or I-2B:

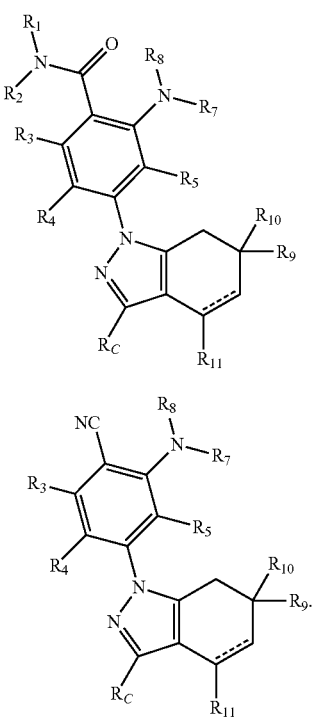

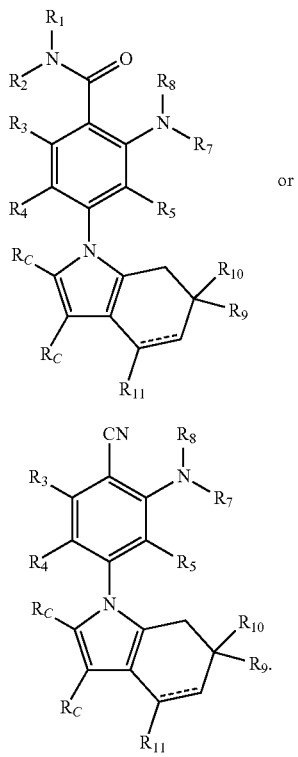

Embodiment 28 provides compounds of Embodiment 27 wherein $R_C$ is hydrogen, $C_1$-$C_{10}$ alkyl, or $C_1$-$C_{10}$ haloalkyl. Particularly in Embodiment 28, $R_C$ is hydrogen, $C_1$-$C_6$ alkyl, or $C_1$-$C_6$ haloalkyl. More particularly in Embodiment 28, $R_C$ is hydrogen or $C_1$-$C_6$ alkyl. More particularly in Embodiment 28, $R_C$ is $C_1$-$C_6$ alkyl. In Embodiment 29, which is based on embodiment 27, $R_C$ is methyl.

Particular compounds of the invention include those of Embodiment 27A, i.e., compounds of Embodiment 27 where $R_7$ is $(C_1$-$C_{14})$alkyl, $(C_3$-$C_8)$cycloalkenyl, $(C_3$-$C_8)$cycloalkyl, $(C_3$-$C_8)$cycloalkyl$(C_1$-$C_8)$alkyl, heteroaryl $(C_1$-$C_8)$alkylthio$(C_1$-$C_8)$alkyl, heteroaryl, heteroarylthio$(C_1$-$C_8)$alkyl, heterocyclyl, or hydroxy$(C_1$-$C_8)$ alkyl, wherein the $R_7$ group is optionally substituted with 1, 2, 3, or 4 groups that are $(C_2$-$C_8)$alkenyl, $(C_1$-$C_8)$ alkoxy, $(C_1$-$C_8)$alkoxy$(C_1$-$C_8)$alkyl, $(C_1$-$C_8)$alkoxycarbonyl, $(C_1$-$C_8)$alkyl, $(C_1$-$C_8)$alkylcarbonyl, $(C_2$-$C_8)$alkynyl, $(C_3$-$C_8)$cycloalkyl, $(C_3$-$C_8)$cycloalkyl$(C_1$-$C_8)$alkyl, hydroxy, hydroxy$(C_1$-$C_8)$alkoxy, hydroxy$(C_1$-$C_8)$alkoxy$(C_1$-$C_8)$alkoxy, hydroxy$(C_1$-$C_8)$alkyl, —$NR_{11}R_{12}$, $(NR_{11}R_{12})(C_1$-$C_8)$alkyl, oxo, $HOCH_2CH(NH_2)C(O)O$—, $NH_2(CH_2)_mC(O)O$—, $CH_3NH(CH_2)_mC(O)O$—, $(CH_3)_2N(CH_2)_mC(O)$ O—, $NH_2(CH_2)_tC(O)NH(CH_2)_mC(O)O$—, $R_{12}CH$ $(NH_2)C(O)O$—, $NH_2(CH_2)_mC(R_{12})_2(CH_2)_mC(O)$ O—, $NH_2CH_2CH_2C(O)O$—, $R_{11}ON$=$CH(CH_2)_n$ O—, or $HONHC(O)(CH_2)_nO$—;

Particularly, the compounds of Embodiment 30 are wherein each $R_C$ is independently hydrogen, $C_1$-$C_{10}$ alkyl, or $C_1$-$C_{10}$ haloalkyl. More particularly in Embodiment 30, each $R_C$ is independently hydrogen, $C_1$-$C_6$ alkyl, or $C_1$-$C_6$ haloalkyl. More particularly in Embodiment 30, each $R_C$ is independently hydrogen or $C_1$-$C_6$ alkyl. More particularly in Embodiment 30, each $R_C$ is independently $C_1$-$C_6$ alkyl. In Embodiment 31, which is based on Embodiment 30, the compounds are where each $R_C$ is hydrogen.

Particular embodiments include those of Embodiment 32, i.e., compounds of any of Embodiments 1-31, where $R_9$ and $R_{10}$ are independently hydrogen or $C_1$-$C_8$ alkyl. Other particular embodiments include those of Embodiment 33, i.e., compounds of any of Embodiments 1-31, where $R_9$ and $R_{10}$ are independently $C_1$-$C_8$ alkyl. Particularly in Embodiment 33, $R_9$ and $R_{10}$ are independently $C_1$-$C_6$ alkyl. In Embodiment 34, i.e., compounds of Embodiment 33, $R_9$ and $R_{10}$ are independently methyl. Another embodiment of the invention, Embodiment 35, encompasses compounds of any of Embodiments 1-31 where one of $R_9$ and $R_{10}$ is hydrogen and the other is $C_1$-$C_8$ alkyl, or one of $R_9$ and $R_{10}$ is hydrogen and the other is $C_1$-$C_6$ alkyl.

One embodiment of the disclosure, Embodiment 36, encompasses compounds of any of Embodiments 1-35 wherein bond "====" is a single bond.

One embodiment of the disclosure, Embodiment 37, encompasses compounds of any of Embodiments 1-35 wherein bond "====" is a double bond.

Particular embodiments include those of Embodiment 38, i.e., compounds of any of Embodiments 1-37, wherein $R_{11}$ is hydrogen, hydroxy, $C_1$-$C_{10}$ alkyl, $C_1$-$C_{10}$ haloalkyl, $C_1$-$C_{10}$ alkoxy, mono- or di-($C_1$-$C_{10}$)alkylamino, $C_1$-$C_{10}$ alkoxy($C_1$-$C_{10}$)alkyl, hydroxy($C_1$-$C_{10}$) alkoxy, or amino ($C_1$-$C_{10}$) alkoxy. Another embodiment include those of Embodiment 39, i.e., compounds of Embodiment 38, wherein $R_{11}$ is hydrogen, $C_1$-$C_{10}$ alkyl, hydroxy, $C_1$-$C_{10}$ alkoxy, mono- or di-($C_1$-$C_{10}$)alkylamino, $C_1$-$C_{10}$ alkoxy($C_1$-$C_{10}$)alkyl, hydroxy($C_1$-$C_{10}$) alkoxy, or amino($C_1$-$C_{10}$) alkoxy.

Another embodiment of the disclosure, Embodiment 40, encompasses compounds of any of Embodiments 1-37 where $R_{11}$ is hydrogen or $C_1$-$C_{10}$ alkyl. Particularly in Embodiment 40, $R_{11}$ is hydrogen or $C_1$-$C_6$ alkyl. Another embodiment includes those of Embodiment 41, i.e., compounds of Embodiment 40, wherein $R_{11}$ is hydrogen or methyl.

Particular embodiments include those of Embodiment 42, i.e., compounds of any of Embodiments 1-37, where $R_{11}$ is hydrogen. Other particular embodiments include those of Embodiment 43, i.e., compounds of any of Embodiments 1-37, where $R_{11}$ is methyl.

Particular embodiments of the disclosure include those of Embodiment 44, i.e., compounds of any of Embodiments 1-43, where $R_4$ and $R_5$ are independently hydrogen. Another embodiment includes Embodiment 45, i.e., compounds of Embodiment 1-43 wherein one of $R_4$ and $R_5$ is hydrogen and the other is halogen. Yet another embodiment of the disclosure includes Embodiment 46, i.e., compounds of Embodiment 1-43 wherein at least one of $R_4$ and $R_5$ is halogen if $R_3$ is not halogen.

One embodiment of the disclosure, i.e., Embodiment 47, encompasses compounds of any of Embodiments 1-46, wherein $R_3$ is hydrogen, halogen, cyano, —C(O)OH, —C(O)—O($C_1$-$C_6$ alkyl), —N($R_N$)$_2$, $C_1$-$C_6$ alkyl, $C_1$-$C_6$ alkoxy, or $C_1$-$C_6$ haloalkyl. Embodiment 48 encompasses compounds of any of Embodiments 1-46 where $R_3$ is hydrogen, halogen, cyano, —N($R_N$)$_2$, $C_1$-$C_6$ alkyl, $C_1$-$C_6$ alkoxy, or $C_1$-$C_6$ haloalkyl. Embodiment 49 encompasses compounds of any of Embodiments 1-46 where $R_3$ is hydrogen, halogen, $C_1$-$C_6$ alkoxy, or $C_1$-$C_6$ haloalkyl. Particular embodiments include those of Embodiment 50, i.e., compounds of any of Embodiments 1-46, wherein $R_3$ is halogen.

Particular embodiments of the disclosure include those of Embodiment 51, i.e., compounds of any of Embodiments 1-43 wherein $R_3$ is hydrogen, $R_4$ is hydrogen, and $R_5$ is hydrogen.

Another embodiment of the disclosure, i.e., Embodiment 52, encompasses compounds of any of Embodiments 6-8 and 13-51 wherein $R_7$ is ($C_1$-$C_{14}$)alkyl, ($C_2$-$C_{14}$)alkenyl, or ($C_2$-$C_{14}$)alkynyl, each is optionally substituted with 1, 2, 3, 4, or 5 groups which are ($C_2$-$C_8$)alkenyl, ($C_1$-$C_8$)alkoxy, ($C_1$-$C_8$)alkoxy($C_1$-$C_8$)alkyl, ($C_1$-$C_8$)alkoxycarbonyl, ($C_1$-$C_8$)alkyl, ($C_1$-$C_8$)alkylcarbonyl, ($C_1$-$C_8$)alkylcarbonyloxy, ($C_1$-$C_8$)alkylsulfinyl, ($C_1$-$C_8$)alkylsulfonyl, ($C_1$-$C_8$)alkylthio, ($C_2$-$C_8$)alkynyl, carboxy, carboxy($C_1$-$C_8$)alkyl, cyano, cyano($C_1$-$C_8$)alkyl, ($C_3$-$C_8$)cycloalkyl, ($C_3$-$C_8$)cycloalkyl($C_1$-$C_8$)alkyl, formyl, halo($C_1$-$C_8$)alkoxy, halo($C_1$-$C_8$)alkyl, halogen, hydroxy, hydroxy($C_1$-$C_8$)alkoxy, hydroxy($C_1$-$C_8$)alkoxy($C_1$-$C_8$)alkoxy, hydroxy($C_1$-$C_8$)alkyl, mercapto, nitro, —NR$_{12}$R$_{13}$, (NR$_{12}$R$_{13}$)($C_1$-$C_8$)alkyl, (NR$_{12}$R$_{13}$)carbonyl, oxo, HOCH$_2$CH(NH$_2$)C(O)O—, NH$_2$(CH$_2$)$_m$C(O)O—, CH$_3$NH(CH$_2$)$_m$C(O)O—, (CH$_3$)$_2$N(CH$_2$)$_m$C(O)O—, NH$_2$(CH$_2$)$_t$C(O)NH(CH$_2$)$_m$C(O)O—, R$_{13}$CH(NH$_2$)C(O)O—, NH$_2$(CH$_2$)$_m$C(R$_{13}$)$_2$(CH$_2$)$_m$C(O)O—, NH$_2$CH$_2$CH$_2$C(O)O—, R$_{12}$ON=CH(CH$_2$)$_n$O—, HONHC(O)(CH$_2$)$_n$O—, —OP(O)(OR$_P$)$_2$, —OS(O)$_2$OR$_S$, or R$_{20}$. Embodiment 53 encompasses compounds of any of Embodiments 6-8 and 13-51 wherein $R_7$ is $C_1$-$C_{14}$ alkyl, optionally substituted with 1, 2, 3, 4, or 5 groups which are ($C_2$-$C_8$)alkenyl, ($C_1$-$C_8$)alkoxy, ($C_1$-$C_8$)alkoxy($C_1$-$C_8$)alkyl, ($C_1$-$C_8$)alkoxycarbonyl, ($C_1$-$C_8$)alkyl, ($C_1$-$C_8$)alkylcarbonyl, ($C_1$-$C_8$)alkylcarbonyloxy, ($C_1$-$C_8$)alkylsulfinyl, ($C_1$-$C_8$)alkylsulfonyl, ($C_1$-$C_8$)alkylthio, ($C_2$-$C_8$)alkynyl, carboxy, carboxy($C_1$-$C_8$)alkyl, cyano, cyano($C_1$-$C_8$)alkyl, ($C_3$-$C_8$)cycloalkyl, ($C_3$-$C_8$)cycloalkyl($C_1$-$C_8$)alkyl, formyl, halo($C_1$-$C_8$)alkoxy, halo($C_1$-$C_8$)alkyl, halogen, hydroxy, hydroxy($C_1$-$C_8$)alkoxy, hydroxy($C_1$-$C_8$)alkoxy($C_1$-$C_8$)alkoxy, hydroxy($C_1$-$C_8$)alkyl, mercapto, nitro, —NR$_{12}$R$_{13}$, (NR$_{12}$R$_{13}$)($C_1$-$C_8$)alkyl, (NR$_{12}$R$_{13}$)carbonyl, oxo, HOCH$_2$CH(NH$_2$)C(O)O—, NH$_2$(CH$_2$)$_m$C(O)O—, CH$_3$NH(CH$_2$)$_m$C(O)O—, (CH$_3$)$_2$N(CH$_2$)$_m$ C(O)O—, NH$_2$(CH$_2$)$_t$C(O)—NH(CH$_2$)$_m$C(O)O—, R$_{13}$CH(NH$_2$)C(O)O—, NH$_2$(CH$_2$)$_m$C(R$_{13}$)$_2$(CH$_2$)$_m$C(O)O—, NH$_2$CH$_2$CH$_2$C(O)O—, R$_{12}$ON=CH(CH$_2$)$_n$O—, HONHC(O)(CH$_2$)$_n$O—, —OP(O)(OR$_P$)$_2$, —OS(O)$_2$OR$_S$, or R$_{20}$.

Embodiment 54 encompasses compounds of any of Embodiments 6-8 and 13-51 wherein $R_7$ is aryl, aryl($C_1$-$C_8$)alkyl, $C_3$-$C_8$ cycloalkyl, ($C_3$-$C_8$)cycloalkyl($C_1$-$C_8$)alkyl, heteroaryl, heteroaryl($C_1$-$C_8$)alkyl, heterocyclyl, or heterocycle($C_1$-$C_8$)alkyl, wherein each is optionally substituted with 1, 2, 3, 4, or 5 groups which are ($C_2$-$C_8$)alkenyl, ($C_1$-$C_8$)alkoxy, ($C_1$-$C_8$)alkoxy($C_1$-$C_8$)alkyl, ($C_1$-$C_8$)alkoxycarbonyl, ($C_1$-$C_8$)alkyl, ($C_1$-$C_8$)alkylcarbonyl, ($C_1$-$C_8$)alkylcarbonyloxy, ($C_1$-$C_8$)alkylsulfinyl, ($C_1$-$C_8$)alkylsulfonyl, ($C_1$-$C_8$)alkylthio, ($C_2$-$C_8$)alkynyl, carboxy, carboxy($C_1$-$C_8$)alkyl, cyano, cyano($C_1$-$C_8$)alkyl, ($C_3$-$C_8$)cycloalkyl, ($C_3$-$C_8$)cycloalkyl($C_1$-$C_8$)alkyl, formyl, halo($C_1$-$C_8$)alkoxy, halo($C_1$-$C_8$)alkyl, halogen, hydroxy, hydroxy($C_1$-$C_8$)alkoxy, hydroxy($C_1$-$C_8$)alkoxy($C_1$-$C_8$)alkoxy, hydroxy($C_1$-$C_8$)alkyl, mercapto, nitro, —NR$_{12}$R$_{13}$, (NR$_{12}$R$_{13}$)($C_1$-$C_8$)alkyl, (NR$_{12}$R$_{13}$)carbonyl, oxo, HOCH$_2$CH(NH$_2$)C(O)O—, NH$_2$(CH$_2$)$_m$C(O)O—, CH$_3$NH(CH$_2$)$_m$C(O)O—, (CH$_3$)$_2$N(CH$_2$)$_m$ C(O)O—, NH$_2$(CH$_2$)$_t$C(O)—NH(CH$_2$)$_m$C(O)O—, R$_{13}$CH(NH$_2$)C(O)O—, NH$_2$(CH$_2$)$_m$C(R$_{13}$)$_2$(CH$_2$)$_m$C(O)O—, NH$_2$CH$_2$CH$_2$C(O)O—, R$_{12}$ON=CH(CH$_2$)$_n$O—, HONHC(O)(CH$_2$)$_n$O—, —OP(O)(OR$_P$)$_2$, —OS(O)$_2$OR$_S$, or R$_{20}$.

Particular embodiments of the disclosure include those of Embodiment 55, i.e., compounds of Embodiments 6-8 and 13-51 wherein $R_7$ is $C_3$-$C_8$ cycloalkyl or heterocyclyl, wherein each is optionally substituted with 1, 2, 3, 4, or 5 groups which are ($C_2$-$C_8$)alkenyl, ($C_1$-$C_8$)alkoxy, ($C_1$-$C_8$)alkoxy($C_1$-$C_8$)alkyl, ($C_1$-$C_8$)alkoxycarbonyl, ($C_1$-$C_8$)alkyl, ($C_1$-$C_8$)alkylcarbonyl, ($C_1$-$C_8$)alkylcarbonyloxy, ($C_1$-$C_8$)alkylsulfinyl, ($C_1$-$C_8$)alkylsulfonyl, ($C_1$-$C_8$)alkylthio, ($C_2$-$C_8$)alkynyl, carboxy, carboxy($C_1$-$C_8$)alkyl, cyano, cyano ($C_1$-$C_8$)alkyl, ($C_3$-$C_8$)cycloalkyl, ($C_3$-$C_8$)cycloalkyl($C_1$-$C_8$) alkyl, formyl, halo($C_1$-$C_8$)alkoxy, halo($C_1$-$C_8$)alkyl, halogen, hydroxy, hydroxy($C_1$-$C_8$)alkoxy, hydroxy($C_1$-$C_8$) alkoxy($C_1$-$C_8$)alkoxy, hydroxy($C_1$-$C_8$)alkyl, mercapto, nitro, —NR$_{12}$R$_{13}$, (NR$_{12}$R$_{13}$)($C_1$-$C_8$)alkyl, (NR$_{12}$R$_{13}$)carbonyl, oxo, HOCH$_2$CH(NH$_2$)C(O)O—, NH$_2$(CH$_2$)$_m$C(O) O—, CH$_3$NH(CH$_2$)$_m$C(O)O—, (CH$_3$)$_2$N(CH$_2$)$_m$C(O)O—, NH$_2$(CH$_2$)$_t$C(O)—NH(CH$_2$)$_m$C(O)O—, R$_{13}$CH(NH$_2$)C(O) O—, NH$_2$(CH$_2$)$_m$C(R$_{13}$)$_2$(CH$_2$)$_m$C(O)O—, NH$_2$CH$_2$CH$_2$C (O)O—, R$_{12}$ON=CH(CH$_2$)$_n$O—, HONHC(O)(CH$_2$)$_n$O—, —OP(O)(OR$_P$)$_2$, —OS(O)$_2$OR$_S$, or R$_{20}$.

Other particular embodiments include those of Embodiment 56, i.e., compounds of Embodiments 6-8 and 13-51 wherein $R_7$ is $C_3$-$C_8$ cycloalkyl or heterocyclyl, wherein each is optionally substituted with 1, 2, 3, 4, or 5 groups which are ($C_1$-$C_8$)alkoxy, carboxy, cyano, formyl, halo($C_1$-$C_8$)alkoxy, halo($C_1$-$C_8$)alkyl, halogen, hydroxy, hydroxy ($C_1$-$C_8$)alkoxy, hydroxy($C_1$-$C_8$)alkoxy($C_1$-$C_8$)alkoxy, —NR$_{12}$R$_{13}$, —OP(O)(OR$_P$)$_2$, —OS(O)$_2$OR$_S$, or R$_{20}$. In certain embodiments, the heterocyclyl is a 5-, 6-, or 7-member heterocyclyl ring, such as but not limited to tetrahydrofuran, piperidinyl, piperazinyl, morpholinyl, pyrrolidinyl, pyridinonyl, dihydropyrrolidinyl, and pyrrolidinonyl.

Another embodiment, Embodiment 57, encompasses compounds of any of Embodiments 6-8 and 13-51 wherein $R_7$ is optionally substituted $C_3$-$C_8$ cycloalkyl. Particular embodiments based on Embodiment 57 include those of Embodiment 58, wherein $R_7$ is optionally substituted cyclopentyl or cyclohexyl. Other particular embodiments based on Embodiment 57 include those of Embodiment 59, wherein $R_7$ is cyclopentyl or cyclohexyl, each of which is substituted with 1, or 2, or 3 groups independently selected from hydroxy, $C_1$-$C_8$ alkoxy, and $(C_1$-$C_8)$alkylcarbonyloxy. Particular embodiments of Embodiment 59 include those wherein $R_7$ is cyclopentyl or cyclohexyl substituted with 1 of hydroxy, $C_1$-$C_8$ alkoxy, or $(C_1$-$C_8)$alkylcarbonyloxy. Other particular embodiments based on Embodiment 57 include those of Embodiment 60, wherein $R_7$ is cyclopentyl or cyclohexyl, each independently substituted with hydroxy or $C_1$-$C_8$ alkoxy. In embodiment 61, which is based on Embodiment 57, $R_7$ is:

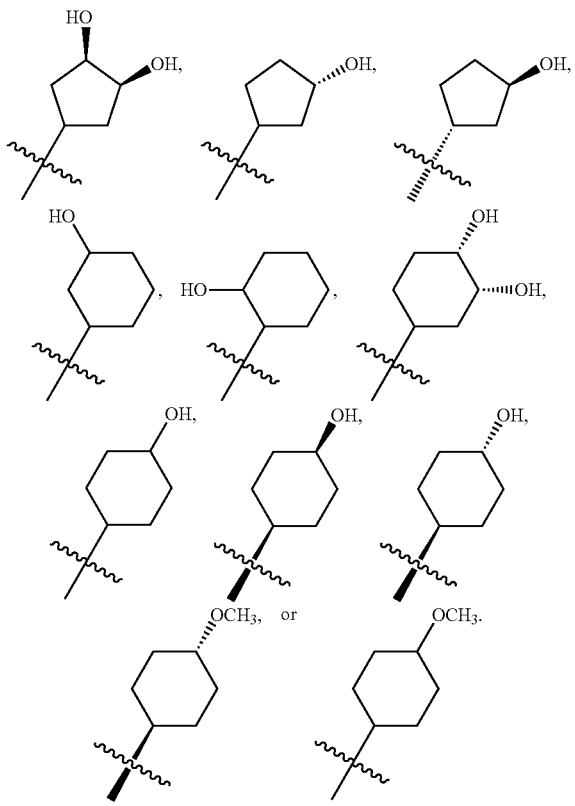

Embodiment 62 encompasses compounds of any of Embodiments 6-8 and 13-51 where $R_7$ is 4-hydroxycyclohexyl or 2-hydroxycyclohexyl. Embodiment 63 encompasses compounds of any of Embodiments 6-8 and 13-51 where $R_7$ is 4-acetyloxycyclohexyl or 2-acetyloxycyclohexyl. More particularly in Embodiment 63, $R_7$ is 4-acetyloxycyclohexyl. Embodiment 64 encompasses compounds of any of Embodiments 6-8 and 13-51 wherein $R_7$ is unsubstituted cyclopentyl or cyclohexyl.

Particular embodiments include those of Embodiment 65, i.e., compounds of any of Embodiments 6-8 and 13-51 wherein $R_7$ is optionally substituted heterocyclyl. In Embodiment 66, which is based on Embodiment 65, $R_7$ is optionally substituted 5, 6, or 7 member heterocyclyl ring. In Embodiment 67, which is based on Embodiment 65, $R_7$ is optionally substituted 5 or 6 member heterocyclyl ring. In Embodiment 68, which is based on embodiment 65, the compounds are those where $R_7$ is optionally substituted tetrahydrofuran, piperidinyl, piperazinyl, morpholinyl, pyrrolidinyl, pyridinonyl, dihydropyrrolidinyl, and pyrrolidinonyl Another embodiment of the disclosure, i.e., Embodiment 69, encompasses compounds of any of Embodiments 6-8 and 13-68 wherein $R_8$ is hydrogen.

Another embodiment of the disclosure, i.e., Embodiment 70, encompasses compounds of any of Embodiments 6-8 and 13-68 wherein $R_8$ is $C_1$-$C_6$ alkyl.

Embodiment 71 encompasses compounds of any Embodiments 1-13 and 36-70, where $R_3$ is hydrogen, halogen, cyano, —N(R$_N$)$_2$, $C_1$-$C_6$ alkyl, $C_1$-$C_6$ alkoxy, or $C_1$-$C_6$ haloalkyl;

$R_4$ and $R_5$ are independently hydrogen;

$R_6$ is a —NHC$_1$-C$_{14}$ alkyl group where up to six of the carbon atoms in said alkyl group are optionally replaced independently by $R_{22}$, carbonyl, ethenyl, ethynyl or a moiety selected from N, O, S, SO$_2$, or SO, with the proviso that two O atoms, two S atoms, or an O and S atom are not immediately adjacent each other, wherein $R_{22}$ is heteroaryl, aryl, saturated or unsaturated $C_3$-$C_{10}$ cycloalkyl, or saturated or unsaturated $C_2$-$C_{10}$ heterocycloalkyl, wherein each aryl, heteroaryl, saturated or unsaturated cycloalkyl, or saturated or unsaturated heterocycloalkyl, independently, is optionally substituted with at least one group, which independently is hydroxy, halo, amino, cyano, carboxy, carboxamido, nitro, oxo, —S—(C$_1$-C$_6$)alkyl, —SO$_2$—(C$_1$-C$_6$)alkyl, —SO$_2$-aryl, —SO—(C$_1$-C$_6$)alkyl, —SO-aryl, —SO$_2$NH$_2$, —SO$_2$NH—(C$_1$-C$_6$)alkyl, —SO$_2$NH-aryl, (C$_1$-C$_6$)alkoxy, or mono- or di-(C$_1$-C$_{10}$)alkylamino; and wherein each is optionally fused to a $C_6$-$C_{10}$ aryl group, $C_5$-$C_8$ saturated cyclic group, or a $C_6$-$C_{10}$ heterocycloalkyl group;

and wherein $R_6$ group is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—(C$_1$-C$_6$)alkyl, —SO$_2$—(C$_1$-C$_6$)alkyl, —SO$_2$NH$_2$, —SO$_2$NH—(C$_1$-C$_6$)alkyl, —SO$_2$NH-aryl, —SO$_2$-aryl, —SO—(C$_1$-C$_6$)alkyl, —SO$_2$-aryl, $C_1$-$C_6$ alkoxy, $C_2$-$C_{10}$ alkenyloxy, $C_2$-$C_{10}$ alkynyloxy, mono- or di-(C$_1$-C$_{10}$)alkylamino, —OC$_1$-C$_{10}$ alkyl-Z, or $R_{23}$, wherein Z is OR$_{31}$ or —N(R$_{30}$)$_2$, wherein
each $R_{30}$ is independently hydrogen or $C_1$-$C_6$ alkyl, or N(R$_{30}$)$_2$ represents pyrrolidinyl, piperidinyl, piperazinyl, azepanyl, 1,3- or 1,4-diazepanyl, or morpholinyl, each of which is optionally substituted with hydroxy, amino, aminoalkyl, $C_1$-$C_6$ alkyl, mono- or di(C$_1$-C$_6$)alkylamino, $C_1$-$C_6$ alkoxy, or halogen;

$R_{31}$ is hydrogen, $C_1$-$C_{10}$ alkyl, $C_2$-$C_{10}$ alkenyl, $C_2$-$C_{10}$ alkynyl, aryl, heteroaryl, or $C_1$-$C_6$ acyl;

$R_{23}$ is heteroaryl, aryl, saturated or unsaturated $C_5$-$C_{10}$ cycloalkyl, or saturated or unsaturated $C_5$-$C_{10}$ heterocycloalkyl, and each is optionally substituted at least one group which is independently hydroxy, oxo, halo, amino, cyano, nitro, —SH, —S—(C$_1$-C$_6$) alkyl, —SO$_2$—(C$_1$-C$_6$)alkyl, —SO$_2$-aryl, —SO—(C$_1$-C$_6$)alkyl, —SO-aryl, —SO$_2$NH$_2$, —SO$_2$NH—

($C_1$-$C_6$)alkyl, —$SO_2$NH-aryl, $C_1$-$C_6$ alkoxy, or mono- or di-($C_1$-$C_{10}$)alkylamino;

$R_9$ and $R_{10}$ are independently $C_1$-$C_3$ alkyl;

$R_{11}$ is hydrogen, hydroxy, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, mono- or di-($C_1$-$C_6$)alkylamino, $C_1$-$C_6$ alkoxy($C_1$-$C_6$)alkyl, hydroxy($C_1$-$C_6$) alkoxy, or amino($C_1$-$C_6$) alkoxy;

X is N; and

Y is N or $CR_C$;

each $R_C$ is independently is hydrogen, halogen, cyano, nitro, $C_1$-$C_6$ alkyl, $C_2$-$C_6$ alkenyl, $C_2$-$C_6$ alkynyl, $C_1$-$C_6$ haloalkyl, $C_3$-$C_7$ cycloalkyl, $C_3$-$C_7$ cycloalkyl($C_1$-$C_6$) alkyl, heterocycloalkyl, aryl, or heteroaryl, wherein each alkyl, aryl, cycloalkyl, heterocycloalkyl, and heteroaryl group is optionally substituted as indicated above.

Another embodiment of the disclosure, i.e., Embodiment 72, encompasses compounds of Embodiment 71 wherein $R_6$ is a —$NHR_{22}$, wherein $R_{22}$ is heteroaryl, aryl, saturated or unsaturated $C_3$-$C_{10}$ cycloalkyl, or saturated or unsaturated $C_2$-$C_{10}$ heterocycloalkyl, wherein each aryl, heteroaryl, saturated or unsaturated cycloalkyl, or saturated or unsaturated heterocycloalkyl, independently, is optionally substituted with at least one group, which independently is hydroxy, halo, amino, cyano, carboxy, carboxamido, nitro, oxo, —S—($C_1$-$C_6$)alkyl, —$SO_2$—($C_1$-$C_6$)alkyl, —$SO_2$-aryl, —SO—($C_1$-$C_6$)alkyl, —SO-aryl, —$SO_2NH_2$, —$SO_2$NH—($C_1$-$C_6$)alkyl, —$SO_2$NH-aryl, ($C_1$-$C_6$)alkoxy, or mono- or di-($C_1$-$C_{10}$)alkylamino; and wherein each is optionally fused to a $C_6$-$C_{10}$ aryl group, $C_5$-$C_8$ saturated cyclic group, or a $C_5$-$C_{10}$ heterocycloalkyl group;

and wherein $R_6$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$, wherein Z is $OR_{31}$ or —$N(R_{30})_2$, wherein each $R_{30}$ is independently hydrogen or $C_1$-$C_6$ alkyl, or $N(R_{30})_2$ represents pyrrolidinyl, piperidinyl, piperazinyl, azepanyl, 1,3- or 1,4-diazepanyl, or morpholinyl, each of which is optionally substituted with hydroxy, amino, aminoalkyl, $C_1$-$C_6$ alkyl, mono- or di($C_1$-$C_6$)alkylamino, $C_1$-$C_6$ alkoxy, or halogen;

$R_{31}$ is hydrogen, $C_1$-$C_{10}$ alkyl, $C_2$-$C_{10}$ alkenyl, $C_2$-$C_{10}$ alkynyl, aryl, heteroaryl, or $C_1$-$C_6$ acyl;

$R_{23}$ is heteroaryl, aryl, saturated or unsaturated $C_5$-$C_{10}$ cycloalkyl, or saturated or unsaturated $C_6$-$C_{10}$ heterocycloalkyl, and each is optionally substituted at least one group which is independently hydroxy, oxo, halo, amino, cyano, nitro, —SH, —S—($C_1$-$C_6$) alkyl, —$SO_2$—($C_1$-$C_6$)alkyl, —$SO_2$-aryl, —SO—($C_1$-$C_6$)alkyl, —SO-aryl, —$SO_2NH_2$, —$SO_2$NH—($C_1$-$C_6$)alkyl, —$SO_2$NH-aryl, $C_1$-$C_6$ alkoxy, or mono- or di-($C_1$-$C_{10}$)alkylamino.

Yet another embodiment of the disclosure, Embodiment 73, encompasses compounds of Embodiment 71 wherein $R_6$ is a —$NHR_{22}$, wherein $R_{22}$ is saturated or unsaturated $C_3$-$C_{10}$ cycloalkyl, or saturated or unsaturated $C_2$-$C_{10}$ heterocycloalkyl, wherein each cycloalkyl or heterocycloalkyl, independently, is optionally substituted with at least one group, which independently is hydroxy, halo, amino, cyano, carboxy, carboxamido, nitro, oxo, —S—($C_1$-$C_6$)alkyl, —$SO_2$—($C_1$-$C_6$)alkyl, —$SO_2$-aryl, —SO—($C_1$-$C_6$) alkyl, —SO-aryl, —$SO_2NH_2$, —$SO_2$NH—($C_1$-$C_6$) alkyl, —$SO_2$NH-aryl, ($C_1$-$C_6$)alkoxy, or mono- or di-($C_1$-$C_{10}$)alkylamino; and wherein each is optionally fused to a $C_6$-$C_{10}$ aryl group, $C_5$-$C_8$ saturated cyclic group, or a $C_5$-$C_{10}$ heterocycloalkyl group;

and wherein $R_6$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$.

Yet another embodiment of the disclosure, Embodiment 74, encompasses compounds of Embodiment 71 wherein $R_{22}$ is saturated or unsaturated $C_3$-$C_{10}$ cycloalkyl, optionally substituted with at least one group, which independently is hydroxy, halo, amino, cyano, carboxy, carboxamido, nitro, oxo, —S—($C_1$-$C_6$)alkyl, —$SO_2$—($C_1$-$C_6$)alkyl, —$SO_2$-aryl, —SO—($C_1$-$C_6$)alkyl, —SO-aryl, —$SO_2NH_2$, —$SO_2$NH—($C_1$-$C_6$)alkyl, —$SO_2$NH-aryl, ($C_1$-$C_6$)alkoxy, or mono- or di-($C_1$-$C_{10}$)alkylamino; and wherein each is optionally fused to a $C_6$-$C_{10}$ aryl group, $C_5$-$C_8$ saturated cyclic group, or a $C_5$-$C_{10}$ heterocycloalkyl group;

and wherein $R_6$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$.

Yet another embodiment of the disclosure, Embodiment 75, encompasses compounds of Embodiment 71 wherein $R_{22}$ is saturated or unsaturated $C_2$-$C_{10}$ heterocycloalkyl, optionally substituted with at least one group, which independently is hydroxy, halo, amino, cyano, carboxy, carboxamido, nitro, oxo, —S—($C_1$-$C_6$)alkyl, —$SO_2$—($C_1$-$C_6$)alkyl, —$SO_2$-aryl, —SO—($C_1$-$C_6$)alkyl, —SO-aryl, —$SO_2NH_2$, —$SO_2$NH—($C_1$-$C_6$)alkyl, —$SO_2$NH-aryl, ($C_1$-$C_6$)alkoxy, or mono- or di-($C_1$-$C_{10}$)alkylamino; and wherein each is optionally fused to a $C_6$-$C_{10}$ aryl group, $C_5$-$C_8$ saturated cyclic group, or a $C_5$-$C_{10}$ heterocycloalkyl group;

and wherein $R_6$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$.

In another aspect, the invention provides Embodiment 76 which is compounds of Formulas I-1A and I-2A wherein $R_1$ and $R_2$ are —H; $R_3$, $R_4$, and $R_5$ are independently —H, —F, or —$OCH_3$; and $R_7$ is ($C_1$-$C_{14}$)alkyl, ($C_3$-$C_8$)cycloalkenyl, ($C_3$-$C_8$)cycloalkyl, ($C_3$-$C_8$)cycloalkyl($C_1$-$C_8$)alkyl, heteroaryl, heteroaryl($C_1$-$C_8$)alkylthio($C_1$-$C_8$)alkyl, heteroarylthio($C_1$-$C_8$)alkyl, heterocyclyl, or hydroxy($C_1$-$C_8$)alkyl, wherein the $R_7$ group is optionally substituted with 1, 2, 3, or 4 groups that are ($C_2$-$C_8$)alkenyl, ($C_1$-$C_8$)alkoxy, ($C_1$-$C_8$)alkoxy($C_1$-$C_8$)alkyl, ($C_1$-$C_8$)alkoxycarbonyl, ($C_1$-$C_8$)alkyl, ($C_1$-$C_8$)alkylcarbonyl, ($C_2$-$C_8$)alkynyl, ($C_3$-$C_8$)cycloalkyl, ($C_3$-$C_8$)cycloalkyl($C_1$-$C_8$)alkyl, hydroxy, hydroxy($C_1$-$C_8$)alkoxy, hydroxy($C_1$-$C_8$)alkoxy($C_1$-$C_8$)alkoxy, hydroxy($C_1$-$C_8$)alkyl, —$NR_{110}R_{120}$, ($NR_{110}R_{120}$)($C_1$-$C_8$)alkyl, oxo, $HOCH_2CH(NH_2)C(O)O$—, $NH_2(CH_2)_mC(O)O$—, $CH_3NH(CH_2)_mC(O)O$—, $(CH_3)_2N(CH_2)_mC(O)O$—, $NH_2(CH_2)_tC(O)NH(CH_2)_mC(O)O$—, $R_{120}CH(NH_2)C(O)O$—, $NH_2(CH_2)_mC(R_{120})_2(CH_2)_mC(O)O$—, $NH_2CH_2CH_2C(O)O$—, $R_{110}ON=CH(CH_2)_nO$—, or $HONHC(O)(CH_2)_nO$—; $R_8$ is —H; $R_C$ is ($C_1$-$C_8$)alkyl, ($C_3$-$C_8$)cycloalkyl($C_1$-$C_8$)alkyl, aryl, aryl($C_1$-$C_8$)alkyl, halo($C_1$-$C_8$)alkyl, heteroaryl($C_1$-$C_8$)alkyl, or hydroxy($C_1$-$C_8$)alkyl; $R_9$ and $R_{10}$ are independently ($C_1$-$C_8$)alkyl; $R_{110}$ and $R_{120}$ are independently —H, ($C_1$-$C_8$)alkyl, ($C_2$-$C_8$)alkynyl, ($C_3$-$C_8$)cycloalkyl, ($C_3$-$C_8$)cycloalkyl($C_1$-$C_8$)alkyl, or two $R_{120}$ groups together with the carbon to which they are attached form a ($C_3$-$C_8$)cycloalkyl group; n is 1; each m is independently 1 or 2; and each t is independently 1 or 2.

In another aspect, the invention provides compounds of Formulas I-1A and I-2A wherein $R_1$ and $R_2$ are —H; $R_3$ is —F; $R_4$ and $R_5$ are —H; $R_7$ is cyclobutyl, cyclopentyl, cyclohexyl, or cycloheptyl, wherein each is optionally substituted with one group that is ($C_1$-$C_8$)alkoxy, hydroxy, $R_{120}CH(NH_2)C(O)O$—, $NH_2CH_2C(O)O$—, $NH_2CH_2CH_2C(O)O$— or —$NR_{110}R_{120}$; $R_8$ is —H; $R_C$ is methyl, ethyl, cyclopropylmethyl, or trifluoromethyl; $R_9$ and $R_{10}$ are methyl; $R_{11}$ is H or $R_{11}$ is $CH_3$; and $R_{110}$ and $R_{120}$ are independently —H or ($C_1$-$C_8$)alkyl.

In another aspect, the invention provides compounds of Formulas I-1A and I-2A wherein $R_1$ and $R_2$ are —H; $R_3$ is —F; $R_4$ and $R_5$ are —H; $R_7$ is cyclobutyl, cyclopentyl, cycloheptyl, 2-hydroxycyclopentyl, 2-(2-aminoacetoxy)cyclopentyl, 2-(2-aminoacetoxy)cyclohexyl, 4-(2-aminoacetoxy)cyclohexyl, 2-aminocyclohexyl, 2-hydroxycyclohexyl, 4-hydroxycyclohexyl, 2-neopentylaminocyclohexyl, 4-neopentylaminocyclohexyl, or 4-methoxycyclohexyl; $R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

In another aspect, the invention provides compounds of Formulas I-1A and I-2A wherein $R_1$ and $R_2$ are —H; $R_3$ is —F; $R_4$ and $R_5$ are —H; $R_7$ is cyclobutyl, cyclopentyl, cycloheptyl, trans-2-hydroxycyclopentyl, trans-2-(2-aminoacetoxy)cyclohexyl, trans-4-(2-aminoacetoxy)cyclohexyl, trans-2-aminocyclohexyl, trans-2-hydroxycyclohexyl, trans-4-hydroxycyclohexyl, trans-2-neopentylaminocyclohexyl, trans-4-neopentylaminocyclohexyl, or trans-4-methoxycyclohexyl; $R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

In another aspect, the invention provides compounds of Formulas I-1A and I-2A wherein $R_1$ and $R_2$ are —H; $R_3$ is —F; $R_4$ and $R_5$ are —H; $R_7$ is oxetanyl, tetrahydrofuranyl, tetrahydropyran, piperidinyl, or azepanyl, wherein each is optionally substituted with 1 group that is ($C_1$-$C_8$)alkylcarbonyl or oxo; $R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

In another aspect, the invention provides compounds of Formulas I-1A and I-2A wherein $R_1$ and $R_2$ are —H; $R_4$ is —F; $R_3$ and $R_5$ are —H; $R_7$ is cyclobutyl, cyclopentyl, or cyclohexyl, wherein each is optionally substituted with one group that is ($C_1$-$C_8$)alkoxy, hydroxy, $R_{120}CH(NH_2)C(O)O$—, $NH_2CH_2CH_2C(O)O$— or —$NR_{110}R_{120}$; $R_8$ is —H; $R_C$ is methyl, ethyl, cyclopropylmethyl, or trifluoromethyl; $R_9$ and $R_{10}$ are methyl; $R_{11}$ is H or $R_{11}$ is $CH_3$; and $R_{110}$ and $R_{120}$ are independently —H or ($C_1$-$C_8$)alkyl.

In another aspect, the invention provides compounds of Formulas I-1A and I-2A wherein $R_1$ and $R_2$ are —H; $R_4$ is —F; $R_3$ and $R_5$ are —H; $R_7$ is cyclobutyl, 2-hydroxycyclopentyl, 2-aminocyclohexyl, 2-hydroxycyclohexyl, 4-hydroxycyclohexyl, 2-neopentylaminocyclohexyl, 4-neopentylaminocyclohexyl, or 4-methoxycyclohexyl; $R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

In another aspect, the invention provides compounds of Formulas I-1A and I-2A wherein $R_1$ and $R_2$ are —H; $R_4$ is —F; $R_3$ and $R_5$ are —H; $R_7$ is cyclobutyl, trans-2-hydroxycyclopentyl, trans-2-aminocyclohexyl, trans-2-hydroxycyclohexyl, trans-4-hydroxycyclohexyl, trans-2-neopentylaminocyclohexyl, trans-4-neopentylaminocyclohexyl, or trans-4-methoxycyclohexyl; $R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

In another aspect, the invention provides compounds of Formulas I-1A and I-2A wherein $R_1$ and $R_2$ are —H; $R_4$ is —F; $R_3$ and $R_5$ are —H; $R_7$ is tetrahydrofuranyl, tetrahydropyran, piperidinyl, or azepanyl, wherein each is optionally substituted with 1 group that is ($C_1$-$C_8$)alkylcarbonyl or oxo; $R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

In another aspect, the invention provides compounds of Formulas I-1A and I-2A wherein $R_1$ and $R_2$ are —H; $R_4$ is —F; $R_3$ and $R_5$ are —H; $R_7$ is tetrahydrofuranyl, 2-oxotetrahydrofuranyl, tetrahydropyranyl, 2-oxoazepanyl, or 1-acetylpiperidinyl; $R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

In another aspect, the invention provides compounds of Formulas I-1A and I-2A wherein $R_1$ and $R_2$ are —H; $R_3$ and $R_4$ are —H; $R_5$ is —F; $R_7$ is cyclobutyl, cyclopentyl, or cyclohexyl, wherein each is optionally substituted with one group that is ($C_1$-$C_8$)alkoxy, hydroxy, $R_{120}CH(NH_2)C(O)O$—, $NH_2CH_2CH_2C(O)O$— or —$NR_{110}R_{120}$; $R_8$ is —H; $R_C$ is methyl, ethyl, cyclopropylmethyl, or trifluoromethyl; $R_9$ and $R_{10}$ are methyl; $R_{11}$ is H or $R_{11}$ is $CH_3$; and $R_{110}$ and $R_{120}$ are independently —H or ($C_1$-$C_8$)alkyl.

In another aspect, the invention provides compounds of Formulas I-1A and I-2A wherein $R_1$ and $R_2$ are —H; $R_3$ and $R_4$ are —H; $R_5$ is —F; $R_7$ is cyclobutyl, 2-hydroxycyclopentyl, 2-aminocyclohexyl, 2-hydroxycyclohexyl, 4-hydroxycyclohexyl, 2-neopentylaminocyclohexyl, 4-neopentylaminocyclohexyl, or 4-methoxycyclohexyl; $R_8$ is —H; $R_C$ is methyl, ethyl, cyclopropylmethyl, or trifluoromethyl; and $R_9$ and $R_{10}$ are methyl; $R_{11}$ is H or $R_{11}$ is $CH_3$.

In another aspect, the invention provides compounds of Formulas I-1A and I-2A wherein $R_1$ and $R_2$ are —H; $R_3$ and $R_4$ are —H; $R_5$ is —F; $R_7$ is cyclobutyl, trans-2-hydroxycyclopentyl, trans-2-aminocyclohexyl, trans-2-hydroxycyclohexyl, trans-4-hydroxycyclohexyl, trans-2-neopentylaminocyclohexyl, trans-4-neopentylaminocyclohexyl, or trans-4-methoxycyclohexyl; $R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

In another aspect, the invention provides compounds of Formulas I-1A and I-2A wherein $R_1$ and $R_2$ are —H; $R_3$ and $R_4$ are —H; $R_5$ is —F; $R_7$ is tetrahydrofuranyl, tetrahydropyran, piperidinyl, or azepanyl, wherein each is optionally substituted with 1 group that is ($C_1$-$C_8$)alkylcarbonyl or oxo;

$R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

In another aspect, the invention provides compounds of Formulas I-1A and I-2A wherein $R_1$ and $R_2$ are —H; $R_3$ and $R_4$ are —H; $R_5$ is —F; $R_7$ is tetrahydrofuranyl, 2-oxotetrahydrofuranyl, tetrahydropyranyl, 2-oxoazepanyl, or 1-acetylpiperidinyl; $R_8$ is —H; $R_C$ is methyl, ethyl, cyclopropylmethyl, or trifluoromethyl; and $R_9$ and $R_{10}$ are methyl; $R_{11}$ is H or $R_{11}$ is $CH_3$.

In another aspect, the invention provides compounds of Formulas I-1A and I-2A wherein $R_1$ and $R_2$ are —H; $R_3$ is —H; $R_4$ and $R_5$ are —F; $R_7$ is cyclobutyl, cyclopentyl, or cyclohexyl, wherein each is optionally substituted with one group that is $(C_1-C_8)$alkoxy, hydroxy, $R_{120}CH(NH_2)C(O)O$—, $NH_2CH_2CH_2C(O)O$— or —$NR_{110}R_{120}$; $R_8$ is —H; $R_C$ is methyl, ethyl, cyclopropylmethyl, or trifluoromethyl; $R_9$ and $R_{10}$ are methyl; $R_{11}$ is H or $R_{11}$ is $CH_3$; and $R_{110}$ and $R_{120}$ are independently —H or $(C_1-C_8)$alkyl.

In another aspect, the invention provides compounds of Formulas I-1A and I-2A wherein $R_1$ and $R_2$ are —H; $R_3$ is —H; $R_4$ and $R_5$ are —F; $R_7$ is cyclobutyl, 2-hydroxycyclopentyl, 2-aminocyclohexyl, 2-hydroxycyclohexyl, 4-hydroxycyclohexyl, 2-neopentylaminocyclohexyl, 4-neopentylaminocyclohexyl, or 4-methoxycyclohexyl; $R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

In another aspect, the invention provides compounds of Formulas I-1A and I-2A wherein $R_1$ and $R_2$ are —H; $R_3$ is —H; $R_4$ and $R_5$ are —F; $R_7$ is cyclobutyl, trans-2-hydroxycyclopentyl, trans-2-aminocyclohexyl, trans-2-hydroxycyclohexyl, trans-4-hydroxycyclohexyl, trans-2-neopentylaminocyclohexyl, trans-4-neopentylaminocyclohexyl, or trans-4-methoxycyclohexyl; $R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

In another aspect, the invention provides compounds of Formulas I-1A and I-2A wherein $R_1$ and $R_2$ are —H; $R_3$ is —H; $R_4$ and $R_5$ are —F; $R_7$ is tetrahydrofuranyl, tetrahydropyran, piperidinyl, or azepanyl, wherein each is optionally substituted with 1 group that is $(C_1-C_8)$alkylcarbonyl or oxo; $R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

In another aspect, the invention provides compounds of Formulas I-1A and I-2A wherein $R_1$ and $R_2$ are —H; $R_3$ is —H; $R_4$ and $R_5$ are —F; $R_7$ is tetrahydrofuranyl, 2-oxotetrahydrofuranyl, tetrahydropyranyl, 2-oxoazepanyl, or 1-acetylpiperidinyl; $R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

In another aspect, the invention provides compounds of Formulas I-1A and I-2A wherein $R_1$ and $R_2$ are —H; $R_3$, $R_4$, and $R_5$ are —F; $R_7$ is cyclobutyl, cyclopentyl, or cyclohexyl, wherein each is optionally substituted with one group that is $(C_1-C_8)$alkoxy, hydroxy, $R_{120}CH(NH_2)C(O)O$—, $NH_2CH_2CH_2C(O)O$— or —$NR_{110}R_{120}$; $R_8$ is —H; $R_C$ is methyl, ethyl, cyclopropylmethyl, or trifluoromethyl; $R_9$ and $R_{10}$ are methyl; $R_{11}$ is H or $R_{11}$ is $CH_3$; and $R_{110}$ and $R_{120}$ are independently —H or $(C_1-C_8)$alkyl.

In another aspect, the invention provides compounds of Formulas I-1A and I-2A wherein $R_1$ and $R_2$ are —H; $R_3$, $R_4$, and $R_5$ are —F; $R_7$ is cyclobutyl, 2-hydroxycyclopentyl, 2-aminocyclohexyl, 2-hydroxycyclohexyl, 4-hydroxycyclohexyl, 2-neopentylaminocyclohexyl, 4-neopentylaminocyclohexyl, or 4-methoxycyclohexyl; $R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

In another aspect, the invention provides compounds of Formulas I-1A and I-2A wherein $R_1$ and $R_2$ are —H; $R_3$, $R_4$, and $R_5$ are —F; $R_7$ is cyclobutyl, trans-2-hydroxycyclopentyl, trans-2-aminocyclohexyl, trans-2-hydroxycyclohexyl, trans-4-hydroxycyclohexyl, trans-2-neopentylaminocyclohexyl, trans-4-neopentylaminocyclohexyl, or trans-4-methoxycyclohexyl; $R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

In another aspect, the invention provides compounds of Formulas I-1A and I-2A wherein $R_1$ and $R_2$ are —H; $R_3$, $R_4$, and $R_5$ are —F; $R_7$ is tetrahydrofuranyl, tetrahydropyran, piperidinyl, or azepanyl, wherein each is optionally substituted with 1 group that is $(C_1-C_8)$alkylcarbonyl or oxo; $R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

In another aspect, the invention provides compounds of Formulas I-1A and I-2A wherein $R_1$ and $R_2$ are —H; $R_3$, $R_4$, and $R_5$ are —F; $R_7$ is tetrahydrofuranyl, 2-oxotetrahydrofuranyl, tetrahydropyranyl, 2-oxoazepanyl, or 1-acetylpiperidinyl; $R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

In another aspect, the invention provides compounds of Formulas I-1A and I-2A wherein $R_1$ and $R_2$ are —H; $R_3$ is —F; $R_4$ and $R_5$ are —H; $R_7$ is cyclobutyl, cyclopentyl, or cyclohexyl, wherein each is optionally substituted with one group that is $(C_1-C_8)$alkoxy, hydroxy, $R_{120}CH(NH_2)C(O)O$—, $NH_2CH_2C(O)O$—, $NH_2CH_2CH_2C(O)O$—, or —$NR_{110}R_{120}$; $R_8$ is —H; $R_C$ is methyl, ethyl, cyclopropylmethyl, or trifluoromethyl; $R_9$ and $R_{10}$ are methyl; $R_{11}$ is H or $R_{11}$ is $CH_3$; and $R_{110}$ and $R_{120}$ are independently —H or $(C_1-C_8)$alkyl.

In another aspect, the invention provides compounds of Formulas I-1A and I-2A wherein $R_1$ and $R_2$ are —H; $R_3$ is —F; $R_4$ and $R_5$ are —H; $R_7$ is cyclobutyl, 2-hydroxycyclopentyl, 2-aminocyclohexyl, 2-(2-aminoacetoxy)cyclopentyl, 2-(2-aminoacetoxy)cyclohexyl, 4-(2-aminoacetoxy)cyclohexyl, 2-hydroxycyclohexyl, 4-hydroxycyclohexyl, 2-neopentylaminocyclohexyl, 4-neopentylaminocyclohexyl, or 4-methoxycyclohexyl; $R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

In another aspect, the invention provides compounds of Formulas I-1A and I-2A wherein $R_1$ and $R_2$ are —H; $R_3$ is —F; $R_4$ and $R_5$ are —H; $R_7$ is cyclobutyl, trans-2-hydroxycyclopentyl, trans-2-(2-aminoacetoxy)cyclopentyl, trans-2-(2-aminoacetoxy)cyclohexyl, trans-4-(2-aminoacetoxy)cyclohexyl, trans-2-aminocyclohexyl, trans-2-hydroxycyclohexyl, trans-4-hydroxycyclohexyl, trans-2-neopentylaminocyclohexyl, trans-4-neopentylaminocyclohexyl, or trans-4-methoxycyclohexyl; $R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

In another aspect, the invention provides compounds of Formulas I-1A and I-2A wherein $R_1$ and $R_2$ are —H; $R_3$ is —F; $R_4$ and $R_5$ are —H; $R_7$ is tetrahydrofuranyl, tetrahydropyran, piperidinyl, or azepanyl, wherein each is optionally substituted with 1 group that is $(C_1-C_8)$alkylcarbonyl or oxo; $R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

In another aspect, the invention provides compounds of Formulas I-1A and I-2A wherein $R_1$ and $R_2$ are —H; $R_3$ is —F; $R_4$ and $R_5$ are —H; $R_7$ is tetrahydrofuranyl, 2-oxotetrahydrofuranyl, tetrahydropyranyl, 2-oxoazepanyl, or 1-acetylpiperidinyl; $R_8$ is —H; $R_C$ is methyl, ethyl, cyclopropylmethyl, or trifluoromethyl; $R_9$ and $R_{10}$ are methyl; and $R_{11}$ is H or $R_{11}$ is $CH_3$.

Inhibition of HSP-90 is also known to result in up regulation of the expression of the chaperone HSP70, and HSP70 up regulation is considered to be of therapeutic benefit for treatment of a wide range of neurodegenerative diseases including, but not limited to: Alzheimer's disease; Parkinson's disease; Dementia with Lewy bodies; Amyotrophic Lateral Sclerosis (ALS); Polyglutamine disease; Huntington's disease; Spinal and bulbar muscular atrophy (SBMA); and Spinocerebellar ataxias (SCA1-3,7). Therefore, the compounds described in the invention are of potential therapeutic use for treatment of such neurodegenerative diseases.

Inhibition of HSP-90 also has antifungal activity, both as stand-alone therapy and in combination with standard antifungal therapies such as the azole class of drugs. Therefore, the compounds described in the invention are of therapeutic use for treatment of fungal infections including, but not limited to, life threatening systemic fungal infections.

Inhibition of HSP-90 also has antimalarial activity; thus inhibitors of this protein are useful as antimalarial drugs.

HSP-90 is nearly universally required for viral protein homeostasis. Currently, Hsp90 inhibitors have been demonstrated to possess antiviral activity in tissue culture against picornaviruses (poliovirus, coxsackievirus, rhinovirus), influenza virus, paramyxoviruses (HPIV2, HPIV3, SV5, SV41), hepatitis C (HCV), hepatitis B (HBV), ebola (EBOV), vesicular stomatitis virus, La crosse virus, severe acquired respiratory syndrome (SARS), Feline herpesvirus (FHV), Human Immunodeficiency Virus Type 1 (HIV), vaccinia virus, and herpes viruses (HSV1/2, HCMV, VZV). Therefore, the compounds described in the invention are of therapeutic use for treatment of viral infections.

In another aspect, the invention encompasses a method of treating cancer comprising administering to a patient in need thereof, a pharmaceutically acceptable amount of a compound of the disclosure or a pharmaceutical composition comprising a compound or salt of a compound of the disclosure. Cancers that may be treated include, but are not limited to, lung, bronchus, prostate, breast, pancreas, colon, rectal, thyroid, stomach, liver, intrahepatic bile duct, kidney, renal pelvis, urinary bladder, uterine corpus, uterine cervix, ovary, multiple myeloma, esophagus, acute myelogenous leukemia, chronic myelogenous leukemia, lymphocytic leukemia, myeloid leukemia, brain, oral cavity, pharynx, larynx, small intestine, non-Hodgkin lymphoma, melanoma, and villous colon adenoma.

In a preferred aspect, the invention encompasses methods for the treatment of cancer in a subject in need of such treatment comprising administration of therapeutically effective amount of a compound of the disclosure or a salt thereof, in combination with at least one other therapeutic agent.

In a more preferred aspect, the invention encompasses methods for treating cancer in a subject in need of such treatment, the methods comprising administration of therapeutically effective amount of a compound of the disclosure or a salt thereof, in combination with at least one other anti-cancer agent.

In another preferred aspect, the invention encompasses methods for treating cancer, the methods comprising administration, to a subject in need of such treatment, of a therapeutically effective amount of a compound of the disclosure or a salt thereof, in combination with radiation therapy.

In another aspect, the invention encompasses a method of treating viral infection comprising administering to a patient in need thereof, a pharmaceutically acceptable amount of a compound of the disclosure or a pharmaceutical composition comprising a compound or salt of a compound of the disclosure. Examples of viral infections treatable by the methods of the disclosure include, but are not limited to, Human Immunodeficiency Virus Type 1 (HIV) (including acquired immunodeficiency syndrome (AIDS)), hepatitis C (HCV), hepatitis B (HBV), ebola (EBOV), picornaviruses (poliovirus, coxsackievirus, rhinovirus), influenza (e.g., Influenza A, influenza B, and Influenza C), paramyxoviruses (HPIV2, HPIV3, SV5, SV41), herpes (including herpes simplex virus HSV1/2 and HCMV), flock house, negative-strand RNA viruses (such as but not limited to, vesicular stomatitis virus, Paramyxovirus (SV5, HPIV-2 & 3, SV41), and LaCrosse bunyavirus), severe acquired respiratory syndrome (SARS), Feline herpesvirus (FHV), Epstein Barr Virus (EBV), Varicella-Zoster Virus (VZV), vaccinia virus, and human cytomegalovirus (HCMV) infections. In particular embodiments, the viral infections are selected from HIV (including AIDS), HCV, HBV, and EBOV infections.

In another aspect, the invention encompasses the use of a therapeutically effective amount of a compound of the disclosure or a salt thereof for the preparation of a medicament for the treatment of cancer, inflammation, infection, or arthritis in a patient in need of such treatment.

In another aspect, the invention encompasses a package comprising a compound of the disclosure or a salt thereof in a container with instructions on how to use the compound.

In another aspect, the invention encompasses the use of a therapeutically effective amount of a compound of the disclosure or a salt thereof for the preparation of a medicament for the treatment of a disease or condition related to cell proliferation in a patient in need of such treatment.

In another aspect, the invention encompasses the use of a therapeutically effective amount of a compound of the disclosure or a salt thereof for the preparation of a medicament for the treatment of a disease or condition related to cell proliferation in a patient in need of such treatment, wherein the disease or condition is cancer, inflammation, infection, or arthritis.

In another aspect, the invention encompasses the use of therapeutically effective amount of a compound of the disclosure or a salt thereof for the preparation of a medicament for the treatment of a disease or disorder related to the activity of heat shock protein 90, in a subject in need of such.

In another aspect, the invention encompasses the use of therapeutically effective amount of a compound of the disclosure or a salt thereof, alone or in combination with another therapeutic agent, for the preparation of a medicament for the treatment of a disease or disorder related to the activity of heat shock protein 90 and/or its client proteins, in a subject in need of such, wherein the HSP-90 mediated disorder is selected from the group of inflammatory diseases, infections, specifically fungal and viral infections, autoimmune disorders, stroke, ischemia, cardiac disorders, neurological disorders, fibrogenetic disorders, proliferative disorders, tumors, leukemias, neoplasms, cancers, carcinomas, metabolic diseases, malaria, and malignant disease.

Pharmaceutical Compositions

The compounds of the disclosure may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of the disclosure and a pharmaceutically acceptable carrier. One or more compounds of the disclosure may be present in association with one or more non-toxic pharmaceutically acceptable carriers and/or diluents and/or adjuvants, and if desired other active ingredients. The pharmaceutical compositions containing compounds of the disclosure be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum *acacia* or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the disclosure may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of the disclosure may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w. For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may be preferable to apply a topical preparation of compounds of this invention to the affected area two to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water. Preferred non-human animals include domesticated animals.

The compounds of the present invention may be administed alone or in combination with at least one additional therapeutic agent or therapy, e.g., radiation therapy, to a patient in need of such treatment. The additional therapeutic agent or therapy may be administed at the same time, separately, or sequentially with respect to the administration of a compound of the invention. Such additional therapeutic agents included, but are not limited to, anti-cancer agents, anti-inflammatory agents, and the like.

Definitions

In Formula I, $R_6$ is, as noted above, independently (a) halogen or (b) an alkyl group having from 1-15 carbon atoms. All, but no more than about six, of the carbon atoms in the alkyl group may be replaced independently by the various groups listed above in connection with Formula I.

Thus, when the alkyl group is methyl, i.e., a one carbon atom alkyl group, replacement of that carbon atom with, for example, nitrogen or sulfur, the resulting group will not be an alkyl group but instead will be an amino or thio group, respectively. Similarly, when the carbon atom being replaced terminates the alkyl group, the terminal group will become another moiety such as pyrimidinyl, amino, phenyl, or hydroxy.

Replacement of a carbon atom with a group such as, for example, oxygen, nitrogen, or sulfur will require appropriate adjustment of the number of hydrogens or other atoms required to satisfy the replacing atom's valency. Thus, when the replacement is N or O, the number of groups attached to the atom being replaced will be reduced by one or two to satisfy the valency of the nitrogen or oxygen respectively. Similar considerations will be readily apparent to those skilled in the art with respect to replacement by ethenyl and ethynyl.

Thus, replacement as permitted herein results in the term "$C_1$-$C_{15}$ alkyl" as defined in connection with Formula I encompassing groups such as, but not limited to:

amino, hydroxy, phenyl, benzyl, propylaminoethoxy, butoxyethylamino, pyrid-2-ylpropyl, diethylaminomethyl, pentylsulfonyl, methylsulfonamidoethyl, 3-[4-(butylpyrimidin-2-yl)ethyl]phenyl, butoxy, dimethylamino, 4-(2-(benzylamino)ethyl)pyridyl, but-2-enylamino, 4-(1-(methylamino)pent-3-en-2-ylthio)phenyl, 2-(N-methyl-hexanamido)ethoxy)methyl, and 4-(((3-methoxy-4-(4-methyl-1H-imidazol-2-yl)but-1-enyl)(methyl)amino)-methyl)phenyl.

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The term "alkoxy" represents an alkyl group of indicated number of carbon atoms attached to the parent molecular moiety through an oxygen bridge. Examples of alkoxy groups include, for example, methoxy, ethoxy, propoxy and isopropoxy.

As used herein, the term "alkyl" means a straight or branched chain hydrocarbon containing from 1 to 14 carbons (unless otherwise noted). Examples of "alkyl" include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, undecyl, dodecyl, tridecyl, and the like.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenoxy" refers to an alkenyl group attached to the parent group through an oxygen atom.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl, naphthyl, and anthracenyl. More preferred aryl groups are phenyl and naphthyl. Most preferred is phenyl. The aryl groups of the invention may be substituted with various groups as provided herein. Thus, any carbon atom present within an aryl ring system and available for substitution may be further bonded to a variety of ring substituents, such as, for example, halogen, hydroxy, nitro, cyano, amino, $C_1$-$C_8$alkyl, $C_1$-$C_8$alkoxy, mono- and di($C_1$-$C_8$alkyl)amino, $C_3$-$C_{10}$cycloalkyl, ($C_3$-$C_{10}$cycloalkyl)alkyl, ($C_3$-$C_{10}$cycloalkyl)alkoxy, $C_2$-$C_9$heterocycloalkyl, $C_1$-$C_8$alkenyl, $C_1$-$C_8$alkynyl, halo($C_1$-$C_8$)alkyl, halo($C_1$-$C_8$)alkoxy, oxo, amino($C_1$-$C_8$)alkyl, mono- and di($C_1$-$C_8$alkyl)amino($C_1$-$C_8$)alkyl, $C_1$-$C_8$acyl, $C_1$-$C_8$acyloxy, $C_1$-$C_8$sulfonyl, $C_1$-$C_8$thio, $C_1$-$C_8$sulfonamido, $C_1$-$C_8$aminosulfonyl.

An "arylalkyl" group comprises an aryl group covalently attached to an alkyl group, either of which independently is optionally substituted. Preferably, the aralkyl group is aryl ($C_1$-$C_6$)alkyl, including, without limitation, benzyl, phenethyl, and naphthylmethyl.

The term "carboxy" as used herein, means a —$CO_2H$ group.

The term "cycloalkyl" refers to a monocyclic or a bicyclic cycloalkyl ring system. Monocyclic ring systems are cyclic hydrocarbon groups containing from 3 to 8 carbon atoms, where such groups can be saturated or unsaturated, but not aromatic. Examples of cycloalkyl include cyclopropyl, cyclobutyl, cyclopentyl, cyclohexyl, cycloheptyl and cyclooctyl. More preferred are $C_3$-$C_6$ cycloalkyl groups. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring.

The terms "halogen" or "halo" indicate fluorine, chlorine, bromine, and iodine.

The term "haloalkoxy" refers to an alkoxy group substituted with one or more halogen atoms, where each halogen is independently F, Cl, Br or I. Preferred halogens are F and Cl. Preferred haloalkoxy groups contain 1-6 carbons, more preferably 1-4 carbons, and still more preferably 1-2 carbons. "Haloalkoxy" includes perhaloalkoxy groups, such as $OCF_3$ or $OCF_2CF_3$. A preferred haloalkoxy group is trifluoromethoxy, difluoromethoxy, and fluoromethoxy.

The term "haloalkyl" refers to an alkyl group substituted with one or more halogen atoms, where each halogen is independently F, Cl, Br or I. Preferred halogens are F and Cl. Preferred haloalkyl groups contain 1-6 carbons, more preferably 1-4 carbons, and still more preferably 1-2 carbons. "Haloalkyl" includes perhaloalkyl groups, such as $CF_3$, $CHF_2$, $CH_3F$, or $CF_2CF_3$. A preferred haloalkyl group is trifluoromethyl, difluoromethy, and fluoromethyl.

The terms "heterocyclyl", "heterocycle" and "heterocycloalkyl" as used herein, mean a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl(thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a benzo ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. Preferred examples of heteroaryl groups include thienyl, benzothienyl, pyridyl, quinolyl, pyrazolyl, pyrimidyl, imidazolyl, benzimidazolyl, furanyl, benzofuranyl, dibenzofuranyl, thiazolyl, benzothiazolyl, isoxazolyl, oxadiazolyl, isothiazolyl, benzisothiazolyl, triazolyl, pyrrolyl, indolyl, pyrazolyl, and benzopyrazolyl.

The term "saturated" as used herein means the referenced chemical structure does not contain any multiple carbon-carbon bonds. For example, a saturated cycloalkyl group as defined herein includes cyclohexyl, cyclopropyl, and the like.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more" substituents, as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Pharmaceutically acceptable salt" refers to both acid and base addition salts.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Modulating" or "modulate" refers to the treating, prevention, suppression, enhancement or induction of a function, condition or disorder. For example, it is believed that the compounds of the present disclosure can modulate atherosclerosis by stimulating the removal of cholesterol from atherosclerotic lesions in a human.

"Treating" or "treatment" as used herein covers the treatment of a disease or disorder described herein, in a subject, preferably a human, and includes:
   i. inhibiting a disease or disorder, i.e., arresting its development;
   ii. relieving a disease or disorder, i.e., causing regression of the disorder;
   iii. slowing progression of the disorder; and/or
   iv. inhibiting, relieving, ameliorating, or slowing progression of one or more symptoms of the disease or disorder "Subject" refers to a warm blooded animal such as a mammal, preferably a human, or a human child, which is afflicted with, or has the potential to be afflicted with one or more diseases and disorders described herein.

"$EC_{50}$" refers to a dosage, concentration or amount of a particular test compound that elicits a dose-dependent response at 50% of maximal expression of a particular response that is induced, provoked or potentiated by the particular test compound.

"$IC_{50}$" refers to an amount, concentration or dosage of a particular test compound that achieves a 50% inhibition of a maximal response in an assay that measures such response.

The disclosures of all articles and references mentioned in this application, including patents, are incorporated herein by reference in their entirety.

EXAMPLES

Methods of Preparation

The compounds of the present disclosure may be prepared by use of known chemical reactions and procedures. Representative methods for synthesizing compounds of the disclosure are presented below. It is understood that the nature of the substituents required for the desired target compound often determines the preferred method of synthesis. All variable groups of these methods are as described in the generic description if they are not specifically defined below.

General Procedure

Those having skill in the art will recognize that the starting materials and reaction conditions may be varied, the sequence of the reactions altered, and additional steps employed to produce compounds encompassed by the present disclosure, as demonstrated by the following examples. Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Starting materials can be obtained from commercial sources or prepared by well-established literature methods known to those of ordinary skill in the art. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

In some cases, protection of certain reactive functionalities may be necessary to achieve some of the above transformations. In general, the need for such protecting groups as well as the conditions necessary to attach and remove such groups will be apparent to those skilled in the art of organic synthesis. An authoritative account describing the many alternatives to the trained practitioner are J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4.sup.th edition, Vol. 15/I, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

Synthetic procedures for preparing various 4-(4-oxo-4,5, 6,7-tetrahydro-1H-indazol-1-yl)benzamides are described in WO2008/130879 A2 and WO2006/091963.

The methods of the disclosure are illustrated further by the following examples, which are not to be construed as limiting the disclosure in scope or spirit to the specific procedures and in them. It is understood that the nature of the substituents required for the desired target compound often determines the preferred method of synthesis.

Example 1

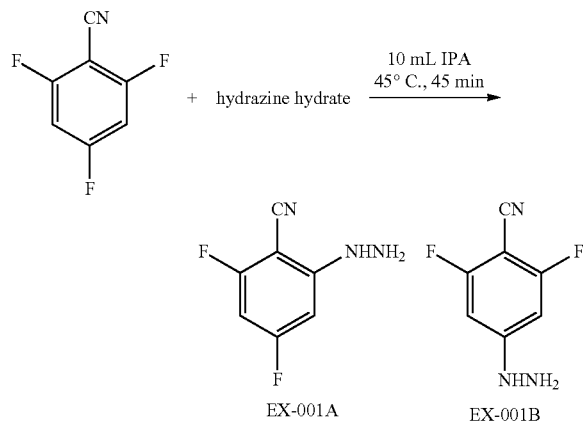

A stirred, ice cooled solution/suspension of 2,4,6-trifluorobenzonitrile (1.57 g, 10 mmol) in isopropanol (10 mL) under nitrogen was treated dropwise with hydrazine hydrate (1.02 mL, 21 mmol) and warmed to 45° C. for 45 min, then cooled to room temperature. The suspension was filtered and the solid EX-001A, amount not determined) rinsed with isopropanol. The filtrate was concentrated in vacuo at 50° C. and the residual solid partitioned between water and ethyl acetate (20 mL each). The layers were separated and the aqueous extracted with ethyl acetate (20 mL). The combined organic extracts were washed with brine (10 mL), dried (MgSO$_4$), and concentrated in vacuo. Recrystallization (2 crops) from ethyl acetate/heptane afforded pure (by TLC) EX-001B (0.45 g) as a white solid. Concentrated mother liquor afforded a 5:2 mixture of 001B:001A (0.32 g), which could be separated chromatographically using 2:1 heptane/EtOAc, then 1:1 heptane/EtOAc. Total amount of 001B available=0.68 g (40%). TLC: 1:1 ethyl acetate/heptane; rf 001A=0.50; rf 001B=0.25.

Example 2

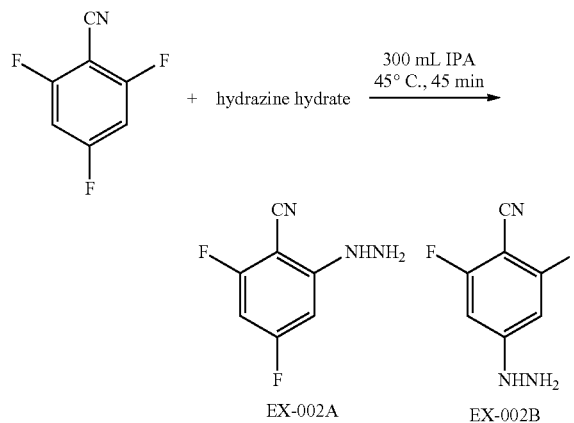

A stirred, ice cooled solution/suspension of 2,4,6-trifluorobenzonitrile (47.13, 300 mmol) in isopropanol (300 mL) under nitrogen was treated dropwise with hydrazine hydrate (30.6 mL, 630 mmol) and warmed to 45° C. for 45 min, then cooled to room temperature. The suspension was filtered and the solid rinsed several times with chilled (15° C.) isopropanol (solid 002A saved). The filtrate was concentrated in vacuo and the residue partitioned between ethyl acetate (400 mL) and water (250 mL). The organic layer was separated and the aqueous extracted with ethyl acetate (2×100 mL). The combined organic solution was washed with brine (200 mL), dried (MgSO$_4$), filtered and concentrated in vacuo to a white solid, which was highly enriched with EX-002B. This was recrystallized (2 crops) from ethyl acetate/heptane, then the mother liquor was concentrated in vacuo and the residual solid was taken up in isopropanol, stirred a few minutes, filtered (solid 002A saved), and the filtrate concentrated in vacuo and the residual solid (highly enriched in EX-002B) recrystallized (2 crops) from ethyl acetate/heptane. At this point the mother liquor contained 3-amino-4,6-diflouroindazole byproduct and too little desired product and very little mass, and so was discarded. Yield of 002A was 28.38 g (56%) as fine white needles; yield of 002B was 20.27 g (40%) as a white powder; 95% pure by NMR (rest=002A). EX-002A: $^1$H NMR (400 MHz, DMSO-d$_6$): δ 8.17 (s, 1H), 6.75 (dd, 1H), 6.54 (td, 1H), 4.47 (s, 1H); EX-002B: $^1$H NMR (400 MHz, DMSO-d$_6$): δ 8.51 (br s, 1H), 6.51 (br s, 2H), 4.54 (s, 1H).

Example 3

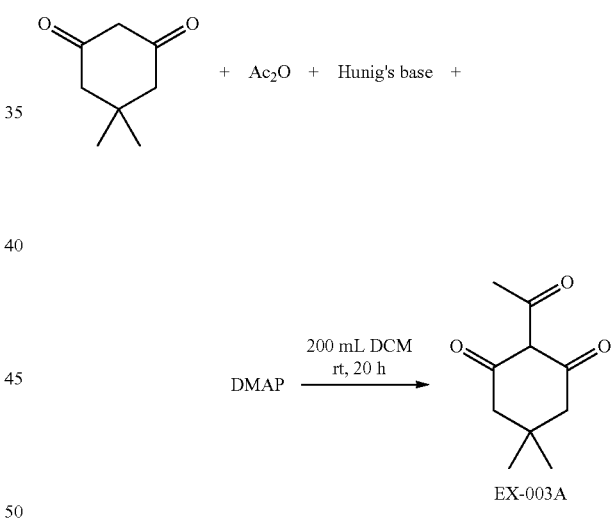

Dimedone (28.04 g, 200 mmol) and 4-(dimethylamino)pyridine (7.33 g, 60 mmol) were dissolved in dichloromethane (200 mL) and treated with N,N-diisopropylethylamine (25.85 g, 200 mmol). Acetic anhydride (20.04 mL, 212 mmol) was added dropwise, and the mixture stirred for 20 h and concentrated in vacuo. The residue was partitioned between heptane (300 mL) and 1N HCl (200 mL), and the acid layer extracted with heptane (100 mL). The combined organic solution was washed with water and brine (100 mL each), then treated with DARCO charcoal and MgSO$_4$, and stirred for 1 h. The mixture was filtered through Celite™, the solid rinsed with heptane, and the filtrate concentrated in vacuo to afford 33.38 g (92%) of EX-003A as an orange crystalline solid. $^1$H NMR (400 MHz, CDCl$_3$): δ 2.61 (s, 3H), 2.54 (s, 2H), 2.36 (s, 2H), 1.08 (s, 6H).

Example 4

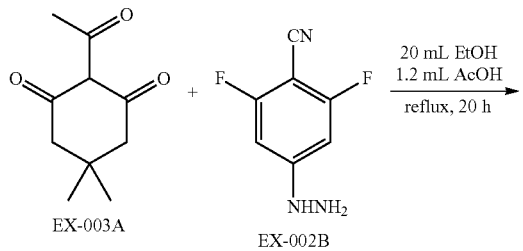

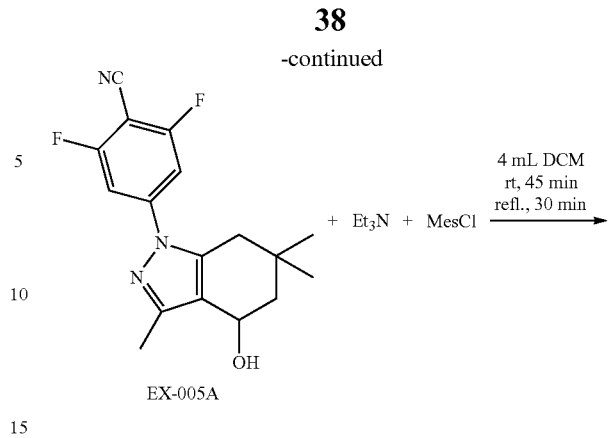

A stirred mixture of EX-003A (2.37 g, 13 mmol) and EX-002B (2.20 g, 13 mmol) in ethanol (20 mL) under nitrogen was treated with glacial acetic acid (1.2 mL) and heated to reflux for 20 h, then cooled on an ice bath. The mixture solidified, and this was diluted with enough acetonitrile to permit stirring, then filtered and the filter cake washed with acetonitrile and set aside. The filtrate was concentrated in vacuo and the residue triturated with ether and combined with the above filter cake and dried to afford 3.885 g (95%) of EX-004A (2,6-difluoro-4-(3,6,6-trimethyl-4-oxo-4,5,6,7-tetrahydro-1H-indazol-1-yl)benzonitrile) as a pale beige solid. $^1$H NMR (400 MHz, CDCl$_3$): δ 7.34 (d, 2H), 2.90 (s, 2H), 2.53 (s, 3H), 2.433 (s, 2H), 1.15 (s, 6H).

Example 5

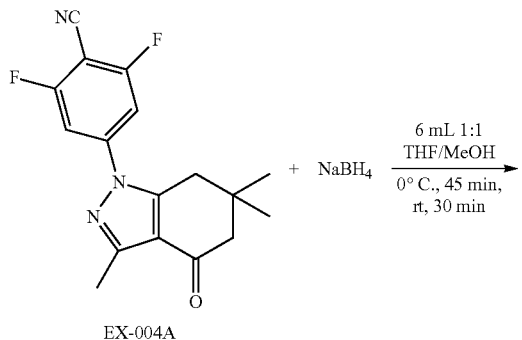

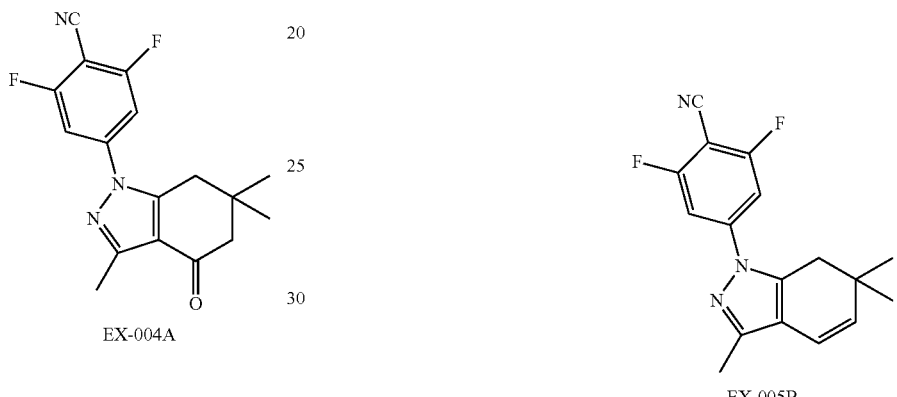

An ice cooled stirred solution of EX-004A (315 mg, 1.0 mmol) in 1:1 THF/MeOH (6 mL) under nitrogen was treated with sodium borohydride (114 mg, 3 mmol) and stirred for 45 min, then allowed to warm to room temperature and stirred an additional 30 min. Water (3 mL) was added, and the mixture concentrated in vacuo to remove THF and methanol and diluted with more water (15 mL). The suspension was stirred a few minutes, filtered, the solid rinsed with water, collected, and dried in vacuo to afford EX-005A (2,6-difluoro-4-(4-hydroxy-3,6,6-trimethyl-4,5,6,7-tetrahydro-1H-indazol-1-yl)benzonitrile) (311 mg) as a white powder. This was dissolved in anh. DCM (4 mL) and cooled on an ice bath under nitrogen and treated with triethylamine (0.28 mL). The stirred mixture was treated dropwise with methanesulfonyl chloride (0.085 mL), warmed to room temperature, and stirred 30 min. Reaction was still very incomplete by TLC (10% EtOAc/DCM), so additional triethylamine (0.14 mL) and methanesulfonyl chloride (0.04 mL) were added and the solution heated to reflux for 30 min. At this point only a little 005A remained, so the mixture was concentrated in vacuo and the residue partitioned between ethyl acetate (15 mL) and water (10 mL). The organic layer was set aside and the aqueous extracted with ethyl acetate (10 mL). The combined organic solution was dried (MgSO$_4$) and concentrated in vacuo, and the residual solid dissolved in 4:1 DCM/heptane, loaded onto a silica gel column (~150 cc), and eluted with 4:1 DCM/heptane to afford 236 mg (79% for two steps) of EX-005B (2,6-difluoro-4-(3,6,6-trimethyl-6,7-dihydro-1H-indazol-1-yl)benzonitrile) as a white solid.

Example 6

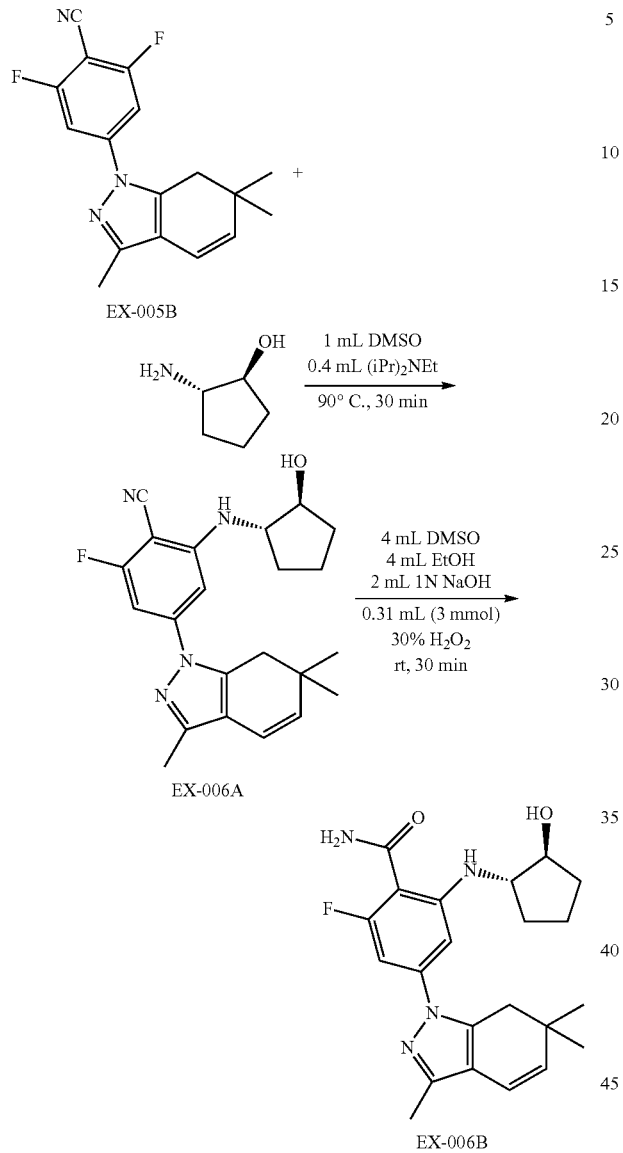

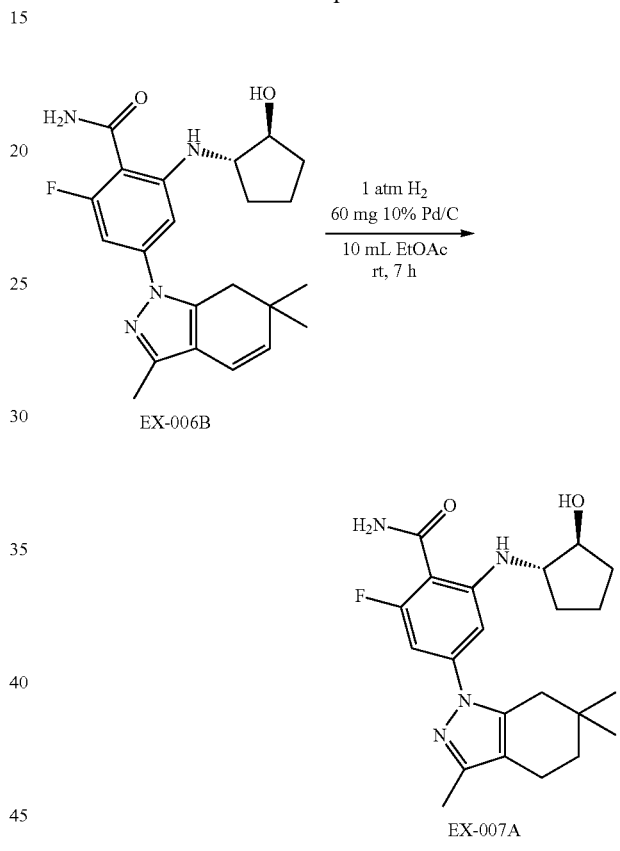

A stirred solution of trans-(1S,2S)-2-aminocyclopentanol hydrochloride (358 mg, 2.6 mmol) in methanol (5 mL) was treated with DOWEX 550A-OH resin (4 g, freshly washed with methanol), stirred a few minutes, filtered, and the filtrate concentrated in vacuo to a viscous oil free base in a 50 mL round bottom flask. EX-005B (0.599 g, 2.0 mmol) was added, followed by DMSO (1 mL) and Hunig's base (0.4 mL), and the mixture was stirred for 30 min at 90° C. under nitrogen. Water (30 mL) was added, and the suspension stirred a few minutes and filtered and the gummy solid rinsed with water, collected, and air dried overnight. Intermediate EX-006A (2-fluoro-6-((1S,2S)-2-hydroxycyclopentylamino)-4-(3,6,6-trimethyl-6,7-dihydro-1H-indazol-1-yl)benzonitrile) was dissolved in DMSO (4 mL) and ethanol (4 mL), treated with 1N NaOH (2 mL), then dropwise with 30% hydrogen peroxide (0.31 mL, 3 mmol), and stirred for 30 min at room temperature. Water (50 mL) was added, the mixture stirred a few minutes, then filtered and the solid rinsed with water and air dried overnight. This was dissolved in dichloromethane and added to a silica gel column (~70 cc) and eluted with 2:1 DCM/EtOAc, then 1:1 DCM/EtOAc to afford 763 mg (96% for 2 steps) of EX-006B (2-fluoro-6-((1S,2S)-2-hydroxycyclopentylamino)-4-(3,6,6-trimethyl-6,7-dihydro-1H-indazol-1-yl)benzamide) as a white foam. $^1$H NMR (400 MHz, CDCl$_3$): δ 8.74 (br s, 1H), 6.66 (d, 1H), 6.60 (d, 1H), 6.43 (dd, 1H), 6.16 (d, 1H), 5.55 (br, 1H), 5.38 (d, 1H), 4.07 (m, 1H), 3.62 (br s, 1H), 2.77 (s, 2H), 2.30 (br, 1H), 2.23 (s, 4H), 1.94 (m, 1H), 1.73 (m, 2H), 1.59 (m, 1H), 1.51 (m, 1H), 1.03 (s, 6H).

Example 7

A stirred solution of EX-006B (398 mg, 1.0 mmol) in ethyl acetate (10 mL) in a 50 mL 1-neck round bottom flask under nitrogen was treated with 10% Pd/C and evacuated and filled with hydrogen via balloon several times, then stirred under hydrogen for 7 h. The hydrogen was evacuated and replaced with nitrogen, and the solution was carefully filtered through Celite® (care taken not to let filter cake dry) and the filtrate concentrated in vacuo to afford 0.42 g of a white foam EX-007A (2-fluoro-6-((1S,2S)-2-hydroxycyclopentylamino)-4-(3,6,6-trimethyl-4,5,6,7-tetrahydro-1H-indazol-1-yl)benzamide). MS (M+1, Advion): 401.65. $^1$H NMR (400 MHz, CDCl$_3$): δ 8.77 (d, 1H), 6.73 (d, 1H), 6.68 (d, 1H), 6.53 (dd, 1H), 5.78 (br, 1H), 4.15 (m, 1H), 3.68 (m, 1H), 3.05 (br s, 1H), 2.57 (s, 2H), 2.45 (t, 2H), 2.24 (s, 4H), 2.01 (m, 1H), 1.80 (m, 2H), 1.65 (m, 1H), 1.57 (m, 3H), 1.01 (s, 6H); $^{13}$C NMR (400 MHz, CDCl$_3$): δ 169.00, 164.75, 162.82, 152.91, 148.40, 144.20, 144.06, 139.56, 116.23, 101.23, 98.73, 96.23, 95.98, 35.51, 35.87, 33.76, 31.64, 31.20, 28.29, 22.07, 17.98, 12.20.

Example 8

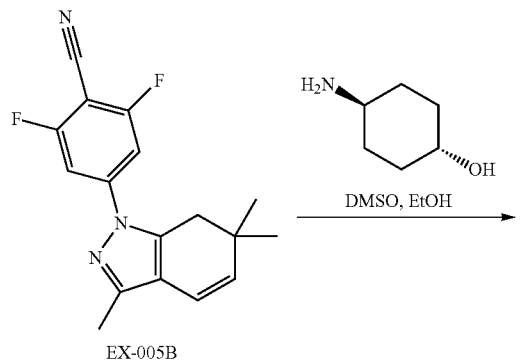

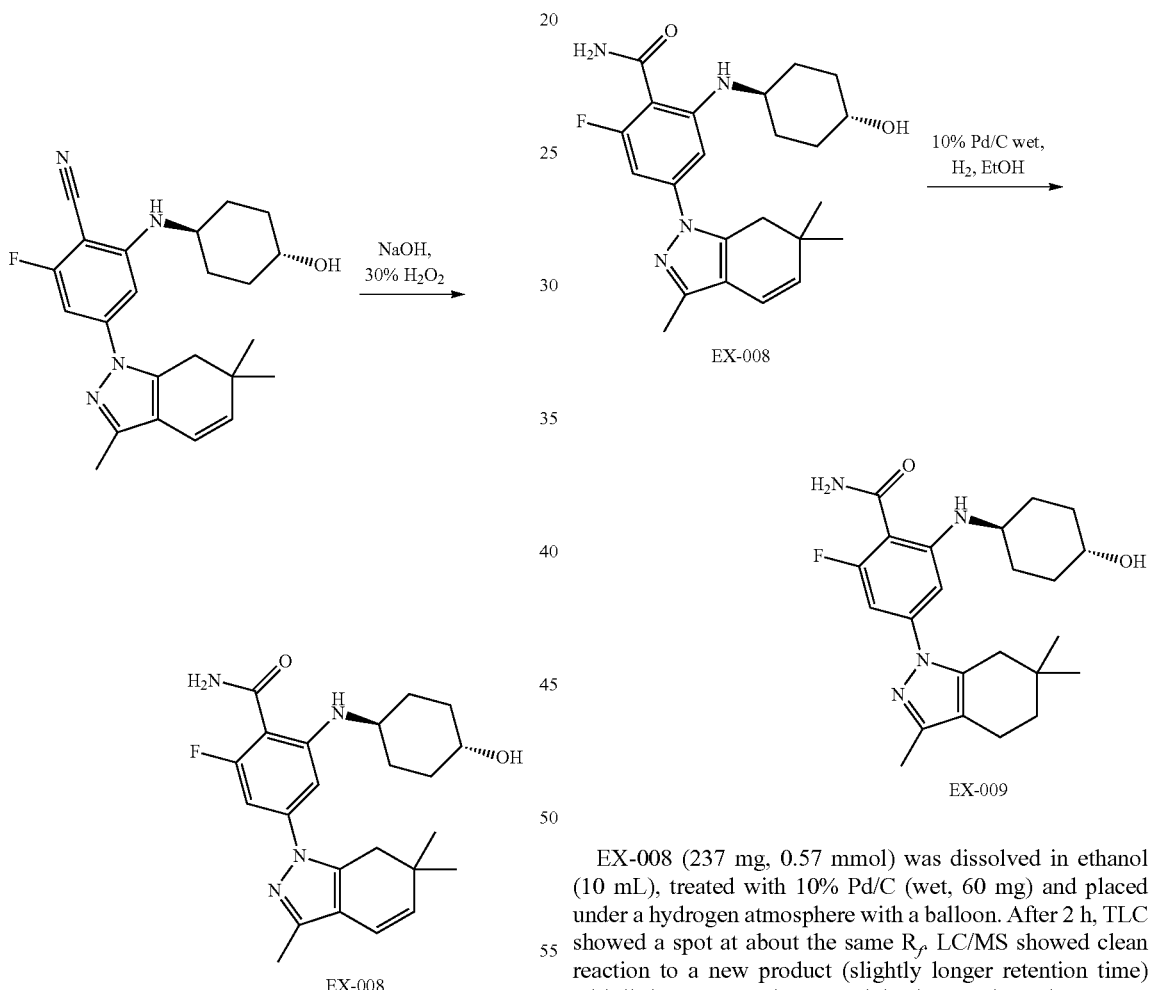

EX-005B (245 mg, 0.82 mmol) and trans-4-hydroxycyclohexylamine (236 mg, 2.0 mmol) were combined and dissolved in 4:1, EtOH:DMSO (4 mL) and heated to 70° C. for 1 h. TLC shows partial reaction so the temperature was increased to 80° C. for an hour. TLC shows starting material, so the ethanol was rotavapped off and the reaction mixture was heated at 110° C. for 1 h. TLC and LC/MS show complete reaction. The mixture was allowed to cool a bit and was treated with 25% sodium hydroxide solution (50 µL), followed by dropwise addition of 30% hydrogen peroxide solution (50 µL). TLC showed partial reaction, so more base and peroxide were added (50 µL ea.) and the mixture diluted with ethanol (1 mL) and heated to 70° C. for an hour. TLC showed complete reaction. The reaction mixture was partitioned between water and an ethyl acetate-DCM mixture and the organic layer removed and concentrate. The residue was dissolved in hot DCE (3 mL) which was loaded onto a column and chromatographed (Biotage 12 mm, 30 to 100% ethyl acetate in hexanes over 16 CV). Substantial crystals formed in fraction 2 so this was filtered off to give EX-008 (2-fluoro-6-((1r,4r)-4-hydroxycyclohexylamino)-4-(3,6,6-trimethyl-6,7-dihydro-1H-indazol-1-yl)benzamide) (100 mg, 29%) as a white fluffy crystalline solid.

Example 9

EX-008 (237 mg, 0.57 mmol) was dissolved in ethanol (10 mL), treated with 10% Pd/C (wet, 60 mg) and placed under a hydrogen atmosphere with a balloon. After 2 h, TLC showed a spot at about the same $R_f$, LC/MS showed clean reaction to a new product (slightly longer retention time) with little or no starting material. The reaction mixture was placed under a slow nitrogen stream over the weekend. The dried up reaction mixture was redissolved in ethanol/ethyl acetate and filtered through Celite then concentrated to a white solid. The solid was dissolved in hot DCE (2 or 3 mL) and added to a column and chromatographed (Biotage 12 mm, 0 to 50 then 50 to 100% ethyl acetate in hexanes over 16 CV). Active fractions 6-12 were combined to give a white crystalline solid of EX-009 (2-fluoro-6-((1r,4r)-4-hydroxycyclohexylamino)-4-(3,6,6-trimethyl-4,5,6,7-tetrahydro-1H-indazol-1-yl)benzamide) (208 mg).

Example 10

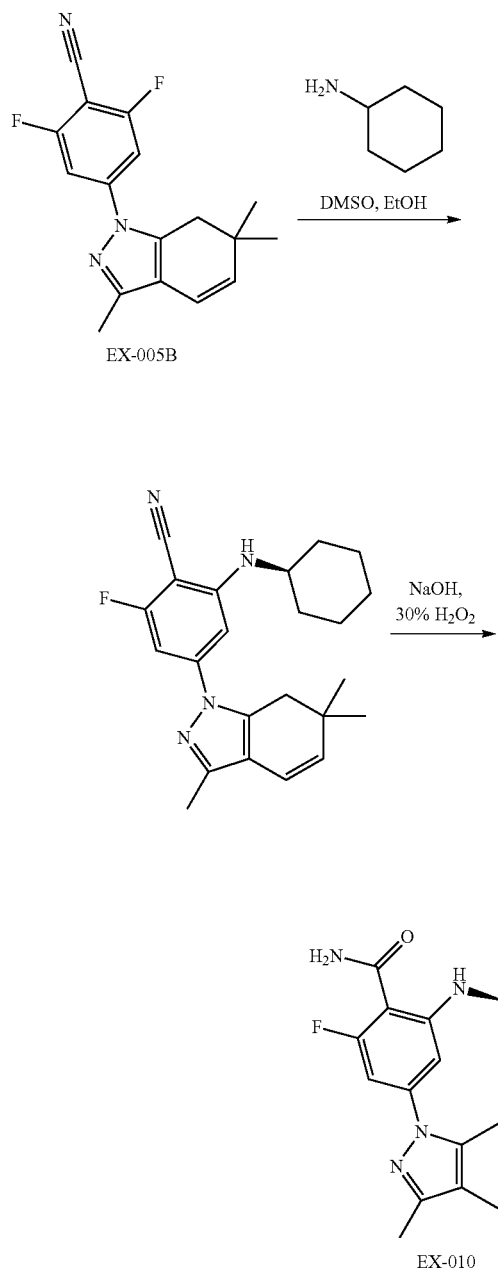

EX-005B (150 mg 75 mg ea., 0.50 mmol) and cyclohexylamine (124 mg, 1.25 mmol) were combined in DMSO (1 mL) and heated gently with a heat gun to dissolve everything. TLC of the sample showed complete reaction. The mixture was diluted with ethanol (4 mL) and treated with 25% sodium hydroxide solution (50 μL), followed by dropwise addition of 30% hydrogen peroxide solution (50 μL). TLC showed partial reaction, so more base and peroxide were added (50 μL ea.) and the mixture stirred for an hour. TLC showed complete reaction. The mixture was stirred over the weekend then diluted with water (5 mL), concentrated to remove ethanol, and extracted with DCE (2×2 mL). The DCE fractions were loaded onto a column and chromatographed (Biotage 12 mm, 10 to 50% ethyl acetate in hexanes over 16 CV). Fractions 3 and 4 were combined and concentrated to give a white crystaline solid (150 mg). The solid was triturated with hexanes and the crystals were filtered off to give EX-010 (2-(cyclohexylamino)-6-fluoro-4-(3,6,6-trimethyl-6,7-dihydro-1H-indazol-1-yl)benzamide) (124 mg, 62%) as a white crystaline solid.

Example 11

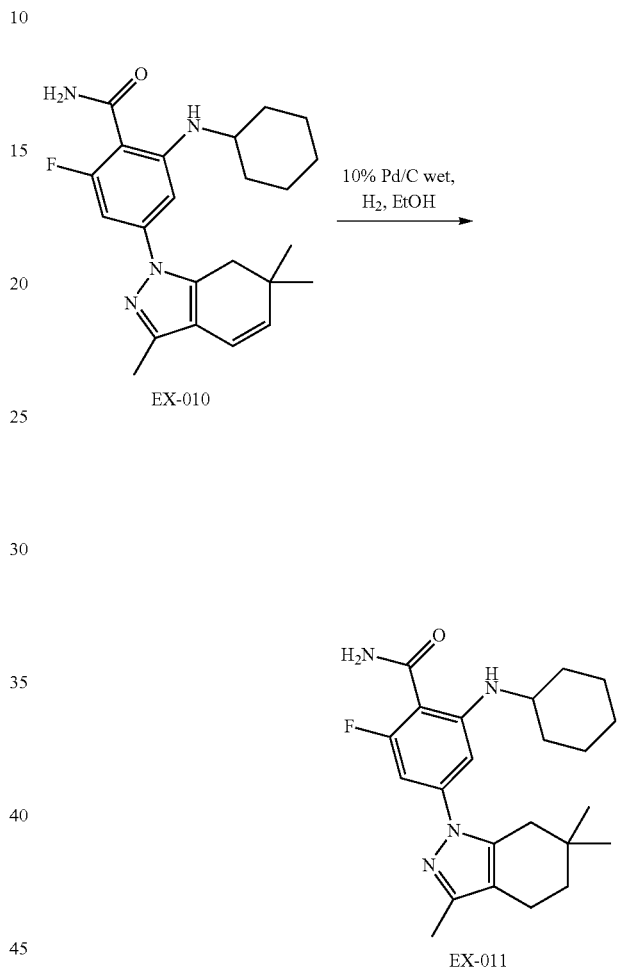

EX-010 (75 mg, 189 umol) was dissolved in ethanol (5 mL) and ethyl acetate (2 mL), treated with 10% Pd/C (wet, 10 mg) and placed under a hydrogen atmosphere and stirred vigorously for 2 days. LC/MS of an aliquot showed complete reaction. The atmosphere was replaced with nitrogen and mixture was heated a bit to insure solution and then filtered through Celite to remove the catalysts. The solution was concentrated to a solid then triturated with hexanes. The product was filtered off to give EX-011 (2-(cyclohexylamino)-6-fluoro-4-(3,6,6-trimethyl-4,5,6,7-tetrahydro-1H-indazol-1-yl)benzamide) (67 mg, 88%) as a white solid.

Examples 12-17

Examples 12-17 shown below in Table 1, were prepared essentially according to the synthetic methodology described herein, and/or by using methodology described in the art. See, for example, WO2008/130879 A2 and WO2006/091963 A1.

TABLE 1

| Example (Compound no.) | Structure | Nomenclature |
|---|---|---|
| 12 EX-012 | 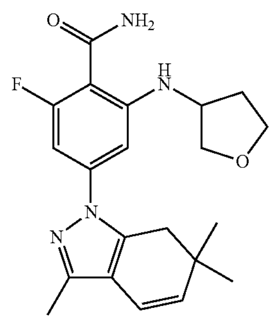 [SMILES: Cc1nn(-c2cc(F)c(C(N)=O)c(NC3CCOC3)c2)c2c1C=CC(C)(C)C2] | 2-fluoro-6-(tetrahydrofuran-3-ylamino)-4-(3,6,6-trimethyl-6,7-dihydro-1H-indazol-1-yl)benzamide |
| 13 EX-013 | 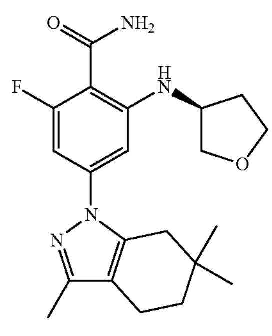 [SMILES: Cc1nn(-c2cc(F)c(C(N)=O)c(N[C@H]3CCOC3)c2)c2c1CCC(C)(C)C2] | (S)-2-fluoro-6-(tetrahydrofuran-3-ylamino)-4-(3,6,6-trimethyl-4,5,6,7-tetrahydro-1H-indazol-1-yl)benzamide |
| 14 EX-014 | 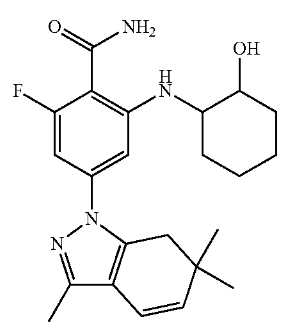 [SMILES: Cc1nn(-c2cc(F)c(C(N)=O)c(NC3CCCCC3O)c2)c2c1C=CC(C)(C)C2] | 2-fluoro-6-((1R,2R)-2-hydroxycyclohexylamino)-4-(3,6,6-trimethyl-6,7-dihydro-1H-indazol-1-yl)benzamide |

TABLE 1-continued

| Example (Compound no.) | Structure | Nomenclature |
|---|---|---|
| 15 EX-015 | 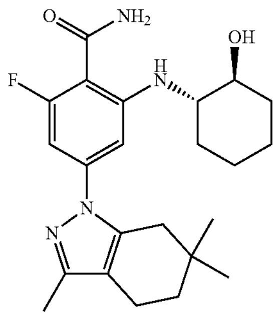 [SMILES: Cc1nn(-c2cc(F)c(C(N)=O)c(N[C@H]3CCCC[C@@H]3O)c2)c2c1CCC(C)(C)C2] | 2-fluoro-6-((1S,2S)-2-hydroxycyclohexylamino)-4-(3,6,6-trimethyl-4,5,6,7-tetrahydro-1H-indazol-1-yl)benzamide |
| 16 EX-016 | 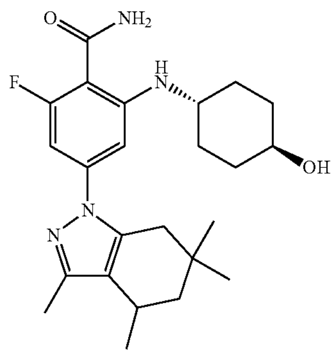 [SMILES: Cc1nn(-c2cc(F)c(C(N)=O)c(N[C@H]3CC[C@H](O)CC3)c2)c2c1C(C)CC(C)(C)C2] | 2-fluoro-6-((1R,4R)-4-hydroxycyclohexylamino)-4-(3,4,6,6-tetramethyl-4,5,6,7-tetrahydro-1H-indazol-1-yl)benzamide |
| 17 EX-017 | 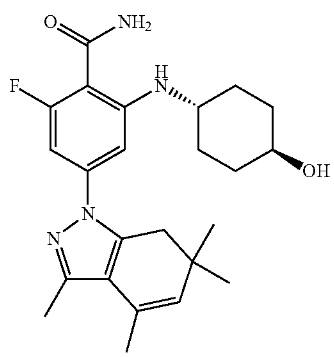 [SMILES: CC1=CC(C)(C)Cc2c1c(C)nn2-c1cc(F)c(C(N)=O)c(N[C@H]2CC[C@H](O)CC2)c1] | 2-fluoro-6-((1R,4R)-4-hydroxycyclohexylamino)-4-(3,4,6,6-tetramethyl-6,7-dihydro-1H-indazol-1-yl)benzamide |

Example 18

Examples 18-268, shown below in Table 1A, are prepared essentially according to the synthetic methodology described herein, Examples 1-11, methodology described in the art, and/or procedures described in WO2008/130879 A2 and WO2006/091963.

TABLE 1A

| Compound (EX-) number | Compound Name |
|---|---|
| 18 | 2-(trans-4-(cyclopropylmethylamino)cyclohexylamino)-4-(6,6-dimethyl-3-(trifluoromethyl)-4,5,6,7-tetrahydro-1H-indazol-1-yl)benzamide |

TABLE 1A-continued

| Compound (EX-) number | Compound Name |
|---|---|
| 19 | |

TABLE 1A-continued

| Compound (EX-) number | Compound Name |
|---|---|
| 20 | 2,6-difluoro-4-(4-hydroxy-6,6-dimethyl-3-(trifluoromethyl)-4,5,6,7-tetrahydro-1H-indazol-1-yl)benzonitrile 4-(6,6-dimethyl-3-(trifluoromethyl)-6,7-dihydro-1H-indazol-1-yl)-2,6-difluorobenzonitrile |
| 21 | 4-(3-ethyl-4-hydroxy-6,6-dimethyl-4,5,6,7-tetrahydro-1H-indazol-1-yl)-2,6-difluorobenzonitrile |
| 22 | 4-(3-ethyl-6,6-dimethyl-6,7-dihydro-1H-indazol-1-yl)-2,6-difluorobenzonitrile |
| 23 | 2-fluoro-6-(trans-4-methoxycyclohexylamino)-4-(3,6,6-trimethyl-4,5,6,7-tetrahydro-1H-indazol-1-yl)benzamide |
| 24 | 2-(trans-4-hydroxycyclohexylamino)-4-(3-(hydroxymethyl)-6,6-dimethyl-4,5,6,7-tetrahydro-1H-indazol-1-yl)benzamide |
| 25 | 4-(3-Ethyl-6,6-dimethyl-4,5,6,7-tetrahydro-indazol-1-yl)-2,3-difluoro-benzonitrile |
| 26 | 4-(3-ethyl-6,6-dimethyl-4,5,6,7-tetrahydro-1H-indazol-1-yl)-3-fluoro-2-((1S,2S)-2-hydroxycyclohexylamino)benzamide |
| 27 | 4-(3-Ethyl-6,6-dimethyl-4,5,6,7-tetrahydro-indazol-1-yl)-2,3,5,6-tetrafluoro-benzonitrile |
| 28 | 4-(3-ethyl-6,6-dimethyl-4,5,6,7-tetrahydro-1H-indazol-1-yl)-2,3,5-trifluoro-6-(trans-4-hydroxycyclohexylamino)benzamide |
| 29 | 2-fluoro-6-(2-oxoazepan-3-ylamino)-4-(3,6,6-trimethyl-4,5,6,7-tetrahydro-1H-indazol-1-yl)benzamide |
| 30 | 2-(1-(2-hydroxyethyl)-1H-pyrazol-4-ylamino)-4-(3,6,6-trimethyl-4,5,6,7-tetrahydro-1H-indazol-1-yl)benzamide |
| 31 | 2-(1-(2-(isobutylamino)ethyl)-1H-pyrazol-4-ylamino)-4-(3,6,6-trimethyl-4,5,6,7-tetrahydro-1H-indazol-1-yl)benzamide |
| 32 | 2-(1,3-dihydroxypropan-2-ylamino)-6-fluoro-4-(3,6,6-trimethyl-4,5,6,7-tetrahydro-1H-indazol-1-yl)benzamide |
| 33 | 4-(3-Cyclopropylmethyl-6,6-dimethyl-4,5,6,7-tetrahydroindazol-1-yl)-2,5-difluorobenzonitrile |
| 34 | (R)-4-(3-(cyclopropylmethyl)-6,6-dimethyl-4,5,6,7-tetrahydro-1H-indazol-1-yl)-5-fluoro-2-(tetrahydrofuran-3-ylamino)benzamide |
| 35 | 4-(6,6-dimethyl-3-(pyridin-2-ylmethyl)-4,5,6,7-tetrahydro-1H-indazol-1-yl)-2-(tetrahydro-2H-pyran-4-ylamino)benzamide |
| 36 | 4-(3-Ethyl-6,6-dimethyl-4,5,6,7-tetrahydroindazol-1-yl)-2-fluorobenzonitrile |
| 37 | (S)-4-(3-ethyl-6,6-dimethyl-4,5,6,7-tetrahydro-1H-indazol-1-yl)-2-(tetrahydrofuran-3-ylamino)benzamide |

TABLE 1A-continued

| Compound (EX-) number | Compound Name |
|---|---|
| 38 | (S)-4-(6,6-dimethyl-3-(trifluoromethyl)-4,5,6,7-tetrahydro-1H-indazol-1-yl)-2-(piperidin-3-ylamino)benzamide |
| 39 | (S)-4-(6,6-dimethyl-3-(trifluoromethyl)-4,5,6,7-tetrahydro-1H-indazol-1-yl)-2-(1-neopentylpiperidin-3-ylamino)benzamide |
| 40 | 2-((1S,2S)-2-aminocyclohexylamino)-6-fluoro-4-(3,6,6-trimethyl-4,5,6,7-tetrahydro-1H-indazol-1-yl)benzamide |
| 41 | 2-fluoro-6-((1S,2S)-2-(neopentylamino)cyclohexylamino)-4-(3,6,6-trimethyl-4,5,6,7-tetrahydro-1H-indazol-1-yl)benzamide |
| 42 | 2-(2-(((1H-imidazol-2-yl)methylthio)ethylamino)-4-(3-ethyl-6,6-dimethyl-4,5,6,7-tetrahydro-1H-indazol-1-yl)-6-fluorobenzamide |
| 43 | 2-(cyclopent-3-enylamino)-6-fluoro-4-(3,6,6-trimethyl-4,5,6,7-tetrahydro-1H-indazol-1-yl)benzamide |
| 44 | (S)-4-(6,6-dimethyl-3-(trifluoromethyl)-4,5,6,7-tetrahydro-1H-indazol-1-yl)-2-(1-(prop-2-ynyl)pyrrolidin-3-ylamino)benzamide |
| 45 | 2-(cyclobutylamino)-4-(3-ethyl-6,6-dimethyl-4,5,6,7-tetrahydro-1H-indazol-1-yl)-6-fluorobenzamide |
| 46 | (R)-4-(6,6-dimethyl-3-(trifluoromethyl)-4,5,6,7-tetrahydro-1H-indazol-1-yl)-2-(2-hydroxypropylamino)benzamide |
| 47 | 2-(trans-4-aminocyclohexylamino)-4-(6,6-dimethyl-3-(trifluoromethyl)-4,5,6,7-tetrahydro-1H-indazol-1-yl)benzamide |
| 48 | 4-(3-ethyl-6,6-dimethyl-4,5,6,7-tetrahydro-1H-indazol-1-yl)-2-fluoro-6-(tetrahydro-2H-pyran-4-ylamino)benzamide |
| 49 | 2-fluoro-6-(tetrahydro-2H-pyran-4-ylamino)-4-(3,6,6-trimethyl-4,5,6,7-tetrahydro-1H-indazol-1-yl)benzamide |
| 50 | 2-fluoro-6-(((S)-tetrahydrofuran-3-yl)amino)-4-(4,6,6-trimethyl-3-(trifluoromethyl)-4,5,6,7-tetrahydro-1H-indazol-1-yl)benzamide |
| 51 | (S)-4-(6,6-dimethyl-3-(trifluoromethyl)-4,5,6,7-tetrahydro-1H-indazol-1-yl)-2-fluoro-6-((tetrahydrofuran-3-yl)amino)benzamide |
| 52 | 2-fluoro-6-(((1S,2S)-2-hydroxycyclopentyl)amino)-4-(3,4,6,6-tetramethyl-4,5,6,7-tetrahydro-1H-indazol-1-yl)benzamide |
| 53 | 4-(3-ethyl-6,6-dimethyl-4,5,6,7-tetrahydro-1H-indazol-1-yl)-2-fluoro-6-((1S,2S)-2-hydroxycyclopentylamino)benzamide |
| 54 | 4-(6,6-dimethyl-3-(trifluoromethyl)-4,5,6,7-tetrahydro-1H-indazol-1-yl)-2-fluoro-6-(((1r,4r)-4-hydroxycyclohexyl)amino)benzamide |
| 55 | 2-fluoro-6-(((1r,4r)-4-hydroxycyclohexyl)amino)-4-(4,6,6-trimethyl-3-(trifluoromethyl)-4,5,6,7-tetrahydro-1H-indazol-1-yl)benzamide |
| 56 | 4-(6,6-dimethyl-3-(trifluoromethyl)-6,7-dihydro-1H-indazol-1-yl)-2-fluoro-6-(((1r,4r)-4-hydroxycyclohexyl)amino)benzamide |
| 57 | 2-fluoro-6-(((1r,4r)-4-hydroxycyclohexyl)amino)-4-(4,6,6-trimethyl-3-(trifluoromethyl)-6,7-dihydro-1H-indazol-1-yl)benzamide |
| 58 | 4-(3-ethyl-6,6-dimethyl-4,5,6,7-tetrahydro-1H-indazol-1-yl)-2-fluoro-6-(trans-4-hydroxycyclohexylamino)benzamide |
| 59 | 4-(6,6-dimethyl-3-(trifluoromethyl)-4,5,6,7-tetrahydro-1H-indazol-1-yl)-2-((1S,2S)-2-hydroxycyclohexylamino)benzamide |
| 60 | 4-(6,6-dimethyl-3-(trifluoromethyl)-4,5,6,7-tetrahydro-1H-indazol-1-yl)-2-((1S,2S)-2-hydroxycyclopentylamino)benzamide |
| 61 | 4-(3-ethyl-6,6-dimethyl-4,5,6,7-tetrahydro-1H-indazol-1-yl)-2-((1S,2S)-2-hydroxycyclohexylamino)benzamide |
| 62 | 4-(3-ethyl-6,6-dimethyl-4,5,6,7-tetrahydro-1H-indazol-1-yl)-2-((1S,2S)-2-hydroxycyclopentylamino)benzamide |
| 63 | (S)-2-(tetrahydrofuran-3-ylamino)-4-(3,6,6-trimethyl-4,5,6,7-tetrahydro-1H-indazol-1-yl)benzamide |
| 64 | 2-((1S,2S)-2-hydroxycyclopentylamino)-4-(3,6,6-trimethyl-4,5,6,7-tetrahydro-1H-indazol-1-yl)benzamide |
| 65 | 2-((1S,2S)-2-hydroxycyclohexylamino)-4-(3,6,6-trimethyl-4,5,6,7-tetrahydro-1H-indazol-1-yl)benzamide |
| 66 | 2-(cyclopentylamino)-4-(3-ethyl-6,6-dimethyl-4,5,6,7-tetrahydro-1H-indazol-1-yl)-6-fluorobenzamide |
| 67 | (1S,2S)-2-(2-carbamoyl-5-(3-ethyl-6,6-dimethyl-4,5,6,7-tetrahydro-1H-indazol-1-yl)-3-fluorophenylamino)cyclopentyl 2-aminoacetate hydrochloride |
| 68 | (1S,2S)-2-(2-carbamoyl-3-fluoro-5-(3,6,6-trimethyl-4,5,6,7-tetrahydro-1H-indazol-1-yl)phenylamino)cyclopentyl 2-aminoacetate maleate |
| 69 | (trans)-4-(2-carbamoyl-5-(3-ethyl-6,6-dimethyl-4,5,6,7-tetrahydro-1H-indazol-1-yl)-3-fluorophenylamino)cyclohexyl 2-aminoacetate hydrochloride |
| 70 | trans-4-(2-carbamoyl-3-fluoro-5-(3,6,6-trimethyl-4,5,6,7-tetrahydro-1H-indazol-1-yl)phenylamino)cyclohexyl 2-aminoacetate methanesulfonate |
| 71 | 2-(cyclopentylamino)-6-fluoro-4-(3,6,6-trimethyl-4,5,6,7-tetrahydro-1H-indazol-1-yl)benzamide |
| 72 | 4-(6,6-dimethyl-3-(trifluoromethyl)-4,5,6,7-tetrahydro-1H-indazol-1-yl)-2-fluoro-6-((1S,2S)-2-hydroxycyclopentylamino)benzamide |
| 73 | (1S,2S)-2-(2-carbamoyl-5-(6,6-dimethyl-3-(trifluoromethyl)-4,5,6,7-tetrahydro-1H-indazol-1-yl)-3-fluorophenylamino)cyclopentyl 2-aminoacetate |
| 74 | 4-(6,6-dimethyl-3-(trifluoromethyl)-4,5,6,7-tetrahydro-1H-indazol-1-yl)-2-fluoro-6-(tetrahydro-2H-pyran-4-ylamino)benzamide |
| 75 | 4-(6,6-dimethyl-3-(trifluoromethyl)-4,5,6,7-tetrahydro-1H-indazol-1-yl)-2-fluoro-6-((1S,2S)-2-hydroxycyclohexylamino)benzamide |
| 76 | (1S,2S)-2-(2-carbamoyl-5-(6,6-dimethyl-3-(trifluoromethyl)-4,5,6,7-tetrahydro-1H-indazol-1-yl)-3-fluorophenylamino)cyclohexyl 2-aminoacetate methanesulfonate |
| 77 | (1S,2S)-2-(2-carbamoyl-5-(3-ethyl-6,6-dimethyl-4,5,6,7-tetrahydro-1H-indazol-1-yl)phenylamino)cyclohexyl 2-aminoacetate |
| 78 | (1S,2S)-2-(2-carbamoyl-5-(6,6-dimethyl-3-(trifluoromethyl)-4,5,6,7-tetrahydro-1H-indazol-1-yl)phenylamino)cyclopentyl 2-aminoacetate methanesulfonate |
| 79 | (1S,2S)-2-(2-carbamoyl-5-(6,6-dimethyl-3-(trifluoromethyl)-4,5,6,7-tetrahydro-1H-indazol-1-yl)phenylamino)cyclohexyl 2-aminoacetate methanesulfonate |
| 80 | 4-(3-ethyl-6,6-dimethyl-4,5,6,7-tetrahydro-1H-indazol-1-yl)-2-((1S,2S)-2-hydroxycyclopentylamino)-6 methoxybenzamide |
| 81 | 5-(6,6-dimethyl-3-(trifluoromethyl)-4,5,6,7-tetrahydro-1H-indazol-1-yl)-3-((trans)-4-hydroxycyclohexylamino)picolinamide |
| 82 | 4-(3-ethyl-6,6-dimethyl-4,5,6,7-tetrahydro-1H-indazol-1-yl)-2-fluoro-6-((1S,2S)-2-hydroxycyclopentylamino)benzamide |
| 83 | 2-(4,4-Difluoro-cyclohexylamino)-6-fluoro-4-(3,6,6-trimethyl-4,5,6,7-tetrahydro-indazol-1-yl)-benzamide |
| 84 | 2-(cyclohexylamino)-4-(6,6-dimethyl-3-(trifluoromethyl)-4,5,6,7-tetrahydro-1H-indazol-1-yl)-6-fluorobenzamide |
| 85 | trans-4-(2-carbamoyl-3-fluoro-5-(3,6,6-trimethyl-4,5,6,7-tetrahydro-1H-indazol-1-yl)phenylamino)cyclohexyl 2-(tert-butoxycarbonylamino)acetate |
| 86 | (1S,2S)-2-(2-carbamoyl-5-(6,6-dimethyl-3-(trifluoromethyl)-4,5,6,7-tetrahydro-1H-indazol-1-yl)phenylamino)cyclopentyl 2-(tert-butoxycarbonylamino)acetate |
| 87 | 4-(3-(cyclopropylmethyl)-6,6-dimethyl-4,5,6,7-tetrahydro-1H-indazol-1-yl)-2-fluoro-6-(tetrahydro-2H-pyran-4-ylamino)benzamide |
| 88 | 2-fluoro-6-(tetrahydro-2H-pyran-4-ylamino)-4-(3,6,6-trimethyl-4,5,6,7-tetrahydro-1H-indazol-1-yl)benzamide |
| 89 | 4-(3-ethyl-6,6-dimethyl-4,5,6,7-tetrahydro-1H-indazol-1-yl)-3-fluoro-2-(trans-4-hydroxycyclohexylamino)benzamide |
| 90 | (S)-2-fluoro-6-(tetrahydrofuran-3-ylamino)-4-(3,6,6-trimethyl-4,5,6,7-tetrahydro-1H-indazol-1-yl)benzamide§ |
| 91 | (R)-2-fluoro-6-(tetrahydrofuran-3-ylamino)-4-(3,6,6-trimethyl-4,5,6,7-tetrahydro-1H-indazol-1-yl)benzamide) |
| 92 | 2-((1S,2S)-2-aminocyclohexylamino)-4-(3-ethyl-6,6-dimethyl-4,5,6,7-tetrahydro-1H-indazol-1-yl)-6-fluorobenzamide) |
| 93 | 4-(3-(cyclopropylmethyl)-6,6-dimethyl-4,5,6,7-tetrahydro-1H-indazol-1-yl)-2-fluoro-6((1S,2S)-2-hydroxycyclopentylamino)benzamide |
| 94 | 4-(3-(cyclopropylmethyl)-6,6-dimethyl-4,5,6,7-tetrahydro-1H-indazol-1-yl)-2-fluoro-6-(1S,2S)-2-hydroxycyclohexylamino)benzamide |

TABLE 1A-continued

| Compound (EX-) number | Compound Name |
|---|---|
| 95 | 4-(3-(cyclopropylmethyl)-6,6-dimethyl-4,5,6,7-tetrahydro-1H-indazol-1-yl)-2-fluoro-6-(trans-4-hydroxycyclohexylamino)benzamide |
| 96 | 4-(3-(cyclopropylmethyl)-6,6-dimethyl-4,5,6,7-tetrahydro-1H-indazol-1-yl)-5-fluoro-2-(trans-4-hydroxycyclohexylamino)benzamide |
| 97 | 4-(3-ethyl-6,6-dimethyl-4,5,6,7-tetrahydro-1H-indazol-1-yl)-5-fluoro-2-(trans-4-hydroxycyclohexylamino)benzamide) |
| 98 | 2-fluoro-6-((1S,2S)-2-hydroxycyclopentylamino)-4-(3,6,6-trimethyl-4,5,6,7-tetrahydro-1H-indazol-1-yl)benzamide |
| 99 | 2-(cyclopropylmethylamino)-4-(3-ethyl-6,6-dimethyl-4,5,6,7-tetrahydro-1H-indazol-1-yl)-6-fluorobenzamide |
| 100 | 4-(6,6-dimethyl-3-(trifluoromethyl)-4,5,6,7-tetrahydro-1H-indazol-1-yl)-2-fluoro-6-(((1S,2S)-2-hydroxycyclohexyl)amino)benzamide |
| 101 | 4-(6,6-dimethyl-3-(trifluoromethyl)-6,7-dihydro-1H-indazol-1-yl)-2-fluoro-6-(((1S,2S)-2-hydroxycyclohexyl)amino)benzamide |
| 102 | (S)-4-(3-ethyl-6,6-dimethyl-4,5,6,7-tetrahydro-1H-indazol-1-yl)-2-fluoro-6-(tetrahydrofuran-3-ylamino)benzamide |
| 103 | 4-(3-ethyl-6,6-dimethyl-4,5,6,7-tetrahydro-1H-indazol-1-yl)-2-fluoro-6-((1S,2S)-2-hydroxycyclohexylamino)benzamide |
| 104 | (R)-4-(3-ethyl-6,6-dimethyl-4,5,6,7-tetrahydro-1H-indazol-1-yl)-2-fluoro-6-(tetrahydrofuran-3-ylamino)benzamide |
| 105 | (S)-4-(3-(cyclopropylmethyl)-6,6-dimethyl-4,5,6,7-tetrahydro-1H-indazol-1-yl)-2-fluoro-6-(tetrahydrofuran-3-ylamino)benzamide |
| 106 | (R)-4-(3-(cyclopropylmethyl)-6,6-dimethyl-4,5,6,7-tetrahydro-1H-indazol-1-yl)-2-fluoro-6-(tetrahydrofuran-3-ylamino)benzamide |
| 107 | 4-(3-ethyl-6,6-dimethyl-4,5,6,7-tetrahydro-1H-indazol-1-yl)-3-fluoro-2-(tetrahydro-2H-pyran-4-ylamino)benzamide |
| 108 | 4-(3-(cyclopropylmethyl)-6,6-dimethyl-4,5,6,7-tetrahydro-1H-indazol-1-yl)-3-fluoro-2-(tetrahydro-2H-pyran-4-ylamino)benzamide |
| 109 | 4-(3-ethyl-6,6-dimethyl-4,5,6,7-tetrahydro-1H-indazol-1-yl)-3-fluoro-2-(2-hydroxyethylamino)benzamide |
| 110 | 4-(3-(cyclopropylmethyl)-6,6-dimethyl-4,5,6,7-tetrahydro-1H-indazol-1-yl)-3-fluoro-2-(trans-4-hydroxycyclohexylamino)benzamide |
| 111 | 4-(3-(cyclopropylmethyl)-6,6-dimethyl-4,5,6,7-tetrahydro-1H-indazol-1-yl)-3-fluoro-2-(1S,2S)-2-hydroxycyclohexylamino)benzamide |
| 112 | 4-(3-ethyl-6,6-dimethyl-4,5,6,7-tetrahydro-1H-indazol-1-yl)-2-fluoro-6-((1S,2S)-2-hydroxycyclopentylamino)benzamide |
| 113 | 4-(3-(cyclopropylmethyl)-6,6-dimethyl-4,5,6,7-tetrahydro-1H-indazol-1-yl)-5-fluoro-2-(tetrahydro-2H-pyran-4-ylamino)benzamide |
| 114 | 4-(3-ethyl-6,6-dimethyl-4,5,6,7-tetrahydro-1H-indazol-1-yl)-5-fluoro-2-(tetrahydro-2H-pyran-4-ylamino)benzamide |
| 115 | (R)-4-(3-ethyl-6,6-dimethyl-4,5,6,7-tetrahydro-1H-indazol-1-yl)-5-fluoro-2-(tetrahydrofuran-3-ylamino)benzamide |
| 116 | 4-(3-(cyclopropylmethyl)-6,6-dimethyl-4,5,6,7-tetrahydro-1H-indazol-1-yl)-5-fluoro-2-((1S,2S)-2-hydroxycyclohexylamino)benzamide |
| 117 | 4-(3-(cyclopropylmethyl)-6,6-dimethyl-4,5,6,7-tetrahydro-1H-indazol-1-yl)-5-fluoro-2-((1S,2S)-2-hydroxycyclopentylamino)benzamide |
| 118 | 4-(3-ethyl-6,6-dimethyl-4,5,6,7-tetrahydro-1H-indazol-1-yl)-5-fluoro-2-((1S,2S)-2-hydroxycyclopentylamino)benzamide |
| 119 | 4-(3-ethyl-6,6-dimethyl-4,5,6,7-tetrahydro-1H-indazol-1-yl)-3,5-difluoro-2-(tetrahydro-2H-pyran-4-ylamino)benzamide |
| 120 | 4-(3-ethyl-6,6-dimethyl-4,5,6,7-tetrahydro-1H-indazol-1-yl)-3,5-difluoro-2-((R)-tetrahydrofuran-3-ylamino)benzamide |
| 121 | 4-(3-(cyclopropylmethyl)-6,6-dimethyl-4,5,6,7-tetrahydro-1H-indazol-1-yl)-3,5-difluoro-2-((R)-tetrahydrofuran-3-ylamino)benzamide |
| 122 | 4-(3-(cyclopropylmethyl)-6,6-dimethyl-4,5,6,7-tetrahydro-1H-indazol-1-yl)-3,5-difluoro-2-(tetrahydro-2H-pyran-4-ylamino)benzamide |
| 123 | 4-(3-ethyl-6,6-dimethyl-4,5,6,7-tetrahydro-1H-indazol-1-yl)-2-fluoro-6-((1S,2S)-2-(neopentylamino)cyclohexylamino)benzamide |
| 124 | 4-(3-ethyl-6,6-dimethyl-4,5,6,7-tetrahydro-1H-indazol-1-yl)-2-fluoro-6-(trans-4-(neopentylamino)cyclohexylamino)benzamide |
| 125 | 4-(3-ethyl-6,6-dimethyl-4,5,6,7-tetrahydro-1H-indazol-1-yl)-2-fluoro-6-(2-oxotetrahydrofuran-3-ylamino)benzamide |
| 126 | 4-(3-(cyclopropylmethyl)-6,6-dimethyl-4,5,6,7-tetrahydro-1H-indazol-1-yl)-3,5-difluoro-2-(trans-4-hydroxycyclohexylamino)benzamide |
| 127 | methyl 2-(2-carbamoyl-5-(3-ethyl-6,6-dimethyl-4,5,6,7-tetrahydro-1H-indazol-1-yl)-3-fluorophenylamino)-4-hydroxybutanoate |
| 128 | 2-(cyclopent-3-enylamino)-4-(3-ethyl-6,6-dimethyl-4,5,6,7-tetrahydro-1H-indazol-1-yl)-6-fluorobenzamide) |
| 129 | 2-(1-acetylpiperidin-4-ylamino)-4-(3-ethyl-6,6-dimethyl-4,5,6,7-tetrahydro-1H-indazol-1-yl)-6-fluorobenzamide6H), 1.17 (t, 3H), 1.00 (s, 6H) |
| 130 | 4-(3-(cyclopropylmethyl)-6,6-dimethyl-4,5,6,7-tetrahydro-1H-indazol-1-yl)-2-fluoro-6-(2-oxotetrahydrofuran-3-ylamino)benzamide |
| 131 | 2-fluoro-6-(4-hydroxycyclohexylamino)-4-(3,6,6-trimethyl-4,5,6,7-tetrahydro-1H-indazol-1-yl)benzamide |
| 132 | 2-fluoro-6-(2-oxotetrahydrofuran-3-ylamino)-4-(3,6,6-trimethyl-4,5,6,7-tetrahydro-1H-indazol-1-yl)benzamide |
| 133 | 4-(3-ethyl-6,6-dimethyl-4,5,6,7-tetrahydro-1H-indazol-1-yl)-2-fluoro-6-(2-oxoazepan-3-ylamino)benzamide |
| 134 | 2-(2,2-dimethoxyethylamino)-4-(3-ethyl-6,6-dimethyl-4,5,6,7-tetrahydro-1H-indazol-1-yl)-6-fluorobenzamide) |
| 135 | 4-(3-ethyl-6,6-dimethyl-4,5,6,7-tetrahydro-1H-indazol-1-yl)-2-fluoro-6-(trans-4-hydroxycyclohexylamino)benzamide |
| 136 | 4-(3-ethyl-6,6-dimethyl-4,5,6,7-tetrahydro-1H-indazol-1-yl)-2-fluoro-6-(trans-4-methoxycyclohexylamino)benzamide |
| 137 | 4-(3-ethyl-6,6-dimethyl-4,5,6,7-tetrahydro-1H-indazol-1-yl)-2-fluoro-6-((1S,2R)-2-hydroxycyclohexylamino)benzamide |
| 138 | 4-(3-ethyl-6,6-dimethyl-4,5,6,7-tetrahydro-1H-indazol-1-yl)-2-fluoro-6-((1S,2R)-2-hydroxycyclopentylamino)benzamide |
| 139 | 2-(cyclopentylamino)-4-(3-ethyl-6,6-dimethyl-4,5,6,7-tetrahydro-1H-indazol-1-yl)-6-fluorobenzamide |
| 140 | (1S,2S)-2-(2-carbamoyl-5-(3-ethyl-6,6-dimethyl-4,5,6,7-tetrahydro-1H-indazol-1-yl)-3-fluorophenylamino)cyclohexyl 2-aminoacetate |
| 141 | (1S,2S)-2-(2-carbamoyl-5-(3-ethyl-6,6-dimethyl-4,5,6,7-tetrahydro-1H-indazol-1-yl)-3-fluorophenylamino)cyclopentyl 2-aminoacetate |
| 142 | (1S,2S)-2-(2-carbamoyl-3-fluoro-5-(3,6,6-trimethyl-4,5,6,7-tetrahydro-1H-indazol-1-yl)phenylamino)cyclopentyl 2-aminoacetate |
| 143 | (1S,2S)-2-(2-carbamoyl-3-fluoro-5-(3,6,6-trimethyl-4,5,6,7-tetrahydro-1H-indazol-1-yl)phenylamino)cyclohexyl 2-aminoacetate |
| 144 | (trans)-4-(2-carbamoyl-5-(3-ethyl-6,6-dimethyl-4,5,6,7-tetrahydro-1H-indazol-1-yl)-3-fluorophenylamino)cyclohexyl 2-aminoacetate |
| 145 | (trans)-4-(2-carbamoyl-3-fluoro-5-(3,6,6-trimethyl-4,5,6,7-tetrahydro-1H-indazol-1-yl)phenylamino)cyclohexyl 2-aminoacetate |
| 146 | (S)-2-fluoro-6-(6-oxotetrahydro-2H-pyran-3-ylamino)-4-(3,6,6-trimethyl-4,5,6,7-tetrahydro-1H-indazol-1-yl)benzamide |
| 147 | (R)-2-fluoro-6-(6-oxotetrahydro-2H-pyran-3-ylamino)-4-(3,6,6-trimethyl-4,5,6,7-tetrahydro-1H-indazol-1-yl)benzamide |

TABLE 1A-continued

| Compound (EX-) number | Compound Name |
|---|---|
| 148 | 2-fluoro-6-((cis)-4-hydroxycyclohexylamino)-4-(3,6,6-trimethyl-4,5,6,7-tetrahydro-1H-indazol-1-yl)benzamide |
| 149 | 2-fluoro-6-(oxetan-3-ylamino)-4-(3,6,6-trimethyl-4,5,6,7-tetrahydro-1H-indazol-1-yl)benzamide |
| 150 | 2-(cyclopentylamino)-6-fluoro-4-(3,6,6-trimethyl-4,5,6,7-tetrahydro-1H-indazol-1-yl)benzamide |
| 151 | 2-(cycloheptylamino)-6-fluoro-4-(3,6,6-trimethyl-4,5,6,7-tetrahydro-1H- indazol-1-yl)benzamide |
| 152 | (trans)-4-(2-carbamoyl-5-(6,6-dimethyl-3-(trifluoromethyl)-4,5,6,7-tetrahydro-1H-indazol-1-yl)-3-fluorophenylamino)cyclohexyl 2-aminoacetate |
| 153 | 4-(6,6-dimethyl-3-(trifluoromethyl)-4,5,6,7-tetrahydro-1H-indazol-1-yl)-2-fluoro-6-((1S,2S)-2-hydroxycyclopentylamino)benzamide |
| 154 | (1S,2S)-2-(2-carbamoyl-5-(6,6-dimethyl-3-(trifluoromethyl)-4,5,6,7-tetrahydro-1H-indazol-1-yl)-3-fluorophenylamino)cyclopentyl 2-aminoacetate |
| 155 | 4-(6,6-dimethyl-3-(trifluoromethyl)-4,5,6,7-tetrahydro-1H-indazol-1-yl)-2-fluoro-6-(tetrahydro-2H-pyran-4-ylamino)benzamide |
| 156 | 4-(6,6-dimethyl-3-(trifluoromethyl)-4,5,6,7-tetrahydro-1H-indazol-1-yl)-2-fluoro-6-((1S,2S)-2-hydroxycyclohexylamino)benzamide |
| 157 | (1S,2S)-2-(2-carbamoyl-5-(6,6-dimethyl-3-(trifluoromethyl)-4,5,6,7-tetrahydro-1H-indazol-1-yl)-3-fluorophenylamino)cyclohexyl 2-aminoacetate |
| 158 | (S)-4-(6,6-dimethyl-3-(trifluoromethyl)-4,5,6,7-tetrahydro-1H-indazol-1-yl)-2-fluoro-6-(tetrahydrofuran-3-ylamino)benzamide |
| 159 | 2-fluoro-6-((1S,2R)-2-hydroxycyclopentylamino)-4-(3,6,6-trimethyl-4,5,6,7-tetrahydro-1H-indazol-1-yl)benzamide |
| 160 | 2-(4,4-difluorocyclohexylamino)-6-fluoro-4-(3,6,6-trimethyl-4,5,6,7-tetrahydro-1H-indazol-1-yl)benzamide |
| 161 | 2-(cyclopentylamino)-4-(6,6-dimethyl-3-(trifluoromethyl)-4,5,6,7-tetrahydro-1H-indazol-1-yl)-6-fluorobenzamide |
| 162 | 2-(cyclohexylamino)-6-fluoro-4-(3,6,6-trimethyl-4,5,6,7-tetrahydro-1H-indazol-1-yl)benzamide |
| 163 | 2-fluoro-6-((1R,2R)-2-hydroxycyclopentylamino)-4-(3,6,6-trimethyl-4,5,6,7-tetrahydro-1H-indazol-1-yl)benzamide |
| 164 | (1R,2R)-2-(2-carbamoyl-3-fluoro-5-(3,6,6-trimethyl-4,5,6,7-tetrahydro-1H-indazol-1-yl)phenylamino)cyclopentyl 2-aminoacetate |
| 165 | (S)-(trans-4-(2-carbamoyl-5-(6,6-dimethyl-3-(trifluoromethyl)-4,5,6,7-tetrahydro-1H-indazol-1-yl)phenylamino)cyclohexyl) 2-amino-3-hydroxypropanoate |
| 166 | trans-4-(2-carbamoyl-5-(6,6-dimethyl-3-(trifluoromethyl)-4,5,6,7-tetrahydro-1H-indazol-1-yl)phenylamino)cyclohexyl 2-(dimethylamino)acetate |
| 167 | 4-(6,6-dimethyl-3-(trifluoromethyl)-4,5,6,7-tetrahydro-1H-indazol-1-yl)-2-(pyrimidin-2-ylamino)benzamide |
| 168 | 4-(6,6-dimethyl-3-(trifluoromethyl)-4,5,6,7-tetrahydro-1H-indazol-1-yl)-2-(pyrimidin-4-ylamino)benzamide |
| 169 | 4-(6,6-dimethyl-3-(trifluoromethyl)-4,5,6,7-tetrahydro-1H-indazol-1-yl)-2-(pyrimidin-5-ylamino)benzamide |
| 170 | 4-(3-(difluoromethyl)-6,6-dimethyl-4,5,6,7-tetrahydro-1H-indazol-1-yl)-2-(1-(prop-2-ynyl)piperidin-4-ylamino)benzamide |
| 171 | 2-(1-cyclopropylpiperidin-4-ylamino)-4-(3-(difluoromethyl)-6,6-dimethyl-4,5,6,7-tetrahydro-1H-indazol-1-yl)benzamide |
| 172 | 4-(3-(difluoromethyl)-6,6-dimethyl-4,5,6,7-tetrahydro-1H-indazol-1-yl)-2-(1-(2-methoxyethyl)piperidin-4-ylamino)benzamide |
| 173 | 4-(6,6-dimethyl-3-(trifluoromethyl)-4,5,6,7-tetrahydro-1H-indazol-1-yl)-2-(2-(2-hydroxyethoxy)pyridin-4-ylamino)benzamide |
| 174 | 2-(1-(2-(methylamino)ethyl)-1H-pyrazol-4-ylamino)-4-(3,6,6-trimethyl-4,5,6,7-tetrahydro-1H-indazol-1-yl)benzamide |
| 175 | 4-(6,6-dimethyl-3-(trifluoromethyl)-4,5,6,7-tetrahydro-1H-indazol-1-yl)-2-(trans-4-(prop-2-ynylamino)cyclohexylamino)benzamide |
| 176 | 4-(6,6-dimethyl-3-(trifluoromethyl)-4,5,6,7-tetrahydro-1H-indazol-1-yl)-2-(1-(prop-2-ynyl)piperidin-4-ylamino)benzamide |
| 177 | 2-(azetidin-3-ylamino)-4-(6,6-dimethyl-3-(trifluoromethyl)-4,5,6,7-tetrahydro-1H-indazol-1-yl)benzamide |
| 178 | 2-((1S,2S)-2-aminocyclohexylamino)-4-(6,6-dimethyl-3-(trifluoromethyl)-4,5,6,7-tetrahydro-1H-indazol-1-yl)benzamide |
| 179 | 4-(6,6-dimethyl-3-(trifluoromethyl)-4,5,6,7-tetrahydro-1H-indazol-1-yl)-2-(2-(diprop-2-ynylamino)ethylamino)benzamide |
| 180 | 4-(6,6-dimethyl-3-(trifluoromethyl)-4,5,6,7-tetrahydro-1H-indazol-1-yl)-2-(2-(prop-2-ynylamino)ethylamino)benzamide |
| 181 | 4-(6,6-dimethyl-3-(trifluoromethyl)-4,5,6,7-tetrahydro-1H-indazol-1-yl)-2-((1S,2S)-2-(prop-2-ynylamino)cyclohexylamino)benzamide |
| 182 | 2-(1-allylpiperidin-4-ylamino)-4-(6,6-dimethyl-3-(trifluoromethyl)-4,5,6,7-tetrahydro-1H-indazol-1-yl)benzamide |
| 183 | 2-((1R,2R)-2-aminocyclohexylamino)-4-(6,6-dimethyl-3-(trifluoromethyl)-4,5,6,7-tetrahydro-1H-indazol-1-yl)benzamide |
| 184 | 2-((1R,2S)-2-aminocyclohexylamino)-4-(6,6-dimethyl-3-(trifluoromethyl)-4,5,6,7-tetrahydro-1H-indazol-1-yl)benzamide |
| 185 | (S)-4-(6,6-dimethyl-3-(trifluoromethyl)-4,5,6,7-tetrahydro-1H-indazol-1-yl)-2-(1-(prop-2-ynyl)piperidin-3-ylamino)benzamide |
| 186 | (S)-2-(1-allylpiperidin-3-ylamino)-4-(6,6-dimethyl-3-(trifluoromethyl)-4,5,6,7-tetrahydro-1H-indazol-1-yl)benzamide |
| 187 | (R)-4-(6,6-dimethyl-3-(trifluoromethyl)-4,5,6,7-tetrahydro-1H-indazol-1-yl)-2-(piperidin-3-ylamino)benzamide |
| 188 | 4-(6,6-dimethyl-3-(trifluoromethyl)-4,5,6,7-tetrahydro-1H-indazol-1-yl)-2-(2-(pyrimidin-2-ylthio)ethylamino)benzamide |
| 189 | (R)-4-(6,6-dimethyl-3-(trifluoromethyl)-4,5,6,7-tetrahydro-1H-indazol-1-yl)-2-(1-(prop-2-ynyl)piperidin-3-ylamino)benzamide |
| 190 | (S)-2-(1-(cyclopropylmethyl)piperidin-3-ylamino)-4-(6,6-dimethyl-3-(trifluoromethyl)-4,5,6,7-tetrahydro-1H-indazol-1-yl)benzamide) |
| 191 | 2-(1-(cyclopropylmethyl)piperidin-4-ylamino)-4-(6,6-dimethyl-3-(trifluoromethyl)-4,5,6,7-tetrahydro-1H-indazol-1-yl)benzamide |
| 192 | 2-(3-aminocyclohexylamino)-4-(6,6-dimethyl-3-(trifluoromethyl)-4,5,6,7-tetrahydro-1H-indazol-1-yl)benzamide |
| 193 | 2-(1-(2-(tert-butylamino)ethyl)-1H-pyrazol-4-ylamino)-4-(3,6,6-trimethyl-4,5,6,7-tetrahydro-1H-indazol-1-yl)benzamide |
| 194 | 4-(6,6-dimethyl-3-(trifluoromethyl)-4,5,6,7-tetrahydro-1H-indazol-1-yl)-2-(pyridazin-4-ylamino)benzamide |
| 195 | (R)-2-(1-(cyclopropylmethyl)piperidin-3-ylamino)-4-(6,6-dimethyl-3-(trifluoromethyl)-4,5,6,7-tetrahydro-1H-indazol-1-yl)benzamide |
| 196 | 2-((1S,2S)-2-(cyclopropylmethylamino)cyclohexylamino)-4-(6,6-dimethyl-3-(trifluoromethyl)-4,5,6,7-tetrahydro-1H-indazol-1-yl)benzamide |
| 197 | 2-(2-(1H-imidazol-2-ylthio)ethylamino)-4-(6,6-dimethyl-3-(trifluoromethyl)-4,5,6,7-tetrahydro-1H-indazol-1-yl)benzamide |
| 198 | 4-(6,6-dimethyl-3-(trifluoromethyl)-4,5,6,7-tetrahydro-1H-indazol-1-yl)-2-((1R,2R)-2-(prop-2-ynylamino)cyclohexylamino)benzamide |
| 199 | 4-(6,6-dimethyl-3-(trifluoromethyl)-4,5,6,7-tetrahydro-1H-indazol-1-yl)-2-((1R,2R)-2-(diprop-2-ynylamino)cyclohexylamino)benzamide |
| 200 | 2-((1R,2R)-2-(cyclopropylmethylamino)cyclohexylamino)-4-(6,6-dimethyl-3-(trifluoromethyl)-4,5,6,7-tetrahydro-1H-indazol-1-yl)benzamide |
| 201 | 2-((1R,2R)-2-(bis(cyclopropylmethyl)amino)cyclohexylamino)-4-(6,6-dimethyl-3-(trifluoromethyl)-4,5,6,7-tetrahydro-1H-indazol-1-yl)benzamide |
| 202 | 2-((1S,2S)-2-(diethylamino)cyclohexylamino)-4-(6,6-dimethyl-3-(trifluoromethyl)-4,5,6,7-tetrahydro-1H-indazol-1-yl)benzamide |

TABLE 1A-continued

| Compound (EX-) number | Compound Name |
|---|---|
| 203 | 2-((1S,2S)-2-(cyclopropylamino)cyclohexylamino)-4-(6,6-dimethyl-3-(trifluoromethyl)-4,5,6,7-tetrahydro-1H-indazol-1-yl)benzamide |
| 204 | 4-(6,6-dimethyl-3-(trifluoromethyl)-4,5,6,7-tetrahydro-1H-indazol-1-yl)-2-(trans-4-(neopentylamino)cyclohexylamino)benzamide |
| 205 | 4-(6,6-dimethyl-3-(trifluoromethyl)-4,5,6,7-tetrahydro-1H-indazol-1-yl)-2-((1S,2S)-2-(neopentylamino)cyclohexylamino)benzamide |
| 206 | (1S,2S)-2-(2-carbamoyl-5-(3-ethyl-6,6-dimethyl-4,5,6,7-tetrahydro-1H-indazol-1-yl)phenylamino)cyclohexyl 2-aminoacetate |
| 207 | 4-(3-(difluoromethyl)-6,6-dimethyl-4,5,6,7-tetrahydro-1H-indazol-1-yl)-2-(2,2,6,6-tetramethylpiperidin-4-ylamino)benzamide |
| 208 | (1S,2S)-2-(2-carbamoyl-5-(6,6-dimethyl-3-(trifluoromethyl)-4,5,6,7-tetrahydro-1H-indazol-1-yl)phenylamino)cyclopentyl 2-aminoacetate |
| 209 | (1S,2S)-2-(2-carbamoyl-5-(6,6-dimethyl-3-(trifluoromethyl)-4,5,6,7-tetrahydro-1H-indazol-1-yl)phenylamino)cyclohexyl 2-aminoacetate |
| 210 | (1S,2S)-2-(2-carbamoyl-5-(6,6-dimethyl-3-(trifluoromethyl)-4,5,6,7-tetrahydro-1H-indazol-1-yl)phenylamino)cyclopentyl 1-aminocyclopropanecarboxylate methanesulfonate |
| 211 | trans-4-(2-carbamoyl-5-(6,6-dimethyl-3-(trifluoromethyl)-4,5,6,7-tetrahydro-1H-indazol-1-yl)phenylamino)cyclohexyl 2-(2-aminoacetamido)acetate 2,2,2-trifluoroacetate |
| 212 | 4-(6,6-dimethyl-3-(trifluoromethyl)-4,5,6,7-tetrahydro-1H-indazol-1-yl)-2-(4-(2-(methoxyimino)ethoxy)cyclohexylamino)benzamide |
| 213 | 4-(6,6-dimethyl-3-(trifluoromethyl)-4,5,6,7-tetrahydro-1H-indazol-1-yl)-2-(4-(2-(phenoxyimino)ethoxy)cyclohexylamino)benzamide |
| 214 | 2-(trans-4-(2-hydroxyethoxy)cyclohexylamino)-4-(3,6,6-trimethyl-4,5,6,7-tetrahydro-1H-indazol-1-yl)benzamide |
| 215 | (R)-2-(tetrahydrofuran-3-ylamino)-4-(3,6,6-trimethyl-4,5,6,7-tetrahydro-1H-indazol-1-yl)benzamide |
| 216 | 4-(6,6-dimethyl-3-(trifluoromethyl)-4,5,6,7-tetrahydro-1H-indazol-1-yl)-2-(4-(2-(hydroxyamino)-2-oxoethoxy)cyclohexylamino)benzamide |
| 217 | 2-(trans-4-(2-(2-hydroxyethoxy)ethoxy)cyclohexylamino)-4-(3,6,6-trimethyl-4,5,6,7-tetrahydro-1H-indazol-1-yl)benzamide |
| 218 | 2-(cyclobutylamino)-4-(6,6-dimethyl-3-(trifluoromethyl)-4,5,6,7-tetrahydro-1H-indazol-1-yl)benzamide |
| 219 | 2-(4-(2-hydroxyethoxy)cyclohexylamino)-4-(3,6,6-trimethyl-4,5,6,7-tetrahydro-1H-indazol-1-yl)benzamide |
| 220 | 4-(6,6-dimethyl-3-(trifluoromethyl)-4,5,6,7-tetrahydro-1H-indazol-1-yl)-2-(2-hydroxyethylamino)benzamide |
| 221 | 2-(cyclobutylamino)-4-(3-ethyl-6,6-dimethyl-4,5,6,7-tetrahydro-1H-indazol-1-yl)benzamide |
| 222 | 2-(trans-4-hydroxycyclohexylamino)-4-(3-(3-methoxyphenyl)-6,6-dimethyl-4,5,6,7-tetrahydro-1H-indazol-1-yl)benzamide |
| 223 | 4-(3-benzyl-6,6-dimethyl-4,5,6,7-tetrahydro-1H-indazol-1-yl)-2-(trans-4-hydroxycyclohexylamino)benzamide |
| 224 | 4-(6,6-dimethyl-3-(1H-pyrazol-4-yl)-4,5,6,7-tetrahydro-1H-indazol-1-yl)-2-(trans-4-hydroxycyclohexylamino)benzamide |
| 225 | 4-(6,6-dimethyl-3-(pyridin-3-ylmethyl)-4,5,6,7-tetrahydro-1H-indazol-1-yl)-2-(trans-4-hydroxycyclohexylamino)benzamide |
| 226 | 4-(6,6-dimethyl-3-(pyridin-2-ylmethyl)-4,5,6,7-tetrahydro-1H-indazol-1-yl)-2-(trans-4-hydroxycyclohexylamino)benzamide |
| 227 | 4-(3-(cyclopropylmethyl)-6,6-dimethyl-4,5,6,7-tetrahydro-1H-indazol-1-yl)-2-(tetrahydro-2H-pyran-4-ylamino)benzamide |
| 228 | 4-(6,6-dimethyl-3-(trifluoromethyl)-4,5,6,7-tetrahydro-1H-indazol-1-yl)-2- (2-hydroxycyclohexylamino)benzamide |
| 229 | 4-(6,6-dimethyl-3-(pyridin-2-ylmethyl)-4,5,6,7-tetrahydro-1H-indazol-1-yl)-2-(2-hydroxyethylamino)benzamide |
| 230 | 4-(3-benzyl-6,6-dimethyl-4,5,6,7-tetrahydro-1H-indazol-1-yl)-2-(2-hydroxyethylamino)benzamide |
| 231 | 4-(3-(cyclopropylmethyl)-6,6-dimethyl-4,5,6,7-tetrahydro-1H-indazol-1-yl)-2-(2-hydroxyethylamino)benzamide |
| 232 | 4-(3-benzyl-6,6-dimethyl-4,5,6,7-tetrahydro-1H-indazol-1-yl)-2-(tetrahydro-2H-pyran-4-ylamino)benzamide |
| 233 | (R)-4-(6,6-dimethyl-3-(trifluoromethyl)-4,5,6,7-tetrahydro-1H-indazol-1- yl)-2-(1-hydroxypropan-2-ylamino)benzamide |
| 234 | (S)-4-(6,6-dimethyl-3-(trifluoromethyl)-4,5,6,7-tetrahydro-1H-indazol-1-yl)-2-(1-hydroxypropan-2-ylamino)benzamide |
| 235 | (S)-4-(6,6-dimethyl-3-(trifluoromethyl)-4,5,6,7-tetrahydro-1H-indazol-1-yl)-2-(2-hydroxypropylamino)benzamide |
| 236 | 4-(6,6-dimethyl-3-(pyridin-3-ylmethyl)-4,5,6,7-tetrahydro-1H-indazol-1-yl)-2-(tetrahydro-2H-pyran-4-ylamino)benzamide |
| 237 | 4-(6,6-dimethyl-3-(pyridin-4-ylmethyl)-4,5,6,7-tetrahydro-1H-indazol-1-yl)-2-(2-hydroxyethylamino)benzamide |
| 238 | 4-(6,6-dimethyl-3-(pyridin-3-ylmethyl)-4,5,6,7-tetrahydro-1H-indazol-1-yl)-2-(2-hydroxyethylamino)benzamide |
| 239 | 4-(6,6-dimethyl-3-(thiophen-3-ylmethyl)-4,5,6,7-tetrahydro-1H-indazol-1-yl)-2-(2-hydroxyethylamino)benzamide |
| 240 | 4-(6,6-dimethyl-3-(pyridin-4-ylmethyl)-4,5,6,7-tetrahydro-1H-indazol-1-yl)-2-(tetrahydro-2H-pyran-4-ylamino)benzamide |
| 241 | 4-(6,6-dimethyl-3-(pyridin-4-ylmethyl)-4,5,6,7-tetrahydro-1H-indazol-1-yl)-2-(trans-4-hydroxycyclohexylamino)benzamide |
| 242 | 4-(6,6-dimethyl-3-(trifluoromethyl)-4,5,6,7-tetrahydro-1H-indazol-1-yl)-2-((1S,2S)-2-hydroxycyclohexylamino)benzamide |
| 243 | (R)-4-(3-(cyclopropylmethyl)-6,6-dimethyl-4,5,6,7-tetrahydro-1H-indazol-1-yl)-2-(tetrahydrofuran-3-ylamino)benzamide |
| 244 | 4-(6,6-dimethyl-3-(trifluoromethyl)-4,5,6,7-tetrahydro-1H-indazol-1-yl)-2-((1R,2R)-2-hydroxycyclohexylamino)benzamide |
| 245 | 4-(6,6-dimethyl-3-(trifluoromethyl)-4,5,6,7-tetrahydro-1H-indazol-1-yl)-2-((1R,2R)-2-hydroxycyclopentylamino)benzamide |
| 246 | 4-(6,6-dimethyl-3-(trifluoromethyl)-4,5,6,7-tetrahydro-1H-indazol-1-yl)-2-((1S,2S)-2-hydroxycyclopentylamino)benzamide |
| 247 | 4-(3-ethyl-6,6-dimethyl-4,5,6,7-tetrahydro-1H-indazol-1-yl)-2-((1S,2S)-2-hydroxycyclohexylamino)benzamide |
| 248 | 4-(3-(cyclopropylmethyl)-6,6-dimethyl-4,5,6,7-tetrahydro-1H-indazol-1-yl)-2-((1S,2S)-2-hydroxycyclopentylamino)benzamide |
| 249 | 4-(3-(cyclopropylmethyl)-6,6-dimethyl-4,5,6,7-tetrahydro-1H-indazol-1-yl)-2-((1S,2S)-2-hydroxycyclohexylamino)benzamide |
| 250 | 4-(3-ethyl-6,6-dimethyl-4,5,6,7-tetrahydro-1H-indazol-1-yl)-2-((1S,2S)-2-hydroxycyclopentylamino)benzamide |
| 251 | (S)-2-(tetrahydrofuran-3-ylamino)-4-(3,6,6-trimethyl-4,5,6,7-tetrahydro-1H-indazol-1-yl)benzamide |
| 252 | 2-((1S,2S)-2-hydroxycyclopentylamino)-4-(3,6,6-trimethyl-4,5,6,7-tetrahydro-1H-indazol-1-yl)benzamide) |
| 253 | 2-((1S,2S)-2-hydroxycyclohexylamino)-4-(3,6,6-trimethyl-4,5,6,7-tetrahydro-1H-indazol-1-yl)benzamide |
| 254 | 2-(oxetan-3-ylamino)-4-(3,6,6-trimethyl-4,5,6,7-tetrahydro-1H-indazol-1-yl)benzamide |
| 255 | (S)-4-(6,6-dimethyl-3-(trifluoromethyl)-4,5,6,7-tetrahydro-1H-indazol-1-yl)-2-(tetrahydrofuran-3-ylamino)benzamide |
| 256 | 4-(6-ethyl-3,6-dimethyl-4,5,6,7-tetrahydro-1H-indazol-1-yl)-2-((trans)-4-hydroxycyclohexylamino)benzamide |
| 257 | 2-(cyclopentylamino)-4-(3,6,6-trimethyl-4,5,6,7-tetrahydro-1H-indazol-1-yl)benzamide |
| 258 | 2-(cycloheptylamino)-4-(3,6,6-trimethyl-4,5,6,7-tetrahydro-1H-indazol-1-yl)benzamide |
| 259 | 4-(3-ethyl-6,6-dimethyl-4,5,6,7-tetrahydro-1H-indazol-1-yl)-2-methoxy-6-(tetrahydro-2H-pyran-4-ylamino)benzamide |
| 260 | 4-(6,6-dimethyl-3-(2,2,2-trifluoroethyl)-4,5,6,7-tetrahydro-1H-indazol-1-yl)-2-(trans-4-hydroxycyclohexylamino)benzamide |
| 261 | 4-(6,6-dimethyl-3-(trifluoromethyl)-4,5,6,7-tetrahydro-1H-indazol-1-yl)-2-((1S,2R)-2-hydroxycyclopentylamino)benzamide |
| 262 | 2-(cyclopentylamino)-4-(6,6-dimethyl-3-(trifluoromethyl)-4,5,6,7-tetrahydro-1H-indazol-1-yl)benzamide |

TABLE 1A-continued

| Compound (EX-) number | Compound Name |
|---|---|
| 263 | 2-(cyclohexylamino)-4-(3,6,6-trimethyl-4,5,6,7-tetrahydro-1H-indazol-1-yl)benzamide |
| 264 | 4-(3,6,6-trimethyl-4,5,6,7-tetrahydro-1H-indazol-1-yl)-1H-benzo[d]imidazole-7-carboxamide |
| 265 | 4-(3-ethyl-6,6-dimethyl-4,5,6,7-tetrahydro-1H-indazol-1-yl)-1H-benzo[d]imidazole-7-carboxamide |
| 266 | 4-(3-ethyl-6,6-dimethyl-4,5,6,7-tetrahydro-1H-indazol-1-yl)-2-methyl-1H-benzo[d]imidazole-7-carboxamide |
| 267 | 2-phenyl-4-(3,6,6-trimethyl-4,5,6,7-tetrahydro-1H-indazol-1-yl)-1H-benzo[d]imidazole-7-carboxamide) |
| 268 | 4-(3-ethyl-6,6-dimethyl-4,5,6,7-tetrahydro-1H-indazol-1-yl)-2-phenyl-1H-benzo[d]imidazole-7-carboxamide |

Example 19

Cell Proliferation Assays

A panel of cancer cell lines may be obtained from the DCTP Tumor Repository, National Cancer Institute (Frederick, Md.) or ATCC (Rockville, Md.). Cell cultures are maintained in Hyclone RPMI 1640 medium (Logan, Utah) supplemented with 10% fetal bovine serum and 20 mM HEPES buffer, final pH 7.2, at 37° C. with a 5% $CO_2$ atmosphere. Cultures are maintained at sub-confluent densities. Human umbilical vein endothelial cells (HUVEC) are purchased from Clonetics, a division of Cambrex (Walkersville, Md.). Cultures are established from cryopreserved stocks using Clonetics EGM-2 medium supplemented with 20 mM HEPES, final pH 7.2, at 37° C. with a 5% $CO_2$ atmosphere.

For proliferation assays, cells are seeded with the appropriate medium into 96 well plates at 1,000-2,500 cells per well, depending on the cell line, and are incubated overnight. The following day, test compound, DMSO solution (negative control), or Actinomycin D (positive control) is added to the appropriate wells as 10× concentrated stocks prepared in phosphate buffered saline. The cell plates are then incubated for an additional 2-5 days, depending on the cell line, to allow proliferation to occur. To measure cell density, 50 µL of WST-1 solution (Roche Applied Science, IN) diluted 1:5 in phosphate buffered saline is added to each well, and the cells incubated for an additional 1-5 hrs, again depending on the cell line. Optical density is determined for each well at 450 nM using a Tecan GeniosPro plate reader (RTP, NC). The percentage of cell growth is determined by comparing the cell growth in the presence of test compounds to the cells treated with DMSO vehicle (control, 100% growth) and cells treated with Actinomycin D (10 µM, 0% growth).

Immediately after the WST-1 determination, the medium is removed from the cell lines, and the plates stored at –80° C. Using these assay plates, relative amounts of DNA in each well are determined using the Cyquant DNA assay kit from R&D Systems (Eugene, Oreg.) following the manufacturer's directions. Results for each compound treatment are compared to DMSO vehicle control (100%) and 10 µM Actinomycin D treated cells (0%).

Results from tests with several compounds of the invention are listed below in Tables 2A and 2B.

TABLE 2A

| Cell Proliferation Assay | $IC_{50}$ (µM) | | | | | |
|---|---|---|---|---|---|---|
| | EX-008 | EX-017 | EX-016 | EX-009 | EX-010 | EX-011 |
| K562 | 0.2498 ± 0.0775 | 1.6878 | 6.3402 | 0.2768 ± 0.0818 | 48.0079 | 4.2777 |
| A375 | 0.0697 ± 0.0093 | 2.5800 | 10.2407 | 0.0760 ± 0.0431 | 2.2647 | 9.5249 |
| NCI-H46 | 0.1416 ± 0.0590 | 2.1326 | 6.5489 | 0.1668 ± 0.0224 | 5.0808 | 8.5921 |
| PC-3 | 0.0405 ± 0.0079 | 1.5477 | 6.4903 | 0.0441 ± 0.0061 | 3.3089 | 5.1178 |

TABLE 2B

| Cell Proliferation Assay | $IC_{50}$ (µM) | | | | |
|---|---|---|---|---|---|
| | EX-012 | EX-014 | EX-013 | EX-015 | EX-007 |
| K562 | 0.1715 ± 0.0723 | 0.3633 ± 0.0574 | 0.2424 ± 0.1185 | 0.3594 ± 0.0424 | 0.0923 ± 0.0327 |
| A375 | 0.2424 ± 0.1917 | 0.6303 ± 0.1061 | 0.1758 ± 0.1452 | 0.4477 ± 0.0502 | 0.0010 ± 0.000466 |
| NCI-H460 | 1.3776 ± 0.4251 | 1.3724 ± 0.3253 | 3.1717 ± 0.7908 | 1.9090 ± 0.5133 | 0.0414 ± 0.0184 |
| PC-3 | <0.08 | 0.3639 ± 0.0078 | 0.1599 ± 0.0814 | 0.3438 ± 0.0102 | 0.0741 ± 0.0706 |

Example 20

Hsp90 Clients and Client-Dependent Signaling Pathways

Cells of multiple human tumor lines were plated in Packard Viewplate-96, incubated overnight, and then treated with test compound for 24 hours. Following treatment, cell monolayers were fixed using standard methods and treated with antibodies targeted to the indicated Hsp90 clients. Primary antibodies were detected using a fluoroscene isothiocyanate (FITC)-conjugated anti-mouse antibody and a tetramethyl rhodamine isothiocyanate (TRITC)-conjugated anti-rabbit antibody. Deoxyribonucleic acid was stained and images were obtained using the compartmental analysis algorithm on a Cellomics Array scan 4.5 according to manufacturer instructions. Average intensities for vehicle control and treated wells were compared with test compound-treated cells to determine the 50% efficacious concentration ($EC_{50}$) values. This methodology was augmented with an alternative method of immune-detection for p-Akt levels. Luminex detection of p-Akt used to directly assay the client effect, Akt, as well as the competency of the signaling cascade, as indicated by phosphorylation of S6 kinase.

Results from tests with several compounds of the invention are listed below in Table 3.

TABLE 3

| Imaging Assay Results | EC$_{50}$ (µM) | | | | | | |
|---|---|---|---|---|---|---|---|
| | EX-008 | EX-009 | EX-012 | EX-014 | EX-013 | EX-015 | EX-007 |
| A375 Imaging Assay | | | | | | | |
| HSP70 induction | 0.0540 ± 0.0157 | 0.0372 ± 0.0068 | 0.0454 ± 0.0298 | 0.4637 ± 0.2906 | 0.0777 ± 0.0301 | 0.3465 ± 0.0218 | 0.000092 ± 0.000133 |
| pS6 inhibition | 0.0591 ± 0.0120 | 0.0285 ± 0.0125 | 0.0738 ± 0.0274 | 0.1148 ± 0.0749 | 0.1562 ± 0.0551 | 0.2409 ± 0.0258 | 0.0043 ± 0.0031 |
| AU565 Imaging Assay | | | | | | | |
| pErk inhibition | 0.1117 ± 0.0196 | 0.1012 ± 0.0230 | 0.3223 ± 0.0859 | 0.4566 ± 0.0365 | 0.3602 ± 0.0408 | 0.8204 ± 0.3150 | 0.0015 ± 0.0014 |
| Her2 degradation | 0.0510 ± 0.0188 | 0.0358 ± 0.0088 | 0.2054 ± 0.0550 | 0.3292 ± 0.0731 | 0.3289 ± 0.0632 | 0.6672 ± 0.2658 | 0.000366 ± 0.00027 |

Example 21

Determination of Affinity for HSP-90
(Heat Shock Protein 90)

Affinity of test compounds for HSP-90 was determined as follows: Protein mixtures obtained from a variety of organ tissues (for example: spleen, liver and lung) were reversibly bound to a purine affinity column to capture purine-binding proteins, especially HSP-90. The purine affinity column was washed several times, and then eluted with 20 µM, 100 µM, and 500 µM of test compound. Compounds of Formula I elute HP-90 in a dose-dependent manner vs. a control elution using dimethylsulfoxide. The elution profile of Formula I compounds was determined by 1-dimensional SDS polyacrylamide gel electrophoresis. Gels were stained with a fluorescent stain such as sypro ruby (a highly sensitive fluorescent protein stain that can readily detect less than 1 fmol of total protein, i.e., less than 0.04 ng for a 40 kDa protein) or silver nitrate. The gels were imaged using a standard flat bed gel imager and the amount of protein estimated by densitometry. The percent of HSP-90 protein eluted from the column at each concentration was determined and IC$_{50}$ values were calculated from these estimates. Compounds of the invention are inhibitors of HSP-90 (heat shock protein 90).

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:
1. A compound of the formula:

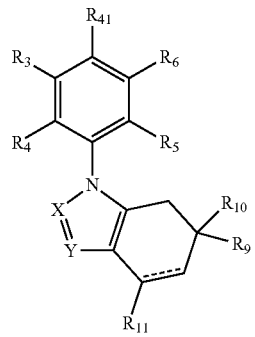

or a pharmaceutically acceptable salt thereof, wherein bond "----" is a single or a double bond;
$R_3$ is hydrogen, halogen, cyano, —C(O)OH, —C(O)—O ($C_1$-$C_6$ alkyl), —N($R_N$)$_2$, $C_1$-$C_6$ alkyl,
  $C_1$-$C_6$ alkoxy, $C_1$-$C_6$ haloalkyl, $C_3$-$C_7$ cycloalkyl, aryl, or heteroaryl, wherein;
    each alkyl, cycloalkyl, aryl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, halo($C_1$-$C_6$)alkyl, halo($C_1$-$C_6$)alkoxy, or carboxamide; and each $R_N$ is independently hydrogen or —$C_1$-$C_6$ alkyl-;
$R_4$ and $R_5$ are independently hydrogen or halogen;
$R_6$ is halogen or —$Z_1R_{Z1}$, and wherein
  $Z_1$ is —O—, —NH—, —S(O)$_p$—, or —S(O)$_2$NH—, wherein p is 0, 1 or 2; and
  $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, SO$_2$, and SO, with the proviso that two O atoms, two S atoms, or an O and S atom are not immediately adjacent to each other, and
  $R_{22}$ is heteroaryl, aryl, saturated or unsaturated $C_3$-$C_{10}$ cycloalkyl, or saturated or unsaturated $C_2$-$C_{10}$ heterocycloalkyl, wherein each aryl, heteroaryl, saturated or unsaturated cycloalkyl, or saturated or unsaturated heterocycloalkyl, independently, is optionally substituted with at least one group, which independently is hydroxy, halo, amino, cyano, carboxy, carboxamido, nitro, oxo, —S—($C_1$-$C_6$)alkyl, —$SO_2$-($C_1$-$C_6$)alkyl, —$SO_2$-aryl, —SO—($C_1$-$C_6$) alkyl, —SO-aryl, —$SO_2NH_2$, —$SO_2$NH—($C_1$-$C_6$) alkyl, —$SO_2$NH-aryl, ($C_1$-$C_6$)alkoxy, or mono- or di-($C_1$-$C_{10}$)alkylamino; and wherein each is optionally fused to a $C_6$-$C_{10}$ aryl group, $C_5$-$C_8$ saturated cyclic group, or a $C_5$-$C_{10}$ heterocycloalkyl group;

and wherein $R_{Z1}$ optionally substituted at any available position independently with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$-($C_1$-$C_6$) alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —SO-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$, wherein Z is $OR_{31}$ or —$N(R_{30})_2$, wherein
each $R_{30}$ is independently hydrogen or $C_1$-$C_6$ alkyl, or $N(R_{30})_2$ represents pyrrolidinyl, piperidinyl, piperazinyl, azepanyl, 1,3- or 1,4-diazepanyl, or morpholinyl, each of which is optionally substituted with hydroxy, amino, aminoalkyl, $C_1$-$C_6$ alkyl, mono- or di($C_1$-$C_6$) alkylamino, $C_1$-$C_6$ alkoxy, or halogen;
$R_{31}$ is hydrogen, $C_1$-$C_{10}$ alkyl, $C_2$-$C_{10}$ alkenyl, $C_2$-$C_{10}$ alkynyl, aryl, heteroaryl, or $C_1$-$C_6$ acyl;
$R_{23}$ is heteroaryl, aryl, saturated or unsaturated $C_5$-$C_{10}$ cycloalkyl, or saturated or unsaturated $C_5$-$C_{10}$ heterocycloalkyl, and each is optionally substituted with at least one group which is independently hydroxy, oxo, halo, amino, cyano, nitro, —SH, —S—($C_1$-$C_6$)alkyl, —$SO_2$-($C_1$-$C_6$)alkyl, —$SO_2$-aryl, —SO—($C_1$-$C_6$)alkyl, —SO-aryl, —$SO_2NH_2$, —$SO_2$NH—($C_1$-$C_6$)alkyl, —$SO_2$NH-aryl, $C_1$-$C_6$ alkoxy, or mono- or di-($C_1$-$C_{10}$)alkylamino;

$R_9$ and $R_{10}$ are independently hydrogen or $C_1$-$C_8$ alkyl; or $R_9$ and $R_{10}$ taken together with the carbon atom to which they are attached form $C_3$-$C_8$ cycloalkyl;

$R_1$ is hydrogen, $C_1$-$C_{10}$ alkyl, $C_2$-$C_{10}$ alkenyl, $C_2$-$C_{10}$ alkynyl, $C_1$-$C_{10}$ haloalkyl, $C_1$-$C_{10}$ alkoxy, mono- or di-($C_1$-$C_{10}$)alkylamino, $C_1$-$C_{10}$ alkoxy($C_1$-$C_{10}$)alkyl, hydroxy($C_1$-$C_{10}$) alkoxy, or amino($C_1$-$C_{10}$)alkoxy-;

$R_{41}$ is a group of the formula

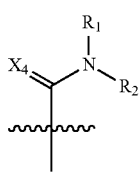

wherein
$R_1$ and $R_2$ are independently H, hydroxy, $C_2$-$C_6$ alkenyl, $C_2$-$C_6$ alkynyl, heteroaryl, aryl, $C_3$-$C_8$ cycloalkyl, heterocycloalkyl, wherein
each cycloalkyl, heterocycloalkyl, aryl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, nitro, halo($C_1$-$C_6$)alkyl, halo($C_1$-$C_6$)alkoxy, or carboxamide;

$X_4$ is oxygen;
X is N or $CR_C$; and
Y is N or $CR_C$;
each $R_C$ is independently is hydrogen, halogen, cyano, nitro, —C(O)$R_{C1}$, $C_1$-$C_{10}$ alkyl, $C_2$-$C_{10}$ alkenyl, $C_2$-$C_{10}$ alkynyl, $C_1$-$C_{10}$ haloalkyl, $C_3$-$C_7$ cycloalkyl, $C_3$-$C_7$ cycloalkyl($C_1$-$C_{10}$)alkyl, heterocycloalkyl, aryl, or heteroaryl, wherein
each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, cyano, nitro, halo($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, halo($C_1$-$C_6$)alkyl, or carboxamide;
$R_{C1}$ is —$C_1$-$C_6$ alkyl, —$OR_{C2}$, or —$N(R_{CN})_2$, wherein
$R_{C2}$ is —H, $C_1$-$C_{10}$ alkyl, $C_1$-$C_{10}$ haloalkyl, $C_3$-$C_7$ cycloalkyl, heterocycloalkyl, aryl, or heteroaryl;
each $R_{CN}$ is independently —H, $C_1$-$C_{10}$ alkyl, $C_1$-$C_{10}$ haloalkyl, $C_3$-$C_7$ cycloalkyl, heterocycloalkyl, $C_1$-$C_6$ acyl, aryl, or heteroaryl, wherein each alkyl, cycloalkyl, heterocycloalkyl, aryl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, nitro, halo($C_1$-$C_6$)alkyl, halo($C_1$-$C_6$) alkoxy, or carboxamide.

2. A compound of claim 1, wherein $Z_1$ is —O— or —NH—.

3. A compound according to claim 1, wherein Re is —$Z_1R_{Z1}$, wherein
$Z_1$ is —NH— and
$R_{Z1}$ is ($C_1$-$C_{14}$)alkyl, ($C_2$-$C_{14}$)alkenyl, ($C_2$-$C_{14}$)alkynyl, aryl, aryl($C_1$-$C_8$)alkyl, ($C_3$-$C_8$)cycloalkenyl, ($C_3$-$C_8$) cycloalkenyl($C_1$-$C_8$)alkyl, ($C_3$-$C_8$)cycloalkyl, ($C_3$-$C_8$) cycloalkyl($C_1$-$C_8$)alkyl, heteroaryl, heteroaryl($C_1$-$C_8$) alkyl, heteroaryl($C_1$-$C_8$)alkylthio($C_1$-$C_8$)alkyl, heteroarylthio($C_1$-$C_8$)alkyl, heterocyclyl, heterocycle ($C_1$-$C_8$)alkyl, or hydroxy($C_1$-$C_8$)alkyl,
wherein each is optionally substituted with 1, 2, 3, 4, or 5 groups which are independently ($C_2$-$C_8$)alkenyl, ($C_1$-$C_8$)alkoxy, ($C_1$-$C_8$)alkoxy($C_1$-$C_8$)alkyl, ($C_1$-$C_8$) alkoxycarbonyl, ($C_1$-$C_8$)alkyl, ($C_1$-$C_8$)alkylcarbonyl, ($C_1$-$C_8$)alkylcarbonyloxy, ($C_1$-$C_8$)alkylsulfinyl, ($C_1$-$C_8$)alkylsulfonyl, ($C_1$-$C_8$)alkylthio, ($C_2$-$C_8$) alkynyl, carboxy, carboxy($C_1$-$C_8$)alkyl, cyano, cyano($C_1$-$C_8$)alkyl, ($C_3$-$C_8$)cycloalkyl, ($C_3$-$C_8$)cycloalkyl($C_1$-$C_8$)alkyl, formyl, halo($C_1$-$C_8$)alkoxy, halo($C_1$-$C_8$)alkyl, halogen, hydroxy, hydroxy($C_1$-$C_8$)alkoxy, hydroxy($C_1$-$C_8$)alkoxy($C_1$-$C_8$)alkoxy, hydroxy($C_1$-$C_8$)alkyl, mercapto, nitro, —$NR_{12}R_{13}$, ($NR_{12}R_{13}$)($C_1$-$C_8$)alkyl, ($NR_{12}R_{13}$)carbonyl, oxo, $HOCH_2CH(NH_2)C(O)O$—, $NH_2(CH_2)_mC(O)O$—, $CH_3NH(CH_2)_mC(O)O$—, $(CH_3)_2N(CH_2)_mC(O)$ O—, $NH_2(CH_2)_tC(O)NH(CH_2)_mC(O)O$—, $R_{13}CH$ $(NH_2)C(O)O$—, $NH_2(CH_2)_mC(R_{13})_2(CH_2)_mC(O)$ O—, $NH_2CH_2CH_2C(O)O$—, $R_{12}ON=CH(CH_2)_n$ O—, $HONHC(O)(CH_2)_nO$—, —$OP(O)(OR_P)_2$, —$OS(O)_2OR_S$, or $R_{20}$;

where each m is independently 1, 2, 3, or 4;
where each n is 1, 2, 3, 4, 5, or 6;
where t is 1, 2, 3, or 4;
where $R_{12}$ and $R_{13}$ are independently —H, $(C_2$-$C_8)$ alkenyl, $(C_1$-$C_8)$alkyl, $(C_1$-$C_8)$alkylcarbonyl, $(C_2$-$C_8)$alkynyl, aryl, aryl$(C_1$-$C_6)$alkyl, $(C_3$-$C_8)$cycloalkyl, $(C_3$-$C_8)$cycloalkyl$(C_1$-$C_8)$alkyl, formyl, heteroaryl, heteroaryl$(C_1$-$C_8)$alkyl, heterocyclyl, or heterocycle$(C_1$-$C_8)$alkyl; or two $R_{12}$ groups together with the carbon to which they are attached form a $(C_3$-$C_8)$cycloalkyl group;
where each $R_P$ and $R_S$ is independently hydrogen, $(C_1$-$C_6)$alkyl, $(C_1$-$C_6)$haloalkyl, or aryl, wherein the alkyl or aryl is optionally substituted with one or more groups independently selected from $(C_1$-$C_6)$alkyl, $(C_1$-$C_6)$alkoxy, halogen, hydroxy, amino, mono- or di-$(C_1$-$C_6)$alkylamino, nitro, halo$(C_1$-$C_6)$alkyl, carboxy, or carboxamide; and
where $R_{20}$ is:

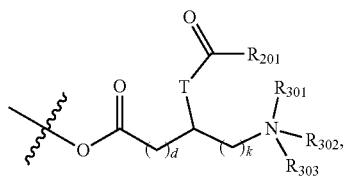

wherein
d and k are integers independently selected from 1 and 2;
$R_{201}$ is $(C_1$-$C_6)$alkyl where the alkyl is optionally substituted with $(C_3$-$C_7)$cycloalkyl, $(C_2$-$C_6)$ alkenyl, $(C_2$-$C_6)$alkynyl, hydroxy, halogen, nitro, or cyano; and
T is O or $NR_{202}$ where $R_{202}$ is hydrogen or $(C_1$-$C_6)$alkyl; and
$R_{301}$ and $R_{302}$ are independently hydrogen or $(C_1$-$C_6)$alkyl, and
$R_{303}$ is absent, hydrogen, or $(C_1$-$C_6)$alkyl.

4. A compound according to claim 3, wherein $R_1$ and $R_2$ are hydrogen.

5. A compound according to claim 1, where X is N.

6. A compound according to claim 1, of formula:

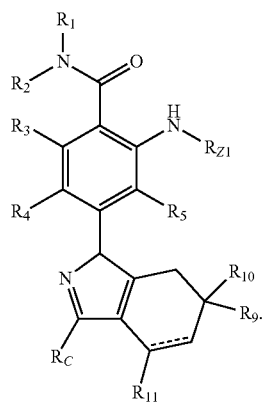

7. A compound according to claim 6, wherein $R_C$ is hydrogen, $C_1$-$C_{10}$ alkyl, or $C_1$-$C_{10}$ haloalkyl.

8. A compound according to claim 1, wherein bond "----" is a single bond.

9. A compound according to claim 1, wherein $R_{11}$ is hydrogen, $C_1$-$C_{10}$ alkyl, $C_1$-$C_{10}$ haloalkyl, $C_1$-$C_{10}$ alkoxy, mono- or di-$(C_1$-$C_{10})$alkylamino, $C_1$-$C_{10}$ alkoxy$(C_1$-$C_{10})$ alkyl, hydroxy$(C_1$-$C_{10})$ alkoxy, or amino$(C_1$-$C_{10})$alkoxy-.

10. A compound according to claim 9, wherein $R_{11}$ is hydrogen or $C_1$-$C_{10}$ alkyl.

11. A compound according to claim 10, wherein $R_{11}$ is hydrogen.

12. A compound according to claim 1, wherein $R_3$ is hydrogen, halogen, $C_1$-$C_6$ alkoxy, or $C_1$-$C_6$ haloalkyl; $R_4$ is hydrogen, and $R_5$ is hydrogen.

13. A compound according to claim 12, wherein $R_3$ is halogen.

14. A compound according to claim 3, where $R_{Z1}$ is aryl, aryl$(C_1$-$C_8)$alkyl, $C_3$-$C_8$ cycloalkyl, $(C_3$-$C_8)$cycloalkyl$(C_1$-$C_8)$alkyl, heteroaryl, heteroaryl$(C_1$-$C_8)$alkyl, heterocyclyl, or heterocycle$(C_1$-$C_8)$alkyl, each of which is optionally substituted with 1, 2, 3, 4, or 5 groups which are independently $(C_2$-$C_8)$alkenyl, $(C_1$-$C_8)$alkoxy, $(C_1$-$C_8)$alkoxy$(C_1$-$C_8)$alkyl, $(C_1$-$C_8)$alkoxycarbonyl, $(C_1$-$C_8)$alkyl, $(C_1$-$C_8)$ alkylcarbonyl, $(C_1$-$C_8)$alkylcarbonyloxy, $(C_1$-$C_8)$ alkylsulfinyl, $(C_1$-$C_8)$alkylsulfonyl, $(C_1$-$C_8)$alkylthio, $(C_2$-$C_8)$alkynyl, carboxy, carboxy$(C_1$-$C_8)$alkyl, cyano, cyano$(C_1$-$C_8)$alkyl, $(C_3$-$C_8)$cycloalkyl, $(C_3$-$C_8)$cycloalkyl$(C_1$-$C_8)$ alkyl, formyl, halo$(C_1$-$C_8)$alkoxy, halo$(C_1$-$C_8)$alkyl, halogen, hydroxy, hydroxy$(C_1$-$C_8)$alkoxy, hydroxy$(C_1$-$C_8)$ alkoxy$(C_1$-$C_8)$alkoxy, hydroxy$(C_1$-$C_8)$alkyl, mercapto, nitro, —$NR_{12}R_{13}$, $(NR_{12}R_{13})(C_1$-$C_8)$alkyl, $(NR_{12}R_{13})$carbonyl, oxo, $HOCH_2CH(NH_2)C(O)O$—, $NH_2(CH_2)_mC(O)$O—, $CH_3NH(CH_2)_mC(O)O$—, $(CH_3)_2N(CH_2)_mC(O)O$—, $NH_2(CH_2)_tC(O)NH(CH_2)_mC(O)O$—, $R_{13}CH(NH_2)C(O)$O—, $NH_2(CH_2)_mC(R_{13})_2(CH_2)_mC(O)O$—, $NH_2CH_2CH_2C$(O)O—, $R_{12}ON{=}CH(CH_2)_nO$—, $HONHC(O)(CH_2)_nO$—, —OP(O)(OR_P)_2$, —OS(O)_2OR_S$, or $R_{20}$.

15. A compound according to claim 3, where $R_{Z1}$ is $C_3$-$C_8$ cycloalkyl or heterocyclyl, each of which is optionally substituted with 1, 2, 3, 4, or 5 groups which are independently $(C_1$-$C_8)$alkoxy, carboxy, cyano, formyl, halo$(C_1$-$C_8)$ alkoxy, halo$(C_1$-$C_8)$alkyl, halogen, hydroxy, hydroxy$(C_1$-$C_8)$alkoxy, hydroxy$(C_1$-$C_8)$alkoxy$(C_1$-$C_8)$alkoxy, $(C_1$-$C_8)$alkoxy, —$NR_{12}R_{13}$, —OP(O)(OR_P)_2$, —OS(O)_2OR_S$, or $R_{20}$.

16. A compound according to claim 3, where $R_{Z1}$ is cyclopentyl or cyclohexyl, each of which is substituted with 1, or 2, or 3 groups independently selected from hydroxy, $C_1$-$C_8$ alkoxy, and $(C_1$-$C_8)$alkylcarbonyloxy.

17. A compound according to claim 1, which is:
2-fluoro-6-((1S,2S)-2-hydroxycyclopentylamino)-4-(3,6,6-trimethyl-4,5,6,7-tetrahydro-1H-indazol-1-yl)benzamide;
2-fluoro-6-((1S,2S)-2-hydroxycyclopentylamino)-4-(3,6,6-trimethyl-6,7-dihydro-1H-indazol-1-yl)benzamide;
2-fluoro-6-(4-hydroxycyclohexylamino)-4-(3,6,6-trimethyl-4,5,6,7-tetrahydro-1H-indazol-1-yl)benzamide;
2-(cyclohexylamino)-6-fluoro-4-(3,6,6-trimethyl-6,7-dihydro-1H-indazol-1-yl)benzamide;
2-(cyclohexylamino)-6-fluoro-4-(3,6,6-trimethyl-4,5,6,7-tetrahydro-1H-indazol-1-yl)benzamide;
2-fluoro-6-(tetrahydrofuran-3-ylamino)-4-(3,6,6-trimethyl-6,7-dihydro-1H-indazol-1-yl)benzamide;
2-fluoro-6-(tetrahydrofuran-3-ylamino)-4-(3,6,6-trimethyl-4,5,6,7-tetrahydro-1H-indazol-1-yl)benzamide;
2-fluoro-6-(2-hydroxycyclohexylamino)-4-(3,6,6-trimethyl-6,7-dihydro-1H-indazol-1-yl)benzamide;
2-fluoro-6-(2-hydroxycyclohexylamino)-4-(3,6,6-trimethyl-4,5,6,7-tetrahydro-1H-indazol-1-yl)benzamide;

2-fluoro-6-(((1r,4r)-4-hydroxycyclohexylamino)-4-(3,4,6,6-tetramethyl-4,5,6,7-tetrahydro-1H-indazol-1-yl)benzamide;

2-fluoro-6-(((1r,4r)-4-hydroxycyclohexylamino)-4-(3,4,6,6-tetramethyl-6,7-dihydro-1H-indazol-1-yl)benzamide; or a pharmaceutically acceptable salt thereof.

18. A compound according to claim 1 which is 2-(trans-4-(cyclopropylmethylamino)cyclohexylamino)-4-(6,6-dimethyl-3-(trifluoromethyl)-4,5,6,7-tetrahydro-1H-indazol-1-yl)benzamide;

2-fluoro-6-(trans-4-methoxycyclohexylamino)-4-(3,6,6-trimethyl-4,5,6,7-tetrahydro-1H-indazol-1-yl)benzamide;

2-(trans-4-hydroxycyclohexylamino)-4-(3-(hydroxymethyl)-6,6-dimethyl-4,5,6,7-tetrahydro-1H-indazol-1-yl)benzamide;

4-(3-ethyl-6,6-dimethyl-4,5,6,7-tetrahydro-1H-indazol-1-yl)-3-fluoro-2-((1S,2S)-2-hydroxycyclohexylamino)benzamide;

4-(3-ethyl-6,6-dimethyl-4,5,6,7-tetrahydro-1H-indazol-1-yl)-2,3,5-trifluoro-6-(trans-4-hydroxycyclohexylamino)benzamide;

2-fluoro-6-(2-oxoazepan-3-ylamino)-4-(3,6,6-trimethyl-4,5,6,7-tetrahydro-1H-indazol-1-yl)benzamide;

2-(1-(2-hydroxyethyl)-1H-pyrazol-4-ylamino)-4-(3,6,6-trimethyl-4,5,6,7-tetrahydro-1H-indazol-1-yl)benzamide;

2-(1-(2-(isobutylamino)ethyl)-1H-pyrazol-4-ylamino)-4-(3,6,6-trimethyl-4,5,6,7-tetrahydro-1H-indazol-1-yl)benzamide;

2-(1,3-dihydroxypropan-2-ylamino)-6-fluoro-4-(3,6,6-trimethyl-4,5,6,7-tetrahydro-1H-indazol-1-yl)benzamide;

(R)-4-(3-(cyclopropylmethyl)-6,6-dimethyl-4,5,6,7-tetrahydro-1H-indazol-1-yl)-5-fluoro-2-(tetrahydrofuran-3-ylamino)benzamide;

4-(6,6-dimethyl-3-(pyridin-2-ylmethyl)-4,5,6,7-tetrahydro-1H-indazol-1-yl)-2-(tetrahydro-2H-pyran-4-ylamino)benzamide;

(S)-4-(3-ethyl-6,6-dimethyl-4,5,6,7-tetrahydro-1H-indazol-1-yl)-2-(tetrahydrofuran-3-ylamino)benzamide;

(S)-4-(6,6-dimethyl-3-(trifluoromethyl)-4,5,6,7-tetrahydro-1H-indazol-1-yl)-2-(piperidin-3-ylamino)benzamide;

(S)-4-(6,6-dimethyl-3-(trifluoromethyl)-4,5,6,7-tetrahydro-1H-indazol-1-yl)-2-(1-neopentylpiperidin-3-ylamino)benzamide;

2-((1S,2S)-2-aminocyclohexylamino)-6-fluoro-4-(3,6,6-trimethyl-4,5,6,7-tetrahydro-1H-indazol-1-yl)benzamide;

2-fluoro-6-((1S,2S)-2-(neopentylamino)cyclohexylamino)-4-(3,6,6-trimethyl-4,5,6,7-tetrahydro-1H-indazol-1-yl)benzamide;

2-(2-((1H-imidazol-2-yl)methylthio)ethylamino)-4-(3-ethyl-6,6-dimethyl-4,5,6,7-tetrahydro-1H-indazol-1-yl)-6-fluorobenzamide;

2-(cyclopent-3-enylamino)-6-fluoro-4-(3,6,6-trimethyl-4,5,6,7-tetrahydro-1H-indazol-1-yl)benzamide;

(S)-4-(6,6-dimethyl-3-(trifluoromethyl)-4,5,6,7-tetrahydro-1H-indazol-1-yl)-2-(1-(prop-2-ynyl)pyrrolidin-3-ylamino)benzamide;

2-(cyclobutylamino)-4-(3-ethyl-6,6-dimethyl-4,5,6,7-tetrahydro-1H-indazol-1-yl)-6-fluorobenzamide;

(R)-4-(6,6-dimethyl-3-(trifluoromethyl)-4,5,6,7-tetrahydro-1H-indazol-1-yl)-2-(2-hydroxypropylamino)benzamide;

2-(trans-4-aminocyclohexylamino)-4-(6,6-dimethyl-3-(trifluoromethyl)-4,5,6,7-tetrahydro-1H-indazol-1-yl)benzamide;

4-(3-ethyl-6,6-dimethyl-4,5,6,7-tetrahydro-1H-indazol-1-yl)-2-fluoro-6-(tetrahydro-2H-pyran-4-ylamino)benzamide;

2-fluoro-6-(tetrahydro-2H-pyran-4-ylamino)-4-(3,6,6-trimethyl-4,5,6,7-tetrahydro-1H-indazol-1-yl)benzamide;

2-fluoro-6-(((S)tetrahydrofuran-3-yl)amino)-4-(4,6,6-trimethyl-3-(trifluoromethyl)-4,5,6,7-tetrahydro-1H-indazol-1-yl)benzamide;

(S)-4-(6,6-dimethyl-3-(trifluoromethyl)-4,5,6,7-tetrahydro-1H-indazol-1-yl)-2-fluoro-6-((tetrahydrofuran-3-yl)amino)benzamide;

2-fluoro-6-(((1S,2S)-2-hydroxycyclopentyl)amino)-4-(3,4,6,6-tetramethyl-4,5,6,7-tetrahydro-1H-indazol-1-yl)benzamide;

4-(3-ethyl-6,6-dimethyl-4,5,6,7-tetrahydro-1H-indazol-1-yl)-2-fluoro-6-((1S,2S)-2-hydroxycyclopentylamino)benzamide;

4-(6,6-dimethyl-3-(trifluoromethyl)-4,5,6,7-tetrahydro-1H-indazol-1-yl)-2-fluoro-6-(((1r,4r)-4-hydroxycylohexyl)amino)benzamide;

2-fluoro-6-(((1r,4r)-4-hydroxycyclohexyl)amino)-4-(4,6,6-trimethyl-3-(trifluoromethyl)-4,5,6,7-tetrahydro-1H-indazol-1-yl)benzamide;

4-(6,6-dimethyl-3-(trifluoromethyl)-6,7-dihydro-1H-indazol-1-yl)-2-fluoro-6-(((1r,4r)-4-hydroxycyclohexyl)amino)benzamide;

2-fluoro-6-(((1r,4r)-4-hydroxycyclohexyl)amino)-4-(4,6,6-trimethyl-3-(trifluoromethyl)-6,7-dihydro-1H-indazol-1-yl)benzamide;

4-(3-ethyl-6,6-dimethyl-4,5,6,7-tetrahydro-1H-indazol-1-yl)-2-fluoro-6-(trans-4-hydroxycyclohexylamino)benzamide;

4-(6,6-dimethyl-3-(trifluoromethyl)-4,5,6,7-tetrahydro-1H-indazol-1-yl)-2-((1S,2S)-2-hydroxycyclohexylamino)benzamide;

4-(6,6-dimethyl-3-(trifluoromethyl)-4,5,6,7-tetrahydro-1H-indazol-1-yl)-2-((1S,2S)-2-hydroxycyclopentylamino)benzamide;

4-(3-ethyl-6,6-dimethyl-4,5,6,7-tetrahydro-1H-indazol-1-yl)-2-((1S,2S)-2-hydroxycyclohexylamino)benzamide;

4-(3-ethyl-6,6-dimethyl-4,5,6,7-tetrahydro-1H-indazol-1-yl)-2-((1S,2S)-2-hydroxycyclopentylamino)benzamide;

(S)-2-(tetrahydrofuran-3-ylamino)-4-(3,6,6-trimethyl-4,5,6,7-tetrahydro-1H-indazol-1-yl)benzamide;

2-((1S,2S)-2-hydroxycyclopentylamino)-4-(3,6,6-trimethyl-4,5,6,7-tetrahydro-1H-indazol-1-yl)benzamide;

2-((1S,2S)-2-hydroxycyclohexylamino)-4-(3,6,6-trimethyl-4,5,6,7-tetrahydro-1H-indazol-1-yl)benzamide;

2-(cyclopentylamino)-4-(3-ethyl-6,6-dimethyl-4,5,6,7-tetrahydro-1H-indazol-1-yl)-6-fluorobenzamide;

(1S,2S)-2-(2-carbamoyl-5-(3-ethyl-6,6-dimethyl-4,5,6,7-tetrahydro-1H-indazol-1-yl)-3-fluorophenylamino)cyclopentyl 2-aminoacetate hydrochloride;

(1S,2S)-2-(2-carbamoyl-3-fluoro-5-(3,6,6-trimethyl-4,5,6,7-tetrahydro-1H-indazol-1-yl)phenylamino)cyclopentyl 2-aminoacetate maleate;

(trans)-4-(2-carbamoyl-5-(3-ethyl-6,6-dimethyl-4,5,6,7-tetrahydro-1H-indazol-1-yl)-3-fluorophenylamino)cyclohexyl 2-aminoacetate hydrochloride;

trans-4-(2-carbamoyl-3-fluoro-5-(3,6,6-trimethyl-4,5,6,7-tetrahydro-1H-indazol-1-yl)phenylamino)cyclohexyl 2-aminoacetate methanesulfonate;

2-(cyclopentylamino)-6-fluoro-4-(3,6,6-trimethyl-4,5,6,7-tetrahydro-1H-indazol-1-yl)benzamide;
4-(6,6-dimethyl-3-(trifluoromethyl)-4,5,6,7-tetrahydro-1H-indazol-1-yl)-2-fluoro-6-((1S,2S)-2-hydroxycyclopentylamino)benzamide;
(1S,2S)-2-(2-carbamoyl-5-(6,6-dimethyl-3-(trifluoromethyl)-4,5,6,7-tetrahydro-1H-indazol-1-yl)-3-fluorophenylamino)cyclopentyl 2-aminoacetate;
4-(6,6-dimethyl-3-(trifluoromethyl)-4,5,6,7-tetrahydro-1H-indazol-1-yl)-2-fluoro-6-(tetrahydro-2H-pyran-4-ylamino)benzamide;
4-(6,6-dimethyl-3-(trifluoromethyl)-4,5,6,7-tetrahydro-1H-indazol-1-yl)-2-fluoro-6-((1S,2S)-2-hydroxycyclohexylamino)benzamide;
(1S,2S)-2-(2-carbamoyl-5-(6,6-dimethyl-3-(trifluoromethyl)-4,5,6,7-tetrahydro-1H-indazol-1-yl)-3-fluorophenylamino)cyclohexyl 2-aminoacetate methanesulfonate;
(1S,2S)-2-(2-carbamoyl-5-(3-ethyl-6,6-dimethyl-4,5,6,7-tetrahydro-1H-indazol-1-yl)phenylamino)cyclohexyl 2-aminoacetate;
(1S,2S)-2-(2-carbamoyl-5-(6,6-dimethyl-3-(trifluoromethyl)-4,5,6,7-tetrahydro-1H-indazol-1-yl)phenylamino)cyclopentyl 2-aminoacetate methanesulfonate;
(1S,2S)-2-(2-carbamoyl-5-(6,6-dimethyl-3-(trifluoromethyl)-4,5,6,7-tetrahydro-1H-indazol-1-yl)phenylamino)cyclohexyl 2-aminoacetate methanesulfonate;
4-(3-ethyl-6,6-dimethyl-4,5,6,7-tetrahydro-1H-indazol-1-yl)-2-((1S,2S)-2-hydroxycyclopentylamino)-6-methoxybenzamide;
5-(6,6-dimethyl-3-(trifluoromethyl)-4,5,6,7-tetrahydro-1H-indazol-1-yl)-3-((trans)-4-hydroxycyclohexylamino)picolinamide;
4-(3-ethyl-6,6-dimethyl-4,5,6,7-tetrahydro-1H-indazol-1-yl)-2-fluoro-6-((1S,2S)-2-hydroxycyclopentylamino)benzamide;
2-(4,4-Difluoro-cyclohexylamino)-6-fluoro-4-(3,6,6-trimethyl-4,5,6,7-tetrahydro-indazol-1-yl)-benzamide;
2-(cyclohexylamino)-4-(6,6-dimethyl-3-(trifluoromethyl)-4,5,6,7-tetrahydro-1H-indazol-1-yl)-6-fluorobenzamide;
trans-4-(2-carbamoyl-3-fluoro-5-(3,6,6-trimethyl-4,5,6,7-tetrahydro-1H-indazol-1-yl)phenylamino)cyclohexyl 2-(tert-butoxycarbonylamino)acetate;
(1S,2S)-2-(2-carbamoyl-5-(6,6-dimethyl-3-(trifluoromethyl)-4,5,6,7-tetrahydro-1H-indazol-1-yl)phenylamino)cyclopentyl 2-(tert-butoxycarbonylamino)acetate;
4-(3-(cyclopropylmethyl)-6,6-dimethyl-4,5,6,7-tetrahydro-1H-indazol-1-yl)-2-fluoro-6-(tetrahydro-2H-pyran-4-ylamino)benzamide;
2-fluoro-6-(tetrahydro-2H-pyran-4-ylamino)-4-(3,6,6-trimethyl-4,5,6,7-tetrahydro-1H-indazol-1-yl)benzamide;
4-(3-ethyl-6,6-dimethyl-4,5,6,7-tetrahydro-1H-indazol-1-yl)-3-fluoro-2-(trans-4-hydroxycyclohexylamino)benzamide;
(S)-2-fluoro-6-(tetrahydrofuran-3-ylamino)-4-(3,6,6-trimethyl-4,5,6,7-tetrahydro-1H-indazol-1-yl)benzamide;
(R)-2-fluoro-6-(tetrahydrofuran-3-ylamino)-4-(3,6,6-trimethyl-4,5,6,7-tetrahydro-1H-indazol-1-yl)benzamide;
2-((1S,2S)-2-aminocyclohexylamino)-4-(3-ethyl-6,6-dimethyl-4,5,6,7-tetrahydro-1H-indazol-1-yl)-6-fluorobenzamide;
4-(3-(cyclopropylmethyl)-6,6-dimethyl-4,5,6,7-tetrahydro-1H-indazol-1-yl)-2-fluoro-6-((1S,2S)-2-hydroxycyclopentylamino)benzamide;
4-(3-(cyclopropylmethyl)-6,6-dimethyl-4,5,6,7-tetrahydro-1H-indazol-1-yl)-2-fluoro-6-((1S,2S)-2-hydroxycyclohexylamino)benzamide;
4-(3-(cyclopropylmethyl)-6,6-dimethyl-4,5,6,7-tetrahydro-1H-indazol-1-yl)-2-fluoro-6-(trans-4-hydroxycyclohexylamino)benzamide;
4-(3-(cyclopropylmethyl)-6,6-dimethyl-4,5,6,7-tetrahydro-1H-indazol-1-yl)-5-fluoro-2-(trans-4-hydroxycyclohexylamino)benzamide;
4-(3-ethyl-6,6-dimethyl-4,5,6,7-tetrahydro-1H-indazol-1-yl)-5-fluoro-2-(trans-4-hydroxycyclohexylamino)benzamide;
2-fluoro-6-((1S,2S)-2-hydroxycyclopentylamino)-4-(3,6,6-trimethyl-4,5,6,7-tetrahydro-1H-indazol-1-yl)benzamide;
2-(cyclopropylmethylamino)-4-(3-ethyl-6,6-dimethyl-4,5,6,7-tetrahydro-1H-indazol-1-yl)-6-fluorobenzamide;
4-(6,6-dimethyl-3-(trifluoromethyl)-4,5,6,7-tetrahydro-1H-indazol-1-yl)-2-fluoro-6-((((1S,2S)-2-hydroxycyclohexyl)amino)benzamide;
4-(6,6-dimethyl-3-(trifluoromethyl)-6,7-dihydro-1H-indazol-1-yl)-2-fluoro-6-((((1S,2S)-2-hydroxycyclohexyl)amino)benzamide;
(S)-4-(3-ethyl-6,6-dimethyl-4,5,6,7-tetrahydro-1H-indazol-1-yl)-2-fluoro-6-(tetrahydrofuran-3-ylamino)benzamide;
4-(3-ethyl-6,6-dimethyl-4,5,6,7-tetrahydro-1H-indazol-1-yl)-2-fluoro-6-((1S,2S)-2-hydroxycyclohexylamino)benzamide;
(R)-4-(3-ethyl-6,6-dimethyl-4,5,6,7-tetrahydro-1H-indazol-1-yl)-2-fluoro-6-(tetrahydrofuran-3-ylamino)benzamide;
(S)-4-(3-(cyclopropylmethyl)-6,6-dimethyl-4,5,6,7-tetrahydro-1H-indazol-1-yl)-2-fluoro-6-(tetrahydrofuran-3-ylamino)benzamide;
(R)-4-(3-(cyclopropylmethyl)-6,6-dimethyl-4,5,6,7-tetrahydro-1H-indazol-1-yl)-2-fluoro-6-(tetrahydrofuran-3-ylamino)benzamide;
4-(3-ethyl-6,6-dimethyl-4,5,6,7-tetrahydro-1H-indazol-1-yl)-3-fluoro-2-(tetrahydro-2H-pyran-4-ylamino)benzamide;
4-(3-(cyclopropylmethyl)-6,6-dimethyl-4,5,6,7-tetrahydro-1H-indazol-1-yl)-3-fluoro-2-(tetrahydro-2H-pyran-4-ylamino)benzamide;
4-(3-ethyl-6,6-dimethyl-4,5,6,7-tetrahydro-1H-indazol-1-yl)-3-fluoro-2-(2-hydroxyethylamino)benzamide;
4-(3-(cyclopropylmethyl)-6,6-dimethyl-4,5,6,7-tetrahydro-1H-indazol-1-yl)-3-fluoro-2-(trans-4-hydroxycyclohexylamino)benzamide;
4-(3-(cyclopropylmethyl)-6,6-dimethyl-4,5,6,7-tetrahydro-1H-indazol-1-yl)-3-fluoro-2-((1S,2S)-2-hydroxycyclohexylamino)benzamide;
4-(3-ethyl-6,6-dimethyl-4,5,6,7-tetrahydro-1H-indazol-1-yl)-2-fluoro-6-((1S,2S)-2-hydroxycyclopentylamino)benzamide;
4-(3-(cyclopropylmethyl)-6,6-dimethyl-4,5,6,7-tetrahydro-1H-indazol-1-yl)-5-fluoro-2-(tetrahydro-2H-pyran-4-ylamino)benzamide;
4-(3-ethyl-6,6-dimethyl-4,5,6,7-tetrahydro-1H-indazol-1-yl)-5-fluoro-2-(tetrahydro-2H-pyran-4-ylamino)benzamide;

(R)-4-(3-ethyl-6,6-dimethyl-4,5,6,7-tetrahydro-1H-indazol-1-yl)-5-fluoro-2-(tetrahydrofuran-3-ylamino)benzamide;
4-(3-(cyclopropylmethyl)-6,6-dimethyl-4,5,6,7-tetrahydro-1H-indazol-1-yl)-5-fluoro-2-((1S,2S)-2-hydroxycyclohexylamino)benzamide;
4-(3-(cyclopropylmethyl)-6,6-dimethyl-4,5,6,7-tetrahydro-1H-indazol-1-yl)-5-fluoro-2-((1S,2S)-2-hydroxycyclopentylamino)benzamide;
4-(3-ethyl-6,6-dimethyl-4,5,6,7-tetrahydro-1H-indazol-1-yl)-5-fluoro-2-((1S,2S)-2-hydroxycyclopentylamino)benzamide;
4-(3-ethyl-6,6-dimethyl-4,5,6,7-tetrahydro-1H-indazol-1-yl)-3,5-difluoro-2-(tetrahydro-2H-pyran-4-ylamino)benzamide;
4-(3-ethyl-6,6-dimethyl-4,5,6,7-tetrahydro-1H-indazol-1-yl)-3,5-difluoro-2-((R)-tetrahydrofuran-3-ylamino)benzamide;
4-(3-(cyclopropylmethyl)-6,6-dimethyl-4,5,6,7-tetrahydro-1H-indazol-1-yl)-3,5-difluoro-2-((R)-tetrahydrofuran-3-ylamino)benzamide;
4-(3-(cyclopropylmethyl)-6,6-dimethyl-4,5,6,7-tetrahydro-1H-indazol-1-yl)-3,5-difluoro-2-(tetrahydro-2H-pyran-4-ylamino)benzamide;
4-(3-ethyl-6,6-dimethyl-4,5,6,7-tetrahydro-1H-indazol-1-yl)-2-fluoro-6-((1S,2S)-2-(neopentylamino)cyclohexylamino)benzamide;
4-(3-ethyl-6,6-dimethyl-4,5,6,7-tetrahydro-1H-indazol-1-yl)-2-fluoro-6-(trans-4-(neopentylamino)cyclohexylamino)benzamide;
4-(3-ethyl-6,6-dimethyl-4,5,6,7-tetrahydro-1H-indazol-1-yl)-2-fluoro-6-(2-oxotetrahydrofuran-3-ylamino)benzamide;
4-(3-(cyclopropylmethyl)-6,6-dimethyl-4,5,6,7-tetrahydro-1H-indazol-1-yl)-3,5-difluoro-2-(trans-4-hydroxycyclohexylamino)benzamide;
methyl 2-(2-carbamoyl-5-(3-ethyl-6,6-dimethyl-4,5,6,7-tetrahydro-1H-indazol-1-yl)-3-fluorophenylamino)-4-hydroxybutanoate;
2-(cyclopent-3-enylamino)-4-(3-ethyl-6,6-dimethyl-4,5,6,7-tetrahydro-1H-indazol-1-yl)-6-fluorobenzamide;
2-(1-acetylpiperidin-4-ylamino)-4-(3-ethyl-6,6-dimethyl-4,5,6,7-tetrahydro-1H-indazol-1-yl)-6-fluorobenzamide;
4-(3-(cyclopropylmethyl)-6,6-dimethyl-4,5,6,7-tetrahydro-1H-indazol-1-yl)-2-fluoro-6-(2-oxotetrahydrofuran-3-ylamino)benzamide;
2-fluoro-6-(4-hydroxycyclohexylamino)-4-(3,6,6-trimethyl-4,5,6,7-tetrahydro-1H-indazol-1-yl)benzamide;
2-fluoro-6-(2-oxotetrahydrofuran-3-ylamino)-4-(3,6,6-trimethyl-4,5,6,7-tetrahydro-1H-indazol-1-yl)benzamide;
4-(3-ethyl-6,6-dimethyl-4,5,6,7-tetrahydro-1H-indazol-1-yl)-2-fluoro-6-(2-oxoazepan-3-ylamino)benzamide;
2-(2,2-dimethoxyethylamino)-4-(3-ethyl-6,6-dimethyl-4,5,6,7-tetrahydro-1H-indazol-1-yl)-6-fluorobenzamide;
4-(3-ethyl-6,6-dimethyl-4,5,6,7-tetrahydro-1H-indazol-1-yl)-2-fluoro-6-(trans-4-hydroxycyclohexylamino)benzamide;
4-(3-ethyl-6,6-dimethyl-4,5,6,7-tetrahydro-1H-indazol-1-yl)-2-fluoro-6-(trans-4-methoxycyclohexylamino)benzamide;
4-(3-ethyl-6,6-dimethyl-4,5,6,7-tetrahydro-1H-indazol-1-yl)-2-fluoro-6-((1S,2R)-2-hydroxycyclohexylamino)benzamide;
4-(3-ethyl-6,6-dimethyl-4,5,6,7-tetrahydro-1H-indazol-1-yl)-2-fluoro-6-((1S,2R)-2-hydroxycyclopentylamino)benzamide;
2-(cyclopentylamino)-4-(3-ethyl-6,6-dimethyl-4,5,6,7-tetrahydro-1H-indazol-1-yl)-6-fluorobenzamide;
(1S,2S)-2-(2-carbamoyl-5-(3-ethyl-6,6-dimethyl-4,5,6,7-tetrahydro-1H-indazol-1-yl)-3-fluorophenylamino)cyclohexyl 2-aminoacetate;
(1S,2S)-2-(2-carbamoyl-5-(3-ethyl-6,6-dimethyl-4,5,6,7-tetrahydro-1H-indazol-1-yl)-3-fluorophenylamino)cyclopentyl 2-aminoacetate;
(1S,2S)-2-(2-carbamoyl-3-fluoro-5-(3,6,6-trimethyl-4,5,6,7-tetrahydro-1H-indazol-1-yl)phenylamino)cyclopentyl 2-aminoacetate;
(1S,2S)-2-(2-carbamoyl-3-fluoro-5-(3,6,6-trimethyl-4,5,6,7-tetrahydro-1H-indazol-1-yl)phenylamino)cyclohexyl 2-aminoacetate;
(trans)-4-(2-carbamoyl-5-(3-ethyl-6,6-dimethyl-4,5,6,7-tetrahydro-1H-indazol-1-yl)-3-fluorophenylamino)cyclohexyl 2-aminoacetate;
(trans)-4-(2-carbamoyl-3-fluoro-5-(3,6,6-trimethyl-4,5,6,7-tetrahydro-1H-indazol-1-yl)phenylamino)cyclohexyl 2-aminoacetate;
(S)-2-fluoro-6-(6-oxotetrahydro-2H-pyran-3-ylamino)-4-(3,6,6-trimethyl-4,5,6,7-tetrahydro-1H-indazol-1-yl)benzamide;
(R)-2-fluoro-6-(6-oxotetrahydro-2H-pyran-3-ylamino)-4-(3,6,6-trimethyl-4,5,6,7-tetrahydro-1H-indazol-1-yl)benzamide;
2-fluoro-6-((cis)-4-hydroxycyclohexylamino)-4-(3,6,6-trimethyl-4,5,6,7-tetrahydro-1H-indazol-1-yl)benzamide;
2-fluoro-6-(oxetan-3-ylamino)-4-(3,6,6-trimethyl-4,5,6,7-tetrahydro-1H-indazol-1-yl)benzamide;
2-(cyclopentylamino)-6-fluoro-4-(3,6,6-trimethyl-4,5,6,7-tetrahydro-1H-indazol-1-yl)benzamide;
2-(cycloheptylamino)-6-fluoro-4-(3,6,6-trimethyl-4,5,6,7-tetrahydro-1H-indazol-1-yl)benzamide;
(trans)-4-(2-carbamoyl-5-(6,6-dimethyl-3-(trifluoromethyl)-4,5,6,7-tetrahydro-1H-indazol-1-yl)-3-fluorophenylamino)cyclohexyl 2-aminoacetate;
4-(6,6-dimethyl-3-(trifluoromethyl)-4,5,6,7-tetrahydro-1H-indazol-1-yl)-2-fluoro-6-((1S,2S)-2-hydroxycyclopentylamino)benzamide;
(1S,2S)-2-(2-carbamoyl-5-(6,6-dimethyl-3-(trifluoromethyl)-4,5,6,7-tetrahydro-1H-indazol-1-yl)-3-fluorophenylamino)cyclopentyl 2-aminoacetate;
4-(6,6-dimethyl-3-(trifluoromethyl)-4,5,6,7-tetrahydro-1H-indazol-1-yl)-2-fluoro-6-(tetrahydro-2H-pyran-4-ylamino)benzamide;
4-(6,6-dimethyl-3-(trifluoromethyl)-4,5,6,7-tetrahydro-1H-indazol-1-yl)-2-fluoro-6-((1S,2S)-2-hydroxycyclohexylamino)benzamide;
(1S,2S)-2-(2-carbamoyl-5-(6,6-dimethyl-3-(trifluoromethyl)-4,5,6,7-tetrahydro-1H-indazol-1-yl)-3-fluorophenylamino)cyclohexyl 2-aminoacetate;
(S)-4-(6,6-dimethyl-3-(trifluoromethyl)-4,5,6,7-tetrahydro-1H-indazol-1-yl)-2-fluoro-6-(tetrahydrofuran-3-ylamino)benzamide;
2-fluoro-6-((1S,2R)-2-hydroxycyclopentylamino)-4-(3,6,6-trimethyl-4,5,6,7-tetrahydro-1H-indazol-1-yl)benzamide;
2-(4,4-difluorocyclohexylamino)-6-fluoro-4-(3,6,6-trimethyl-4,5,6,7-tetrahydro-1H-indazol-1-yl)benzamide;
2-(cyclopentylamino)-4-(6,6-dimethyl-3-(trifluoromethyl)-4,5,6,7-tetrahydro-1H-indazol-1-yl)-6-fluorobenzamide;

2-(cyclohexylamino)-6-fluoro-4-(3,6,6-trimethyl-4,5,6,7-tetrahydro-1H-indazol-1-yl)benzamide;
2-fluoro-6-((1R,2R)-2-hydroxycyclopentylamino)-4-(3,6,6-trimethyl-4,5,6,7-tetrahydro-1H-indazol-1-yl)benzamide;
(1R,2R)-2-(2-carbamoyl-3-fluoro-5-(3,6,6-trimethyl-4,5,6,7-tetrahydro-1H-indazol-1-yl)phenylamino)cyclopentyl 2-aminoacetate;
(S)-(trans-4-(2-carbamoyl-5-(6,6-dimethyl-3-(trifluoromethyl)-4,5,6,7-tetrahydro-1H-indazol-1-yl)phenylamino)cyclohexyl) 2-amino-3-hydroxypropanoate;
trans-4-(2-carbamoyl-5-(6,6-dimethyl-3-(trifluoromethyl)-4,5,6,7-tetrahydro-1H-indazol-1-yl)phenylamino)cyclohexyl 2-(dimethylamino)acetate;
4-(6,6-dimethyl-3-(trifluoromethyl)-4,5,6,7-tetrahydro-1H-indazol-1-yl)-2-(pyrimidin-2-ylamino)benzamide;
4-(6,6-dimethyl-3-(trifluoromethyl)-4,5,6,7-tetrahydro-1H-indazol-1-yl)-2-(pyrimidin-4-ylamino)benzamide;
4-(6,6-dimethyl-3-(trifluoromethyl)-4,5,6,7-tetrahydro-1H-indazol-1-yl)-2-(pyrimidin-5-ylamino)benzamide;
4-(3-(difluoromethyl)-6,6-dimethyl-4, 5,6,7-tetrahydro-1H-indazol-1-yl)-2-(1-(prop-2-ynyl)piperidin-4-ylamino)benzamide;
2-(1-cyclopropylpiperidin-4-ylamino)-4-(3-(difluoromethyl)-6,6-dimethyl-4,5,6,7-tetrahydro-1H-indazol-1-yl)benzamide;
4-(3-(difluoromethyl)-6,6-dimethyl-4,5,6,7-tetrahydro-1H-indazol-1-yl)-2-(1-(2-methoxyethyl)piperidin-4-ylamino)benzamide;
4-(6,6-dimethyl-3-(trifluoromethyl)-4,5,6,7-tetrahydro-1H-indazol-1-yl)-2-(2-(2-hydroxyethoxy)pyridin-4-ylamino)benzamide;
2-(1-(2-(methylamino)ethyl)-1H-pyrazol-4-ylamino)-4-(3,6,6-trimethyl-4,5,6,7-tetrahydro-1H-indazol-1-yl)benzamide;
4-(6,6-dimethyl-3-(trifluoromethyl)-4,5,6,7-tetrahydro-1H-indazol-1-yl)-2-(trans-4-(prop-2-ynylamino)cyclohexylamino)benzamide;
4-(6,6-dimethyl-3-(trifluoromethyl)-4,5,6,7-tetrahydro-1H-indazol-1-yl)-2-(1-(prop-2-ynyl)piperidin-4-ylamino)benzamide;
2-(azetidin-3-ylamino)-4-(6,6-dimethyl-3-(trifluoromethyl)-4,5,6,7-tetrahydro-1H-indazol-1-yl)benzamide;
2-((1S,2S)-2-aminocyclohexylamino)-4-(6,6-dimethyl-3-(trifluoromethyl)-4,5,6,7-tetrahydro-1H-indazol-1-yl)benzamide;
4-(6,6-dimethyl-3-(trifluoromethyl)-4,5,6,7-tetrahydro-1H-indazol-1-yl)-2-(2-(diprop-2-ynylamino)ethylamino)benzamide;
4-(6,6-dimethyl-3-(trifluoromethyl)-4,5,6,7-tetrahydro-1H-indazol-1-yl)-2-(2-(prop-2-ynylamino)ethylamino)benzamide;
4-(6,6-dimethyl-3-(trifluoromethyl)-4,5,6,7-tetrahydro-1H-indazol-1-yl)-2-((1S,2S)-2-(prop-2-ynylamino)cyclohexylamino)benzamide;
2-(1-allylpiperidin-4-ylamino)-4-(6,6-dimethyl-3-(trifluoromethyl)-4,5,6,7-tetrahydro-1H-indazol-1-yl)benzamide;
2-((1R,2R)-2-aminocyclohexylamino)-4-(6,6-dimethyl-3-(trifluoromethyl)-4,5,6,7-tetrahydro-1H-indazol-1-yl)benzamide;
2-((1R,2S)-2-aminocyclohexylamino)-4-(6,6-dimethyl-3-(trifluoromethyl)-4,5,6,7-tetrahydro-1H-indazol-1-yl)benzamide;
(S)-4-(6,6-dimethyl-3-(trifluoromethyl)-4,5,6,7-tetrahydro-1H-indazol-1-yl)-2-(1-(prop-2-ynyl)piperidin-3-ylamino)benzamide;
(S)-2-(1-allylpiperidin-3-ylamino)-4-(6,6-dimethyl-3-(trifluoromethyl)-4,5,6,7-tetrahydro-1H-indazol-1-yl)benzamide;
(R)-4-(6,6-dimethyl-3-(trifluoromethyl)-4,5,6,7-tetrahydro-1H-indazol-1-yl)-2-(piperidin-3-ylamino)benzamide;
4-(6,6-dimethyl-3-(trifluoromethyl)-4,5,6,7-tetrahydro-1H-indazol-1-yl)-2-(2-(pyrimidin-2-ylthio)ethylamino)benzamide;
(R)-4-(6,6-dimethyl-3-(trifluoromethyl)-4,5,6,7-tetrahydro-1H-indazol-1-yl)-2-(1-(prop-2-ynyl)piperidin-3-ylamino)benzamide;
(S)-2-(1-(cyclopropylmethyl)piperidin-3-ylamino)-4-(6,6-dimethyl-3-(trifluoromethyl)-4,5,6,7-tetrahydro-1H-indazol-1-yl)benzamide;
2-(1-(cyclopropylmethyl)piperidin-4-ylamino)-4-(6,6-dimethyl-3-(trifluoromethyl)-4,5,6,7-tetrahydro-1H-indazol-1-yl)benzamide;
2-(3-aminocyclohexylamino)-4-(6,6-dimethyl-3-(trifluoromethyl)-4,5,6,7-tetrahydro-1H-indazol-1-yl)benzamide;
2-(1-(2-(tert-butylamino)ethyl)-1H-pyrazol-4-ylamino)-4-(3,6,6-trimethyl-4,5,6,7-tetrahydro-1H-indazol-1-yl)benzamide;
4-(6,6-dimethyl-3-(trifluoromethyl)-4,5,6,7-tetrahydro-1H-indazol-1-yl)-2-(pyridazin-4-ylamino)benzamide;
(R)-2-(1-(cyclopropylmethyl)piperidin-3-ylamino)-4-(6,6-dimethyl-3-(trifluoromethyl)-4,5,6,7-tetrahydro-1H-indazol-1-yl)benzamide;
2-((1S,2S)-2-(cyclopropylmethylamino)cyclohexylamino)-4-(6,6-dimethyl-3-(trifluoromethyl)-4,5,6,7-tetrahydro-1H-indazol-1-yl)benzamide;
2-(2-(1H-imidazol-2-ylthio)ethylamino)-4-(6,6-dimethyl-3-(trifluoromethyl)-4,5,6,7-tetrahydro-1H-indazol-1-yl)benzamide;
4-(6,6-dimethyl-3-(trifluoromethyl)-4,5,6,7-tetrahydro-1H-indazol-1-yl)-2-((1R,2R)-2-(prop-2-ynylamino)cyclohexylamino)benzamide;
4-(6,6-dimethyl-3-(trifluoromethyl)-4,5,6,7-tetrahydro-1H-indazol-1-yl)-2-((1R,2R)-2-(diprop-2-ynylamino)cyclohexylamino)benzamide;
2-((1R,2R)-2-(cyclopropylmethylamino)cyclohexylamino)-4-(6,6-dimethyl-3-(trifluoromethyl)-4,5,6,7-tetrahydro-1H-indazol-1-yl)benzamide;
2-((1R,2R)-2-(bis(cyclopropylmethyl)amino)cyclohexylamino)-4-(6,6-dimethyl-3-(trifluoromethyl)-4,5,6,7-tetrahydro-1H-indazol-1-yl)benzamide;
2-((1S,2S)-2-(diethylamino)cyclohexylamino)-4-(6,6-dimethyl-3-(trifluoromethyl)-4,5,6,7-tetrahydro-1H-indazol-1-yl)benzamide;
2-((1S,2S)-2-(cyclopropylamino)cyclohexylamino)-4-(6,6-dimethyl-3-(trifluoromethyl)-4,5,6,7-tetrahydro-1H-indazol-1-yl)benzamide;
4-(6,6-dimethyl-3-(trifluoromethyl)-4,5,6,7-tetrahydro-1H-indazol-1-yl)-2-(trans-4-(neopentylamino)cyclohexylamino)benzamide;
4-(6,6-dimethyl-3-(trifluoromethyl)-4,5,6,7-tetrahydro-1H-indazol-1-yl)-2-((1S,2S)-2-(neopentylamino)cyclohexylamino)benzamide;
(1S,2S)-2-(2-carbamoyl-5-(3-ethyl-6,6-dimethyl-4,5,6,7-tetrahydro-1H-indazol-1-yl)phenylamino)cyclohexyl 2-aminoacetate;
4-(3-(difluoromethyl)-6,6-dimethyl-4,5,6,7-tetrahydro-1H-indazol-1-yl)-2-(2,2,6,6-tetramethylpiperidin-4-ylamino)benzamide;

(1S,2S)-2-(2-carbamoyl-5-(6,6-dimethyl-3-(trifluoromethyl)-4,5,6,7-tetrahydro-1H-indazol-1-yl)phenylamino)cyclopentyl 2-aminoacetate;
(1S,2S)-2-(2-carbamoyl-5-(6,6-dimethyl-3-(trifluoromethyl)-4,5,6,7-tetrahydro-1H-indazol-1-yl)phenylamino)cyclohexyl 2-aminoacetate;
(1S,2S)-2-(2-carbamoyl-5-(6,6-dimethyl-3-(trifluoromethyl)-4,5,6,7-tetrahydro-1H-indazol-1-yl)phenylamino)cyclopentyl 1-aminocyclopropanecarboxylate methanesulfonate;
trans-4-(2-carbamoyl-5-(6,6-dimethyl-3-(trifluoromethyl)-4,5,6,7-tetrahydro-1H-indazol-1-yl)phenylamino)cyclohexyl 2-(2-aminoacetamido)acetate 2,2,2-trifluoroacetate;
4-(6,6-dimethyl-3-(trifluoromethyl)-4,5,6,7-tetrahydro-1H-indazol-1-yl)-2-(4-(2-(methoxyimino)ethoxy)cyclohexylamino)benzamide;
4-(6,6-dimethyl-3-(trifluoromethyl)-4,5,6,7-tetrahydro-1H-indazol-1-yl)-2-(4-(2-(phenoxyimino)ethoxy)cyclohexylamino)benzamide;
2-(trans-4-(2-hydroxyethoxy)cyclohexylamino)-4-(3,6,6-trimethyl-4,5,6,7-tetrahydro-1H-indazol-1-yl)benzamide;
(R)-2-(tetrahydrofuran-3-ylamino)-4-(3,6,6-trimethyl-4,5,6,7-tetrahydro-1H-indazol-1-yl)benzamide;
4-(6,6-dimethyl-3-(trifluoromethyl)-4,5,6,7-tetrahydro-1H-indazol-1-yl)-2-(4-(2-(hydroxyamino)-2-oxoethoxy)cyclohexylamino)benzamide;
2-(trans-4-(2-(2-hydroxyethoxy)ethoxy)cyclohexylamino)-4-(3,6,6-trimethyl-4,5,6,7-tetrahydro-1H-indazol-1-yl)benzamide;
2-(cyclobutylamino)-4-(6,6-dimethyl-3-(trifluoromethyl)-4,5,6,7-tetrahydro-1H-indazol-1-yl)benzamide;
2-(4-(2-hydroxyethoxy)cyclohexylamino)-4-(3,6,6-trimethyl-4,5,6,7-tetrahydro-1H-indazol-1-yl)benzamide;
4-(6,6-dimethyl-3-(trifluoromethyl)-4,5,6,7-tetrahydro-1H-indazol-1-yl)-2-(2-hydroxyethylamino)benzamide;
2-(cyclobutylamino)-4-(3-ethyl-6,6-dimethyl-4,5,6,7-tetrahydro-1H-indazol-1-yl)benzamide;
2-(trans-4-hydroxycyclohexylamino)-4-(3-(3-methoxyphenyl)-6,6-dimethyl-4,5,6,7-tetrahydro-1H-indazol-1-yl)benzamide;
4-(3-benzyl-6,6-dimethyl-4,5,6,7-tetrahydro-1H-indazol-1-yl)-2-(trans-4-hydroxycyclohexylamino)benzamide;
4-(6,6-dimethyl-3-(1H-pyrazol-4-yl)-4,5,6,7-tetrahydro-1H-indazol-1-yl)-2-(trans-4-hydroxycyclohexylamino)benzamide;
4-(6,6-dimethyl-3-(pyridin-3-ylmethyl)-4,5,6,7-tetrahydro-1H-indazol-1-yl)-2-(trans-4-hydroxycyclohexylamino)benzamide;
4-(6,6-dimethyl-3-(pyridin-2-ylmethyl)-4,5,6,7-tetrahydro-1H-indazol-1-yl)-2-(trans-4-hydroxycyclohexylamino)benzamide;
4-(3-(cyclopropylmethyl)-6,6-dimethyl-4,5,6,7-tetrahydro-1H-indazol-1-yl)-2-(tetrahydro-2H-pyran-4-ylamino)benzamide;
4-(6,6-dimethyl-3-(trifluoromethyl)-4,5,6,7-tetrahydro-1H-indazol-1-yl)-2-(2-hydroxycyclohexylamino)benzamide;
4-(6,6-dimethyl-3-(pyridin-2-ylmethyl)-4,5,6,7-tetrahydro-1H-indazol-1-yl)-2-(2-hydroxyethylamino)benzamide;
4-(3-benzyl-6,6-dimethyl-4,5,6,7-tetrahydro-1H-indazol-1-yl)-2-(2-hydroxyethylamino)benzamide;
4-(3-(cyclopropylmethyl)-6,6-dimethyl-4,5,6,7-tetrahydro-1H-indazol-1-yl)-2-(2-hydroxyethylamino)benzamide;
4-(3-benzyl-6,6-dimethyl-4,5,6,7-tetrahydro-1H-indazol-1-yl)-2-(tetrahydro-2H-pyran-4-ylamino)benzamide;
(R)-4-(6,6-dimethyl-3-(trifluoromethyl)-4,5,6,7-tetrahydro-1H-indazol-1-yl)-2-(1-hydroxypropan-2-ylamino)benzamide;
(S)-4-(6,6-dimethyl-3-(trifluoromethyl)-4,5,6,7-tetrahydro-1H-indazol-1-yl)-2-(1-hydroxypropan-2-ylamino)benzamide;
(S)-4-(6,6-dimethyl-3-(trifluoromethyl)-4,5,6,7-tetrahydro-1H-indazol-1-yl)-2-(2-hydroxypropylamino)benzamide;
4-(6,6-dimethyl-3-(pyridin-3-ylmethyl)-4,5,6,7-tetrahydro-1H-indazol-1-yl)-2-(tetrahydro-2H-pyran-4-ylamino)benzamide;
4-(6,6-dimethyl-3-(pyridin-4-ylmethyl)-4,5,6,7-tetrahydro-1H-indazol-1-yl)-2-(2-hydroxyethylamino)benzamide;
4-(6,6-dimethyl-3-(pyridin-3-ylmethyl)-4,5,6,7-tetrahydro-1H-indazol-1-yl)-2-(2-hydroxyethylamino)benzamide;
4-(6,6-dimethyl-3-(thiophen-3-ylmethyl)-4,5,6,7-tetrahydro-1H-indazol-1-yl)-2-(2-hydroxyethylamino)benzamide;
4-(6,6-dimethyl-3-(pyridin-4-ylmethyl)-4,5,6,7-tetrahydro-1H-indazol-1-yl)-2-(tetrahydro-2H-pyran-4-ylamino)benzamide;
4-(6,6-dimethyl-3-(pyridin-3-ylmethyl)-4,5,6,7-tetrahydro-1H-indazol-1-yl)-2-(trans-4-hydroxycyclohexylamino)benzamide;
4-(6,6-dimethyl-3-(trifluoromethyl)-4,5,6,7-tetrahydro-1H-indazol-1-yl)-2-((1S,2S)-2-hydroxycyclohexylamino)benzamide;
(R)-4-(3-(cyclopropylmethyl)-6,6-dimethyl-4,5,6,7-tetrahydro-1H-indazol-1-yl)-2-(tetrahydrofuran-3-ylamino)benzamide;
4-(6,6-dimethyl-3-(trifluoromethyl)-4,5,6,7-tetrahydro-1H-indazol-1-yl)-2-((1R,2R)-2-hydroxycyclohexylamino)benzamide;
4-(6,6-dimethyl-3-(trifluoromethyl)-4,5,6,7-tetrahydro-1H-indazol-1-yl)-2-((1R,2R)-2-hydroxycyclopentylamino)benzamide;
4-(6,6-dimethyl-3-(trifluoromethyl)-4,5,6,7-tetrahydro-1H-indazol-1-yl)-2-((1S,2S)-2-hydroxycyclopentylamino)benzamide;
4-(3-ethyl-6,6-dimethyl-4,5,6,7-tetrahydro-1H-indazol-1-yl)-2-((1S,2S)-2-hydroxycyclohexylamino)benzamide;
4-(3-(cyclopropylmethyl)-6,6-dimethyl-4,5,6,7-tetrahydro-1H-indazol-1-yl)-2-((1S,2S)-2-hydroxycyclopentylamino)benzamide;
4-(3-(cyclopropylmethyl)-6,6-dimethyl-4,5,6,7-tetrahydro-1H-indazol-1-yl)-2-((1S,2S)-2-hydroxycyclohexylamino)benzamide;
4-(3-ethyl-6,6-dimethyl-4,5,6,7-tetrahydro-1H-indazol-1-yl)-2-((1S,2S)-2-hydroxycyclopentylamino)benzamide;
(S)-2-(tetrahydrofuran-3-ylamino)-4-(3,6,6-trimethyl-4,5,6,7-tetrahydro-1H-indazol-1-yl)benzamide;
2-((1S,2S)-2-hydroxycyclopentylamino)-4-(3,6,6-trimethyl-4,5,6,7-tetrahydro-1H-indazol-1-yl)benzamide;
2-((1S,2S)-2-hydroxycyclohexylamino)-4-(3,6,6-trimethyl-4,5,6,7-tetrahydro-1H-indazol-1-yl)benzamide;
2-(oxetan-3-ylamino)-4-(3,6,6-trimethyl-4,5,6,7-tetrahydro-1H-indazol-1-yl)benzamide;

(S)-4-(6,6-dimethyl-3-(trifluoromethyl)-4,5,6,7-tetrahydro-1H-indazol-1-yl)-2-(tetrahydrofuran-3-ylamino)benzamide;

4-(6-ethyl-3,6-dimethyl-4,5,6,7-tetrahydro-1H-indazol-1-yl)-2-((trans)-4-hydroxycyclohexylamino)benzamide;

2-(cyclopentylamino)-4-(3,6,6-trimethyl-4,5,6,7-tetrahydro-1H-indazol-1-yl)benzamide;

2-(cycloheptylamino)-4-(3,6,6-trimethyl-4,5,6,7-tetrahydro-1H-indazol-1-yl)benzamide;

4-(3-ethyl-6,6-dimethyl-4,5,6,7-tetrahydro-1H-indazol-1-yl)-2-methoxy-6-(tetrahydro-2H-pyran-4-ylamino)benzamide;

4-(6,6-dimethyl-3-(2,2,2-trifluoroethyl)-4,5,6,7-tetrahydro-1H-indazol-1-yl)-2-(trans-4-hydroxycyclohexylamino)benzamide;

4-(6,6-dimethyl-3-(trifluoromethyl)-4,5,6,7-tetrahydro-1H-indazol-1-yl)-2-((1S,2R)-2-hydroxycyclopentylamino)benzamide;

2-(cyclopentylamino)-4-(6,6-dimethyl-3-(trifluoromethyl)-4,5,6,7-tetrahydro-1H-indazol-1-yl)benzamide;

2-(cyclohexylamino)-4-(3,6,6-trimethyl-4,5,6,7-tetrahydro-1H-indazol-1-yl)benzamide; or a pharmaceutically acceptable salt thereof.

19. A pharmaceutical composition comprising at least one compound or salt according to claim 1 and a pharmaceutically acceptable solvent, carrier, excipient, adjuvant or a combination thereof.

20. A method of treating an HSP-90-mediated disease which is cancer, inflammation, infection, or arthritis comprising administering to a patient in need of such treatment a therapeutically effective amount of an HSP-90 inhibiting compound or salt according to claim 1.

21. A method for treating a subject suffering from a disease or disorder of proteins that are either client proteins for HSP-90 or indirectly affect its client proteins, comprising administering to a subject in need of such treatment a therapeutically effective amount of an HSP-90 inhibiting compound or salt according to claim 1.

* * * * *